(12) United States Patent
Schmitt et al.

(10) Patent No.: US 10,538,572 B2
(45) Date of Patent: Jan. 21, 2020

(54) T CELL IMMUNOTHERAPY SPECIFIC FOR WT-1

(71) Applicant: Fred Hutchinson Cancer Research Center, Seattle, WA (US)

(72) Inventors: Thomas M. Schmitt, Seattle, WA (US); Philip D. Greenberg, Mercer Island, WA (US); Hieu Nguyen, Federal Way, WA (US)

(73) Assignee: FRED HUTCHINSON CANCER RESEARCH CENTER, Seattle, WA (US)

( * ) Notice: Subject to any disclaimer, the term of this patent is extended or adjusted under 35 U.S.C. 154(b) by 0 days.

(21) Appl. No.: 14/813,782

(22) Filed: Jul. 30, 2015

(65) Prior Publication Data

US 2016/0083449 A1 Mar. 24, 2016

Related U.S. Application Data

(60) Provisional application No. 62/033,045, filed on Aug. 4, 2014, provisional application No. 62/164,783, filed on May 21, 2015.

(51) Int. Cl.
| | |
|---|---|
| *C07K 16/28* | (2006.01) |
| *A61K 39/00* | (2006.01) |
| *C07K 14/00* | (2006.01) |
| *C07K 16/30* | (2006.01) |
| *C07K 14/725* | (2006.01) |
| *A61K 35/17* | (2015.01) |
| *A61K 38/17* | (2006.01) |
| *A61K 38/20* | (2006.01) |
| *A61K 38/00* | (2006.01) |

(52) U.S. Cl.
CPC .......... *C07K 14/7051* (2013.01); *A61K 35/17* (2013.01); *A61K 38/1774* (2013.01); *A61K 38/2013* (2013.01); *A61K 38/2086* (2013.01); *A61K 38/00* (2013.01); *A61K 2039/505* (2013.01); *C07K 2319/00* (2013.01)

(58) Field of Classification Search
USPC .......................................................... 424/12
See application file for complete search history.

(56) References Cited

U.S. PATENT DOCUMENTS

| | | | |
|---|---|---|---|
| 7,342,092 B2 | 3/2008 | Sugiyama | |
| 7,608,685 B1 | 10/2009 | Sugiyama et al. | |
| 7,622,119 B2 | 11/2009 | Sugiyama | |
| 2004/0171148 A1 | 9/2004 | Schmitt et al. | |
| 2012/0225481 A1* | 9/2012 | Jakobsen | C07K 14/7051 435/369 |
| 2015/0353622 A1* | 12/2015 | Blankenstein | C07K 16/30 424/139.1 |

FOREIGN PATENT DOCUMENTS

| | | | |
|---|---|---|---|
| WO | 00/026249 A1 | | 5/2000 |
| WO | 2010/058023 A1 | | 5/2010 |
| WO | WO 2011001152 | * | 1/2011 |
| WO | 2012/038055 A1 | | 3/2012 |
| WO | 2013/166321 A1 | | 11/2013 |
| WO | 2014/018863 A1 | | 1/2014 |
| WO | WO 2014/118236 | * | 8/2014 |

OTHER PUBLICATIONS

Janeway et al., Immunobiology, 5th Ed., Garland Science, 2001, pp. 106-108, 117-118 and 260-263.*
Manning et al., Immunity, 1998, 8:413-425.*
Garcia et al., Cell, 2005, 122: 333-336.*
Goyarts et al., Molecular Immunology, 1998, 35:593-607.*
Kessels et al., Proceeding of the National Academy Science, 2000, 97:14578-83.*
Ngo, in The Protein Folding Problem and Tertiary Structure Prediction, Merz et al. (eds.), Birkhauser Boston: Boston, MA, pp. 433 and 492-495, 1994.*
T-cell receptor From Wikipedia, the free encyclopedia pp. 1-7, downloaded Apr. 6, 2017.*
Roitt, Essential Immunology, Blackwell Scientific Publications, 1988; sixth edition; pp. 47-49.*
Edwards et al Repertoire; Isolation of Over One Thousand Different Antibodies to a Single Protein, BLyS J. Mol. Biol. (2003) 334, 103-118.*
Lloyd et al Modelling the human immune response: performance of a 10 11 human antibody repertoire against a broad panel of therapeutically relevant antigens Protein Engineering, Design & Selection vol. 22 No. 3 pp. 159-168, 2009.*
USPTO presentation on Antibodies and the Written Description Requirement of 35 U.S.C.112(a)by Dan Kolker, pp. 1-36, May 15, 2019.*
Aggen "Engineering Human Single-Chain T Cell Receptors," Thesis, Graduate College of the University of Illinois at Urbana-Champaign, 2010, 181 pages.
Cavallo et al., "2011: the immune hallmarks of cancer," *Cancer Immunol Immunother* 60:319-326, 2011.
Chapuis et al., "Transferred WT1-reactive CD8+ T cells can mediate antileukemic activity and persist in post-transplant patients," *Sci Transl Med.* 5(174):174ra27, 2013, 25 pages.
Cheever et al., "The Prioritization of Cancer Antigens: A National Cancer Institute Pilot Project for the Acceleration of Translational Research," *Clin Cancer Res.* 15(17):5323-5337, 2009.
Chervin et al., "Engineering higher affinity T cell receptors using a T cell display system," *Journal of Immunological Methods* 339:175-184, 2008.
Gaiger et al., "Immunity to WT1 in the animal model and in patients with acute myeloid leukemia," *Blood* 96(4): 1480-1489, 2000.
Hanahan et al., "The Hallmarks of Cancer," *Cell* 100(1):57-70, 2000.

(Continued)

*Primary Examiner* — Maria G Leavitt
(74) *Attorney, Agent, or Firm* — Seed IP Law Group LLP

(57) ABSTRACT

The present disclosure provides high affinity and enhanced affinity T cell receptors specific for human Wilms tumor protein 1 (WT-1) epitopes for use in treating diseases or disorders, such as cancer cells that overexpress WT-1.

47 Claims, 17 Drawing Sheets

Specification includes a Sequence Listing.

(56) References Cited

OTHER PUBLICATIONS

Hanahan et al., "Hallmarks of Cancer: The Next Generation," *Cell* 144(5):646-674, 2011.
Heemskerk et al., "Efficiency of T-cell receptor expression in dual-specific T cells is controlled by the intrinsic qualities of the TCR chains within the TCR-CD3 complex," *Blood* 109(1):235-243, 2007.
Ichinohasama et al., "Sensitive immunohistochemical detection of Wt1protein in tumors with anti-WT1 antibody against WT1 235 peptide," *Cancer Science* 101(5):1089-1092, 2010.
Inoue et al., "WT1 as a New Prognostic Factor and a New Marker for the Detection of Minimal Residual Disease in Acute Leukemia," *Blood* 84(9):3071-3079, 1994.
Kuball et al., "Facilitating matched pairing and expression of TCR chains introduced into human T cells," *Blood* 109(6):2331-2338, 2007.
Kyrgidis et al., "Melanoma: Stem cells, sun exposure and hallmarks for carcinogenesis, molecular concepts and future clinical implications," *J Carcinog.* 9(3): 2010, 25 pages.
Nakatsuka et al., "Immunohistochemical detection of WT1 protein in a variety of cancer cells," *Modern Pathology* 19:804-814 2006.
Ogawa et al., "The usefulness of monitoring WT1 gene transcripts for the prediction and management of relapse following allogeneic stem cell transplantation in acute type leukemia," *Blood* 101(5):1698-1704, 2003.
Oka et al., "WT1 Peptide Cancer Vaccine for Patients with Hematopoietic Malignancies and Solid Cancers," *The Scientific World Journal* 7:649-665, 2007.
Park et al., "Cancer Stem Cell-Directed Therapies: Recent Data From the Laboratory and Clinic," *Molecular Therapy* 17(2):219-230, 2009.
Provasi et al., "Editing T cell specificity towards leukemia by zinc finger nucleases and lentiviral gene transfer," *Nature Medicine* 18(5):807-815, 2012.
Richman et al., "Display, engineering, and applications of antigen-specific T cell receptors," *Biomolecular Engineering* 24(4):361-373, 2007.
Robins et al., "Comprehensive assessment of T-cell receptor β-chain diversity in αβ T cells," *Blood* 14(19):4099-4107, 2009.
Robins et al., "Overlap and effective size of the human CD8+ T-cell receptor repertoire," *Sci Transl Med.* 2(47):47ra64 2010, 9 pages.
Robins et al., "Ultra-sensitive detection of rare T cell clones," *J Immunol Methods* 375(0):14-19, 2012. (9 pages).
Schmitt et al., "Enhanced-affinity murine T-cell receptors for tumor/self-antigens can be safe in gene therapy despite surpassing the threshold for thymic selection," *Blood* 122(3):348-356, 2013.
Schmitt et al., "T Cell Receptor Gene Therapy for Cancer," *Human Gene Therapy* 20:1240-1248, 2009.
Scholten et al., "Codon modification of T cell receptors allows enhanced functional expression in transgenic human T cells," *Clinical Immunology* 119:135-145, 2006.
Stromnes et al., "Re-adapting T cells for cancer therapy: from mouse models to clinical trials," *Immunological Reviews* 257:145-164, 2014.
Szymczak et al., "Correction of multi-gene deficiency in vivo using a single 'self-cleaving' 2A peptide-based retroviral vector," *National Biotechnology*(5):589-594, 2004.
Udyavar et al., "Subtle affinity-enhancing mutations in a MOG-specific TCR alter specificity and generate new self-reactivity," *J Immunol.* 182(7):4439-4447, 2009. (19 pages).
Van Coppernolle et al., "Notch induces human T-cell receptor γδ+ thymocytes to differentiate along a parallel, highly proliferative and bipotent CD4 CD8 double-positive pathway," *Leukemia* 26:127-138, 2012.
Van Coppernolle et al., "Functionally Mature CD4 and CD8 TCRαβ Cells Are Generated in OP9-DL1 Cultures from Human CD34+ Hematopoietic Cells," *Journal of Immunology* 183(8):4859-4870, 2009.
Van Driessche et al., "Active Specific Immunotherapy Targeting the Wilms' Tumor Protein 1 (WT1) for Patients with Hematological Malignancies and Solid Tumors: Lessons from Early Clinical Trials," *The Oncologist* 17:250-259, 2012.
Weber et al., "Class II-restricted T cell receptor engineered in vitro for higher affinity retains peptide specificity and function," *PNAS* 102(52)19033-19038, 2005.
Yang et al., "Clinical-scale lentiviral vector transduction of PBL for TCR gene therapy and potential for expression in less-differentiated cells," *J Immunother.* 31(9):830-839, 2008. (15 pages).
Zhao et al., "High-Affinity TCRs Generated by Phage Display Provide CD4+ T Cells with the Ability to Recognize and Kill Tumor Cell Lines," *J Immunol.* 179(9):5845-5854, 2007. (19 pages).
Greenberg, "Building a Better T Cell for Targeting Tumors," SITC, North Bethesda, Maryland, Oct. 26-28, 2012, 31 pages.

\* cited by examiner

T CELL IMMUNOTHERAPY SPECIFIC FOR WT-1

STATEMENT OF GOVERNMENT INTEREST

This invention was made with government support under CA018029awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_427_SEQUENCE_LISTING.txt. The text file is 142 KB, was created on Feb. 22, 2018, and is being submitted electronically via EFS-Web.

BACKGROUND

Technical Field

The present disclosure relates generally to high affinity or enhanced affinity T cell receptors (TCRs) specific for antigens associated with a hyperproliferative disease. More specifically, the present disclosure relates to TCRs with high or enhanced affinity against a human Wilms tumor protein 1 (WT-1) epitope, T cells expressing such WT-1-specific TCRs, nucleic acids encoding the same, and compositions for use in treating diseases or disorders in which cells overexpress WT-1, such as in cancer.

Description of the Related Art

T cell receptor (TCR) gene therapy is an emerging treatment approach designed to overcome obstacles associated with conventional T cell adoptive immunotherapy, such as the extensive time and labor required to isolate, characterize, and expand tumor antigen-specific T cells (Schmitt et al., *Hum. Gene Ther.* 20:1240, 2009). Another hurdle is that most identified tumor antigens that can be targeted by conventional T cell immunotherapy are over-expressed self-proteins, so high affinity T cells specific for these antigens are generally eliminated during thymic selection, and are rare or non-existent in the peripheral repertoire.

Strategies are being developed to enhance the affinity of TCRs intended for use in TCR gene therapy (Udyavar et al., *J. Immunol.* 182:4439, 2009; Zhao et al., *J. Immunol.* 179:5845, 2007; Richman and Kranz, *Biomol. Eng.* 24:361, 2007). These approaches generally entail generating libraries of mutated TCR genes and subsequent screening for mutations that confer higher affinity for the complex of target peptide with major histocompatibility complex (MHC) ligand. Mutations are usually targeted to the complementarity determining regions (CDRs) known to interact with the peptide (CDR3) and/or MHC (CDR1/2) (Wucherpfennig et al., *Cold Spring Harb. Perspect. Biol.* 2:a005140, 2010). But, changes to MHC contact residues may create a risk in the clinical setting since this can increase the affinity for MHC independent of peptide or increase the likelihood of cross-reactivity (off-target effects). This notion has been highlighted by the results of a trial, in which T cells expressing a TCR containing CDR2 mutations were infused into patients and mediated rapid and fatal toxicity from unpredicted cross-reactivity with a disparate self-antigen expressed in the heart (Cameron et al., *Sci. Transl. Med.* 5:197ra103, 2013; Linette et al., *Blood* 122:863, 2013). Certain available methodologies used to target specific CDR residues for amino acid substitution limit the diversity of the generated libraries, as these are generally constrained by the length of the parental CDR sequence. In contrast, the natural process generally produces greater diversity in the thymus, where the V(D)J recombination machinery active during T cell development results in TCR gene rearrangements that generate highly diverse CDRs, particularly CDR3s, that vary in both length and amino acid composition.

A strategy for targeted T-cell therapy achieving a maximal clinical effect that would be accompanied by minimal immunological toxicity involves identifying disease associated antigens with high expression in and presentation by, for example, a malignant cell compartment, but without significant expression in normal tissue. For example, several acute myeloid leukemia (AML) associated antigens have been described, and Wilms tumor protein 1 (WT-1) has been shown to be expressed in the leukemia stem cell (LSC) compartment of the majority of AML patients at levels significantly higher than in physiological hematopoietic stem cells (HSCs). WT-1 is being targeted in clinical trials both with adoptive T-cell transfer and peptide vaccination (see, e.g., U.S. Pat. Nos. 7,342,092; 7,608,685; 7,622,119). In addition, WT-1 expression has been reported to be a marker of minimal residual disease because increased transcript levels in patients with AML in morphologic remission were predictive of overt clinical relapse (Inoue et al., *Blood* 84:3071, 1994; Ogawa et al., *Blood* 101:1698, 2003).

Since WT-1 is an intracellular (usually nuclear) protein, immunotherapies targeting WT-1 generally use cellular approaches aimed at generating WT-1-specific CD8+ cytotoxic T lymphocyte (CTL) responses that recognize peptides presented on the cell surface by MHC class I molecules. For induction of a CTL response, intracellular proteins are usually degraded by the proteasome or endo/lysosomes, with the resulting peptide fragments binding to MHC class I or class II molecules. These peptide-MHC complexes are displayed on the cell surface where they are bound by T cells via the peptide-MHC-TCR interaction. Peptides derived from the WT-1 protein can be used in a vaccine in humans to induce human leukocyte antigen (HLA)-restricted cytotoxic CD8+ T cells that are capable of killing tumor cells. However, because WT-1 is a self-protein, such immunization may only elicit responses by T cells with low affinity TCRs. In addition, antibodies against WT-1 are detectable in patients with hematopoietic malignancies and solid tumors, which show that WT-1 can be a highly immunogenic antigen (Gaiger et al., *Clin. Cancer Res.* 7 (*Suppl.* 3):761, 2001).

Clearly there is a need for alternative TCR gene therapies for use as highly specific, WT-1 targeted immunotherapies directed against various cancers, such as leukemia and tumors. Presently disclosed embodiments address this need and provide other related advantages.

BRIEF SUMMARY

The present disclosure provides, according to certain embodiments, a binding protein (e.g., an immunoglobulin superfamily binding protein, TCR or the like) having (a) an α-chain variable ($V_\alpha$) domain having a CDR1 amino acid sequence shown in SEQ ID NO.:23, a CDR2 amino acid sequence shown in SEQ ID NO.:24 and a CDR3 amino acid sequence shown in any one of SEQ ID NOS.:25, 26, 32, 38, 44, 50 and 51, and/or a β-chain variable ($V_\beta$) domain; or (b) a $V_\alpha$ domain of (a) and a $V_\beta$ domain having a CDR1 amino acid sequence shown in SEQ ID NO.:27, a CDR2 amino acid sequence shown in SEQ ID NO.:28 and/or a CDR3 amino acid sequence shown in SEQ ID NO.:29; wherein the binding protein is capable of binding to a WT1-derived peptide:human leukocyte antigen (HLA) complex with a high affinity, such as a RMFPNAPYL (SEQ ID NO.:16): human leukocyte antigen (HLA) complex, for example, with a $K_d$ less than or equal to about 8 nM.

In certain embodiments the immunoglobulin superfamily binding protein, comprises (a) an α-chain variable ($V_α$) domain having at least 90% sequence identity to an amino acid sequence as set forth in any one of SEQ ID NO.:1 or 2, and/or a β-chain variable ($V_β$) domain; or (b) a $V_α$ domain, and a $V_β$ domain having at least 90% sequence identity to an amino acid sequence as set forth in SEQ ID NO.:9; or (c) a $V_α$ domain of (a) and/or a $V_β$ domain of (b); wherein the binding protein is capable of binding to a RMFPNAPYL (SEQ ID NO.:16):HLA complex with a $K_d$ less than or equal to about 5 nM.

In another aspect there is provided a high affinity recombinant T cell receptor (TCR), comprising an α-chain and a β-chain, wherein the α-chain comprises a $V_α$ domain having at least 90% sequence identity to an amino acid sequence as set forth in SEQ ID NO.:1 or 2, wherein the TCR binds to a RMFPNAPYL (SEQ ID NO.:16)::HLA-A*201 complex independent or in the absence of CD8.

In a further aspect there is provided a method for treating a hyperproliferative disorder, comprising administering to a human subject in need thereof a composition comprising any of the aforementioned binding proteins or high affinity recombinant TCRs specific for human Wilms tumor protein 1 (WT-1). In yet another aspect there is provided an adoptive immunotherapy method for treating a condition characterized by WT-1 overexpression in cells of a subject having a hyperproliferative disorder, comprising administering to the subject an effective amount of a recombinant host cell expressing any of the aforementioned binding proteins or high affinity recombinant TCRs.

In certain embodiments the methods provided are for treating a hyperproliferative disorder that is a hematological malignancy or a solid cancer. For example, the hematological malignancy to be treated may be acute lymphoblastic leukemia (ALL), acute myeloid leukemia (AML), chronic myelogenous leukemia (CML), chronic eosinophilic leukemia (CEL), myelodysplastic syndrome (MDS), non-Hodgkin's lymphoma (NHL), or multiple myeloma (MM). Exemplary solid cancer to be treated may be biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

These and other aspects and embodiments of the herein described invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

DETAILED DESCRIPTION

Figure 1:
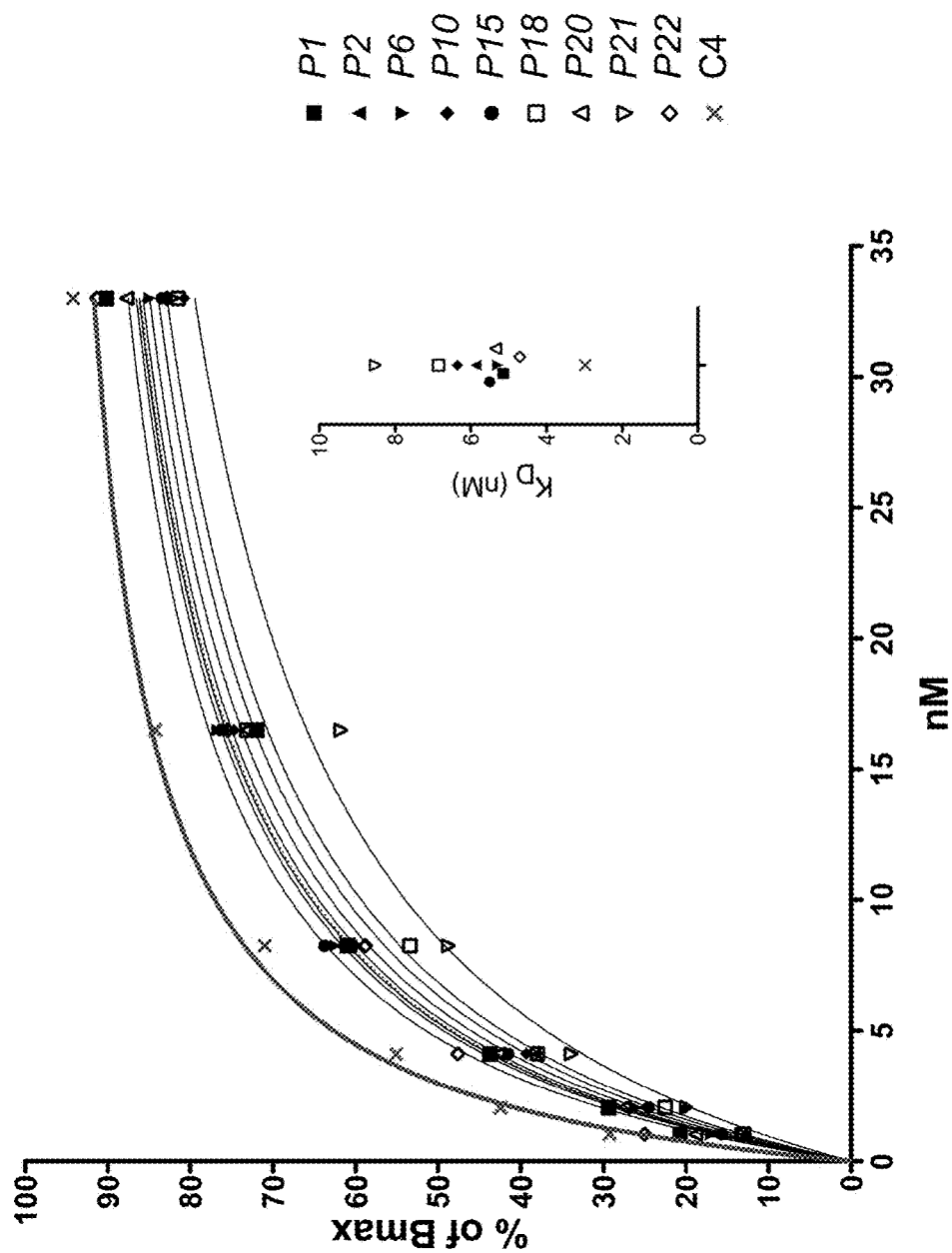
FIG. 1 shows equilibrium binding curves from a titration of WT-1 specific TCRs binding to WT-1 peptide:HLA-A tetramers. T cell clones specific for WT-$1^{126-134}$ (having amino acid sequence RMFPNAPYL, as set forth in SEQ ID NO.:16) were generated from the peripheral repertoire of more than 50 donors, and several candidate high affinity T cell clones were analyzed to determine their relative affinity. Each WT-1-specific T cell clone was stained with WT-$1^{126-134}$ peptide/MHC tetramers ("WT1 tetramers") and analyzed by flow cytometry, and mean fluorescence intensity of tetramer staining was determined using FlowJo software (Treestar). $K_D$ measurements were performed using 2-fold dilutions of PE-conjugated tetramers at a range of concentrations (1-33 nM). Apparent $K_D$ values were determined from binding curves by non-linear regression, as the concentration of ligand that yielded half-maximal binding (Bmax).

In one aspect, the present disclosure provides T cell receptors (TCRs) having high affinity for WT-1 peptide antigen associated with a major histocompatibility complex (MHC) (e.g., human leukocyte antigen, HLA) for use in, for example, adoptive immunotherapy to treat cancer. By way of background, most tumor targets for T cell-based immunotherapies are self-antigens since tumors arise from previously normal tissue. For example, such tumor-associated antigens (TAAs) may be expressed at high levels in a cancer cell, but may not be expressed or may be minimally expressed in other cells. During T cell development in the thymus, T cells that bind weakly to self-antigens are allowed to survive in the thymus, which can undergo further development to increase specificity against foreign invaders, while T cells that bind strongly to self-antigens are eliminated by the immune system since such cells would mount an undesirable autoimmune response. Hence, T cells are sorted by their relative ability to bind to antigens to prepare the immune system to respond against a foreign invader (i.e., recognition of non-self-antigen) while at the same time preventing an autoimmune response (i.e., recognition of self-antigen). This tolerance mechanism limits naturally occurring T cells that can recognize tumor (self) antigens with high affinity and, therefore, eliminates the T cells that would effectively eliminate tumor cells. Consequently, isolating T cells having high affinity TCRs specific for tumor antigens is difficult because such cells are essentially eliminated by the immune system.

An advantage of the instant disclosure is to provide a high affinity or an enhanced affinity TCR specific for a WT-1 peptide, wherein a cell expressing such a TCR is capable of binding to a WT-1::HLA complex independent or in the absence of CD8, is capable of more efficiently associating with a CD3 protein as compared to endogenous TCR, or both. In certain embodiments, an enhanced affinity TCR specific for a WT-1 peptide comprises a T cell receptor (TCR) α-chain as set forth in SEQ ID NO.:7 or 8, and a TCR β-chain variable (V$_\beta$) domain as set forth in SEQ ID NO.:12 or 13, wherein the enhanced affinity TCR is capable of binding to a RMFPNAPYL (SEQ ID NO.:16):HLA complex with a K$_d$ less than or equal to about 3 nM, or wherein the enhanced affinity TCR dissociates from a RMFPNAPYL (SEQ ID NO.:16):HLA complex at a reduced k$_{off}$ rate as compared to a TCR composed of an α-chain of SEQ ID NO.:5 or 6 and a β-chain of SEQ ID NO.:12 or 13.

The compositions and methods described herein will in certain embodiments have therapeutic utility for the treatment of diseases and conditions associated with WT-1 overexpression (e.g., detectable WT-1 expression at a level that is greater in magnitude, in a statistically significant manner, than the level of WT-1 expression that is detectable in a normal or disease-free cell). Such diseases include various forms of hyperproliferative disorders, such as hematological malignancies and solid cancers. Non-limiting examples of these and related uses are described herein and include in vitro, ex vivo and in vivo stimulation of WT-1 antigen-specific T-cell responses, such as by the use of recombinant T cells expressing an enhanced affinity TCR specific for a WT-1 peptide (e.g., RMFPNAPYL, SEQ ID NO.:16).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, meagakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4– CD8– double negative T cell, a γδ T cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

"Major histocompatibility complex" (MHC) refers to glycoproteins that deliver peptide antigens to a cell surface. MHC class I molecules are heterodimers having a membrane spanning α chain (with three α domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by $CD8^+$ T cells. MHC class II molecules deliver peptides originating in the vesicular system to the cell surface, where they are recognized by $CD4^+$ T cells. Human MHC is referred to as human leukocyte antigen (HLA).

A "T cell" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). Effector T cells ($T_E$) refers to antigen-experienced CD8+ cytotoxic T lymphocytes that have decreased expression of CD62L, CCR7, CD28, and are positive for granzyme and perforin as compared to $T_{CM}$. Other exemplary T cells include regulatory T cells, such as CD4+ CD25+ (Foxp3+) regulatory T cells and Treg17 cells, as well as Tr1, Th3, CD8+CD28–, and Qa-1 restricted T cells.

"T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease*, $3^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). Like immunoglobulins, the extracellular portion of TCR chains (e.g., α-chain, β-chain) contain two immunoglobulin domains, a variable domain (e.g., α-chain variable domain or $V_\alpha$, β-chain variable domain or $V_\beta$; typically amino acids 1 to 116 based on Kabat numbering Kabat et al., "Sequences of Proteins of Immunological Interest, US Dept. Health and Human Services, Public Health Service National Institutes of Health, 1991, $5^{th}$ ed.) at the N-terminus, and one constant domain (e.g., α-chain constant domain or $C_\alpha$, typically amino acids 117 to 259 based on Kabat, β-chain constant domain or $C_\beta$, typically amino acids 117 to 295 based on Kabat) adjacent to the cell membrane. Also like immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In certain embodiments, a TCR is found on the surface of T cells (or T lymphocytes) and associates with the CD3 complex. The source of a TCR as used in the present disclosure may be from various animal species, such as a human, mouse, rat, rabbit or other mammal.

"CD3" is known in the art as a multi-protein complex of six chains (see, Abbas and Lichtman, 2003; Janeway et al., p 172 and 178, 1999). In mammals, the complex comprises a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Without wishing to be bound by theory, it is believed the ITAMs are important for the signaling capacity of a TCR complex. CD3 as used in the present disclosure may be from various animal species, including human, mouse, rat, or other mammals.

As used herein, "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

A "binding domain" (also referred to as a "binding region" or "binding moiety"), as used herein, refers to a molecule or portion thereof (e.g., peptide, oligopeptide, polypeptide, protein) that possesses the ability to specifically and non-covalently associate, unite, or combine with a target (e.g., WT-1 or WT-1 peptide:MHC complex). A binding domain includes any naturally occurring, synthetic, semi-synthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv), receptor ectodomains, ligands (e.g., cytokines, chemokines), or synthetic polypeptides selected for their specific ability to bind to a biological molecule, a molecular complex or other target of interest.

As used herein, "specifically binds" or "specific for" refers to an association or union of a binding protein (e.g., TCR receptor) or a binding domain (or fusion protein thereof) to a target molecule with an affinity or $K_a$ (i.e., an equilibrium association constant of a particular binding interaction with units of 1/M) equal to or greater than $10^5$ $M^{-1}$ (which equals the ratio of the on-rate [$k_{on}$] to the off-rate [$k_{off}$] for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$ or at least $10^{13}$ $M^{-1}$. "Low affinity" binding proteins or binding domains refer to those binding proteins or binding domains having a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M).

In certain embodiments, a receptor or binding domain may have "enhanced affinity," which refers to selected or engineered receptors or binding domains with stronger binding to a target antigen than a wild type (or parent) binding domain. For example, enhanced affinity may be due to a $K_a$ (equilibrium association constant) for the target antigen that is higher than the wild type binding domain, due to a $K_d$ (dissociation constant) for the target antigen that is less than that of the wild type binding domain, due to an off-rate ($k_{off}$) for the target antigen that is less than that of the wild type binding domain, or a combination thereof. In certain embodiments, enhanced affinity TCRs may be codon optimized to enhance expression in a particular host cell, such as T cells (Scholten et al., *Clin. Immunol.* 119:135, 2006).

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent).

The term "WT-1-specific binding protein" refers to a protein or polypeptide that specifically binds to WT-1 or peptide thereof. In some embodiments, a protein or polypeptide binds to WT-1 or a peptide thereof, such as a WT-1 peptide in complexed with an MHC or HLA molecule, e.g., on a cell surface, with at or at least about a particular affinity. In certain embodiments, a WT-1-specific binding protein binds a WT-1-derived peptide:HLA complex (or WT-1-derived peptide:MHC complex) with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M, or with an affinity that is about the same as, at least about the same as, or is greater than at or about the affinity exhibited by an exemplary WT-1 specific binding protein provided herein, such as any of the WT-1-specific TCRs provided herein, for example, as measured by the same assay. Assays for assessing affinity or apparent affinity or relative affinity are known. In certain examples, apparent affinity for a TCR is measured by assessing binding to various concentrations of tetramers, for example, by flow cytometry using labeled tetramers. In some examples, apparent $K_D$ of a TCR is measured using 2-fold dilutions of labeled tetramers at a range of concentrations, followed by determination of binding curves by non-linear regression, apparent $K_D$ being determined as the concentration of ligand that yielded half-maximal binding. In certain embodiments, a WT-1-specific binding protein comprises a WT-1-specific immunoglobulin superfamily binding protein or binding portion thereof.

The term "WT-1 binding domain" or "WT-1 binding fragment" refer to a domain or portion of a WT-1-specific binding protein responsible for the specific WT-1 binding. A WT-1-specific binding domain alone (i.e., without any other portion of a WT-1-specific binding protein) can be soluble and can bind to WT-1 with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M. Exemplary WT-1-specific binding domains include WT-1-specific scTCR (e.g., single chain αβTCR proteins such as Vα-L-Vβ, Vβ-L-Vα, Vα-Cα-L-Vα, or Vα-L-Vβ-Cβ, wherein Vα and Vβ are TCRα and β variable domains respectively, Cα and Cβ are TCRα and β constant domains, respectively, and L is a linker) and scFv fragments as described herein, which can be derived from an anti-WT-1 TCR or antibody.

"WT-1 antigen" or "WT-1 peptide antigen" refer to a naturally or synthetically produced portion of a WT-1 protein ranging in length from about 7 amino acids to about 15 amino acids, which can form a complex with a MHC (e.g., HLA) molecule and such a complex can bind with a TCR specific for a WT-1 peptide:MHC (e.g., HLA) complex. Principles of antigen processing by antigen presenting cells (APC) (such as dendritic cells, macrophages, lymphocytes or other cell types), and of antigen presentation by APC to T cells, including major histocompatibility complex (MHC)-restricted presentation between immunocompatible (e.g., sharing at least one allelic form of an MHC gene that is relevant for antigen presentation) APC and T cells, are well established (see, e.g., Murphy, Janeway's Immunobiology ($8^{th}$ Ed.) 2011 Garland Science, NY; chapters 6, 9 and 16). For example, processed antigen peptides originating in the cytosol (e.g., tumor antigen, intrcellular pathogen) are generally from about 7 amino acids to about 11 amino acids in length and will associate with class I MHC molecules, whereas peptides processed in the vesicular system (e.g., bacterial, viral) will vary in length from about 10 amino acids to about 25 amino acids and associate with class II MHC molecules. Since WT-1 is an internal host protein, WT-1 antigen peptides will be presented in the context of class I MHC. In particular embodiments, a WT-1 peptide is RMFPNAPYL (SEQ ID NO.:16), which is known to associate with human class I HLA (and, more specifically, associates with allele HLA-A*201).

A "linker" refers to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In certain embodiments, a linker is comprised of about two to about 35 amino acids, for instance, or about four to about 20 amino acids or about eight to about 15 amino acids or about 15 to about 25 amino acids.

"Junction amino acids" or "junction amino acid residues" refer to one or more (e.g., about 2-10) amino acid residues between two adjacent motifs, regions or domains of a polypeptide, such as between a binding domain and an adjacent constant domain or between a TCR chain and an adjacent self-cleaving peptide. Junction amino acids may result from the construct design of a fusion protein (e.g., amino acid residues resulting from the use of a restriction enzyme site during the construction of a nucleic acid molecule encoding a fusion protein).

An "altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, TCRβ constant domain) of at least 85% (e.g., 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%).

As used herein, "nucleic acid" or "nucleic acid molecule" refers to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

As used herein, the term "recombinant" refers to a cell, microorganism, nucleic acid molecule, or vector that has been modified by introduction of an exogenous nucleic acid molecule, or refers to a cell or microorganism that has been altered such that expression of an endogenous nucleic acid molecule or gene is controlled, deregulated or constitutive, where such alterations or modifications may be introduced by genetic engineering. Genetic alterations may include, for example, modifications introducing nucleic acid molecules (which may include an expression control element, such as a promoter) encoding one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, N.Y, pp. 71-77, 1975; Lewin, Genes IV, Oxford University Press, NY and Cell Press, Cambridge, Mass., p. 8, 1990).

The term "construct" refers to any polynucleotide that contains a recombinant nucleic acid molecule. A construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Exemplary vectors are those capable of autonomous replication (episomal vector) or expression of nucleic acid molecules to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

The term "operably-linked" refers to the association of two or more nucleic acid molecules on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

The term "introduced" in the context of inserting a nucleic acid molecule into a cell, means "transfection", or 'transformation" or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

As used herein, "heterologous" or "exogenous" nucleic acid molecule, construct or sequence refers to a nucleic acid molecule or portion of a nucleic acid molecule that is not native to a host cell, but may be homologous to a nucleic acid molecule or portion of a nucleic acid molecule from the host cell. The source of the heterologous or exogenous nucleic acid molecule, construct or sequence may be from a different genus or species. In certain embodiments, a heterologous or exogenous nucleic acid molecule is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" refers to a non-native enzyme, protein or other activity encoded by an exogenous nucleic acid molecule introduced into the host cell, even if the host cell encodes a homologous protein or activity.

As described herein, more than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a host cell can be modified to express two or more heterologous or exogenous nucleic acid molecules encoding desired TCR specific for a WT-1 antigen peptide (e.g., TCRα and TCRβ). When two or more exogenous nucleic acid molecules are introduced into a host cell, it is understood that the two or more exogenous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

The term "homologous" or "homolog" refers to a molecule or activity found in or derived from a host cell, species or strain. For example, a heterologous or exogenous nucleic acid molecule may be homologous to a native host cell gene, and may optionally have an altered expression level, a different sequence, an altered activity, or any combination thereof.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

As used herein, a "hematopoietic progenitor cell" is a cell that can be derived from hematopoietic stem cells or fetal tissue and is capable of further differentiation into mature cells types (e.g., immune system cells). Exemplary hematopoietic progenitor cells include those with a $CD24^{Lo}Lin^- CD117^+$ phenotype or those found in the thymus (referred to as progenitor thymocytes).

As used herein, the term "host" refers to a cell (e.g., T cell) or microorganism targeted for genetic modification with a heterologous or exogenous nucleic acid molecule to produce a polypeptide of interest (e.g., high or enhanced affinity anti-WT-1 TCR). In certain embodiments, a host cell may optionally already possess or be modified to include other genetic modifications that confer desired properties related or unrelated to biosynthesis of the heterologous or exogenous protein (e.g., inclusion of a detectable marker; deleted, altered or truncated endogenous TCR; increased co-stimulatory factor expression). In certain embodiments, a host cell is a human hematopoietic progenitor cell transduced with a heterologous or exogenous nucleic acid molecule encoding a TCRα chain specific for a WT-1 antigen peptide.

As used herein, "hyperproliferative disorder" refers to excessive growth or proliferation as compared to a normal or undiseased cell. Exemplary hyperproliferative disorders include tumors, cancers, neoplastic tissue, carcinoma, sarcoma, malignant cells, pre-malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like).

Binding Proteins Specific for WT-1 Antigen Peptides

In certain aspects, the instant disclosure provides a binding protein (e.g., an immunoglobulin superfamily binding protein or portion thereof), comprising (a) a T cell receptor (TCR) α-chain variable ($V_\alpha$) domain having a CDR1 amino acid sequence shown in SEQ ID NO.:23, a CDR2 amino acid sequence shown in SEQ ID NO.:24 and a CDR3 amino acid sequence shown in any one of SEQ ID NOS.:25, 26, 32, 38, 44, 50 and 51, and a TCR β-chain variable ($V_\beta$) domain; or (b) a $V_\alpha$ domain of (a) and a $V_\beta$ domain having a CDR1 amino acid sequence shown in SEQ ID NO.:27, a CDR2 amino acid sequence shown in SEQ ID NO.:28 and a CDR3 amino acid sequence shown in SEQ ID NO.:29. Such a binding protein is capable of binding with a high affinity to a WT1-derived peptide:human leukocyte antigen (HLA) complex. In particular embodiments, the binding protein binds to a RMFPNAPYL (SEQ ID NO.:16):human leukocyte antigen (HLA) complex with a $K_d$ less than or equal to about 8 nM.

In certain embodiments, a binding protein (e.g., an immunoglobulin superfamily binding protein or portion thereof) or high affinity recombinant T cell receptor (TCR) specific for WT-1 as described herein includes variant polypeptide species that have one or more amino acid substitutions, insertions, or deletions in the amino acid sequence relative to the sequences of SEQ ID NOS:1-15, 21 and 22 as presented herein, provided that the binding protein retains or substantially retains its specific binding function. Conservative substitutions of amino acids are well known and may occur naturally or may be introduced when the binding protein or TCR is recombinantly produced. Amino acid substitutions, deletions, and additions may be introduced into a protein using mutagenesis methods known in the art (see, e.g., Sambrook et al., *Molecular Cloning: A Laboratory Manual*, 3d ed., Cold Spring Harbor Laboratory Press, N Y, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra).

Species (or variants) of a particular immunoglobulin superfamily binding protein or high affinity recombinant T cell receptor (TCR) specific for WT-1 may include a protein that has at least 85%, 90%, 95%, or 99% amino acid sequence identity to any of the exemplary amino acid sequences disclosed herein (e.g., SEQ ID NOS:1-15, 21 and 22), provided that (a) at least three or four of the CDRs have no mutations, (b) the CDRs that do have mutations have only up to two amino acid substitutions, up to a contiguous five amino acid deletion, or a combination thereof, and (c) the binding protein retains its ability to bind to a RMFP-NAPYL (SEQ ID NO.:16):HLA complex with a $K_d$ less than or equal to about 8 nM.

In other aspects, the present disclosure provides an immunoglobulin superfamily binding protein, comprising (a) a T cell receptor (TCR) α-chain variable ($V_\alpha$) domain having at least 90% sequence identity to an amino acid sequence as set forth in SEQ ID NO.:1 or 2, and a TCR β-chain variable ($V_\beta$) domain; or (b) a $V_\alpha$ domain, and a $V_\beta$ domain having at least 90% sequence identity to an amino acid sequence as set forth in SEQ ID NO.:9; or (c) a $V_\alpha$ domain of (a) and a $V_\beta$ domain of (b); wherein the binding protein is capable of binding to a RMFPNAPYL (SEQ ID NO.:16):HLA complex with a $K_d$ less than or equal to about 5 nM. In certain embodiments, the $V_\alpha$ domain comprises or consists of an amino acid sequence as set forth in SEQ ID NO.:1 or 2, the $V_\beta$ domain comprises or consists of an amino acid sequence as set forth in SEQ ID NO.:9, or a combination thereof.

In further aspects, the present disclosure provides a high affinity recombinant T cell receptor (TCR), comprising an α-chain and a β-chain, wherein the α-chain comprises a $V_\alpha$ domain having at least 90% sequence identity to an amino acid sequence as set forth in SEQ ID NO.:1 or 2, wherein the TCR binds to a RMFPNAPYL (SEQ ID NO.:16)::HLA- A*201 complex on a cell surface independent or in the absence of CD8. In certain embodiments, the $V_\alpha$ domain comprises or consists of an amino acid sequence as set forth in SEQ ID NO.:1 or 2, the $V_\beta$ domain comprises or consists of an amino acid sequence as set forth in SEQ ID NO.:9, or a combination thereof. In certain embodiments, a $V_\beta$ chain is a $V_\beta 17$ allele.

A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine) In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

In certain embodiments, a WT-1 specific binding protein or TCR comprises a $V_\alpha$ domain that is at least about 90% identical to an amino acid sequence as set forth in SEQ ID NO.:21 or 22, and comprises a $V_\beta$ domain that is at least about 90% identical to the amino acid sequence as set forth in SEQ ID NO:9, provided that (a) at least three or four of the CDRs have no mutations and (b) the CDRs that do have mutations have only up to two amino acid substitutions, up to a contiguous five amino acid deletion, or a combination thereof. In further embodiments, a WT-1 specific binding protein or TCR comprises a $V_\alpha$ domain that is at least about 95% identical to an amino acid sequence as set forth in SEQ ID NO.:1 or 2, and comprises a $V_\beta$ domain that is at least about 95% identical to the amino acid sequence as set forth in SEQ ID NO.:9, provided that the binding protein is capable of binding to a RMFPNAPYL (SEQ ID NO.:16): HLA complex with a $K_d$ less than or equal to about 5 nM.

In any of the aforementioned embodiments, a WT-1 specific binding protein or TCR is capable of (a) specifically binding to a RMFPNAPYL (SEQ ID NO.:16):HLA complex on a cell surface independent or in the absence of CD8, (b) specifically binding to a RMFPNAPYL (SEQ ID NO.:16): HLA-A*201 complex, (c) binding to the RMFPNAPYL (SEQ ID NO.:16):HLA-A*201 complex with a $K_d$ less than or equal to about 3 nM, or (d) any combination thereof.

In certain embodiments, the $V_\alpha$ domain of a WT-1 specific binding protein or TCR comprises or consists of an amino acid sequence as set forth in SEQ ID NO.:1 or 2. In other embodiments, the $V_\beta$ domain comprises or consists of an amino acid sequence as set forth in SEQ ID NO.:9.

In still further embodiments, a WT-1 specific binding protein or TCR comprises an $\alpha$-chain constant domain having at least 90% sequence identity to an amino acid sequence as set forth in SEQ ID NO.:3 or 4, comprises a $\beta$-chain constant domain having at least 90% sequence identity to an amino acid sequence as set forth in SEQ ID NO.:10 or 11, or any combination thereof. In certain embodiments, a $V_\beta$ chain is a $V_\beta 17$ allele.

In certain embodiments, a WT-1 specific binding protein is a T cell receptor (TCR), a chimeric antigen receptor or an antigen-binding fragment of a TCR, any of which can be chimeric, humanized or human. In further embodiments, an antigen-binding fragment of the TCR comprises a single chain TCR (scTCR) or a chimeric antigen receptor (CAR). In certain embodiments, a WT-1 specific binding protein is a TCR. In related embodiments, a WT-1 specific binding protein (a) comprises a TCR $\alpha$-chain having an amino acid sequence as set forth in any one of SEQ ID NOS.:5-8, and comprises a TCR $\beta$-chain having an amino acid sequence as set forth in SEQ ID NO.:12 or 13; (b) has a TCR $\alpha$-chain that comprises or consists of an amino acid sequence as set forth in SEQ ID NO.:5, and the TCR $\beta$-chain comprises or consists of an amino acid sequence as set forth in SEQ ID NO.:12; (c) has a TCR $\alpha$-chain comprises or consists of an amino acid sequence as set forth in SEQ ID NO.:7, and the TCR $\beta$-chain comprises or consists of an amino acid sequence as set forth in SEQ ID NO.:12; (d) has a TCR $\alpha$-chain comprises or consists of an amino acid sequence as set forth in SEQ ID NO.:6, and the TCR $\beta$-chain comprises or consists of an amino acid sequence as set forth in SEQ ID NO.:13; or (e) has a TCR $\alpha$-chain comprises or consists of an amino acid sequence as set forth in SEQ ID NO.:8, and the TCR $\beta$-chain comprises or consists of an amino acid sequence as set forth in SEQ ID NO.:13.

In certain embodiments, there is provided a composition comprising a WT-specific binding protein or high affinity recombinant TCR according to any one of the aforementioned embodiments and a pharmaceutically acceptable carrier, diluent, or excipient.

Methods useful for isolating and purifying recombinantly produced soluble TCR, by way of example, may include obtaining supernatants from suitable host cell/vector systems that secrete the recombinant soluble TCR into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant soluble TCR described herein include batch cell culture, which is monitored and controlled to maintain appropriate culture conditions. Purification of the soluble TCR may be performed according to methods described herein and known in the art and that comport with laws and guidelines of domestic and foreign regulatory agencies.

In certain embodiments, nucleic acid molecules encoding an immunoglobulin superfamily binding protein or enhanced affinity TCR specific for WT-1 are used to transfect/transduce a host cell (e.g., T cells) for use in adoptive transfer therapy. Advances in TCR sequencing have been described (e.g., Robins et al., 2009 *Blood* 114:4099; Robins et al., 2010 *Sci. Translat. Med.* 2:47ra64, PMID: 20811043; Robins et al. 2011 (September 10) *J. Imm. Meth.* Epub ahead of print, PMID: 21945395; Warren et al., 2011 *Genome Res.* 21:790) and may be employed in the course of practicing the embodiments according to the present disclosure. Similarly, methods for transfecting/transducing T-cells with desired nucleic acids have been described (e.g., US 2004/0087025) as have adoptive transfer procedures using T-cells of desired antigen-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US2011/0189141; Leen et al., *Ann. Rev. Immunol.* 25:243, 2007), such that adaptation of these methodologies to the presently disclosed embodiments is contemplated, based on the teachings herein, including those directed to enhanced affinity TCRs specific for WT-1 peptide antigen RMFPNAPYL (SEQ ID NO.:16) complexed with an HLA receptor.

The WT-1-specific binding proteins or domains as described herein (e.g., SEQ ID NOS:1-15 and 21-31, and variants thereof), may be functionally characterized according to any of a large number of art accepted methodologies for assaying T cell activity, including determination of T cell binding, activation or induction and also including determination of T cell responses that are antigen-specific. Examples include determination of T cell proliferation, T cell cytokine release, antigen-specific T cell stimulation, MHC restricted T cell stimulation, CTL activity (e.g., by detecting $^{51}$Cr release from pre-loaded target cells), changes in T cell phenotypic marker expression, and other measures of T-cell functions. Procedures for performing these and similar assays are may be found, for example, in Lefkovits (*Immunology Methods Manual: The Comprehensive Sourcebook of Techniques*, 1998). See also *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998) and references cited therein).

"MHC-peptide tetramer staining" refers to an assay used to detect antigen-specific T cells, which features a tetramer of MHC molecules, each comprising an identical peptide having an amino acid sequence that is cognate (e.g., identical or related to) at least one antigen (e.g., WT-1), wherein the complex is capable of binding T cell receptors specific for the cognate antigen. Each of the MHC molecules may be tagged with a biotin molecule. Biotinylated MHC/peptides are tetramerized by the addition of streptavidin, which can be fluorescently labeled. The tetramer may be detected by flow cytometry via the fluorescent label. In certain embodiments, an MHC-peptide tetramer assay is used to detect or select enhanced affinity TCRs of the instant disclosure.

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

Polynucleotides Encoding Binding Proteins Specific for WT-1 Antigen Peptides

Isolated or recombinant nucleic acid molecules encoding immunoglobulin superfamily binding protein or high affinity recombinant T cell receptor (TCR) specific for WT-1 as described herein may be produced and prepared according to various methods and techniques of the molecular biology or polypeptide purification arts. Construction of an expression vector that is used for recombinantly producing an immunoglobulin superfamily binding protein or high affinity recombinant TCR specific for WT-1 of interest can be accomplished by using any suitable molecular biology engineering techniques known in the art, including the use of restriction endonuclease digestion, ligation, transformation, plasmid purification, and DNA sequencing, for example as described in Sambrook et al. (1989 and 2001 editions; *Molecular Cloning: A Laboratory Manual*, Cold Spring Harbor Laboratory Press, NY) and Ausubel et al. (Current Protocols in Molecular Biology (2003)). To obtain efficient transcription and translation, a polynucleotide in each recombinant expression construct includes at least one appropriate expression control sequence (also called a regulatory sequence), such as a leader sequence and particularly a promoter operably (i.e., operatively) linked to the nucleotide sequence encoding the immunogen. In certain embodiments, a polynucleotide is codon optimized for efficient expression in a target host cell.

Certain embodiments relate to nucleic acids that encode the polypeptides contemplated herein, for instance, immunoglobulin superfamily binding proteins or high affinity recombinant TCRs specific for WT-1. In particular embodiments, the instant disclosure provides an isolated polynucleotide encoding a binding protein, including a polynucleotide that encodes an α-chain variable ($V_\alpha$) domain having the complementarity determining region 3 (CDR3) amino acid sequence set forth in SEQ ID NO.:25 or 26, wherein the polynucleotide encoding the $V_\alpha$ domain is at least 80% identical to the nucleotide sequence of SEQ ID NO.:78, 128, or 80; and a polynucleotide that encodes a (β-chain variable ($V_\beta$) domain having the CDR3 amino acid sequence set forth in SEQ ID NO.:29, wherein the polynucleotide encoding the $V_\beta$domain is at least 80% identical to the nucleotide sequence of SEQ ID NO.:89. In some embodiments, a polynucleotide of the present disclosure encodes a self-cleaving peptide disposed between the $V_\alpha$ domain encoding polynucleotide and the $V_\beta$ domain encoding polynucleotide. In certain embodiments, the polynucleotide comprises, or consists of, the nucleotide sequence of SEQ ID NO:96. In certain embodiments, the polynucleotide comprises or consists of the nucleotide sequence of SEQ ID NO.:97. As one of skill in the art will recognize, a nucleic acid may refer to a single- or a double-stranded DNA, cDNA or RNA in any form, and may include a positive and a negative strand of the nucleic acid which complement each other, including antisense DNA, cDNA and RNA. Also included are siRNA, microRNA, RNA-DNA hybrids, ribozymes, and other various naturally occurring or synthetic forms of DNA or RNA.

Standard techniques may be used for recombinant DNA, peptide and oligonucleotide synthesis, immunoassays and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well-known in the art and as described in various general and more specific references in microbiology, molecular biology, biochemistry, molecular genetics, cell biology, virology and immunology techniques that are cited and discussed throughout the present specification. See, e.g., Sambrook, et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, DNA Cloning: A Practical Approach, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); Animal Cell Culture (R. Freshney, Ed., 1986); Perbal, *A Practical Guide to Molecular Cloning* (1984); *Next-Generation Genome Sequencing* (Janitz, 2008 Wiley-VCH); *PCR Protocols* (Methods in Molecular Biology) (Park, Ed., 3$^{rd}$ Edition, 2010 Humana Press); *Immobilized Cells And Enzymes* (IRL Press, 1986); the treatise, Methods In Enzymology (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N. Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Roitt, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Certain embodiments include nucleic acids contained in a vector. One of skill in the art can readily ascertain suitable vectors for use with certain embodiments disclosed herein. A typical vector may comprise a nucleic acid molecule capable of transporting another nucleic acid to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell upon introduction into the host cell and thereby replicate along with the host genome. Additionally, some vectors are capable of directing the expression of genes to which they are operatively linked (these vectors may be referred to as "expression vectors"). According to related embodiments, it is further understood that, if one or more agents (e.g., polynucleotides encoding immunoglobulin superfamily binding proteins or high affinity recombinant TCRs specific for WT-1, or variants thereof, as described herein) is co-administered to a subject, that each agent may reside in separate or the same vectors, and multiple vectors (each containing a different agent the same agent) may be introduced to a cell or cell population or administered to a subject.

In certain embodiments, the nucleic acid encoding immunoglobulin superfamily binding proteins or high affinity recombinant TCRs specific for WT-1, may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e. Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

In particular embodiments, the recombinant expression vector is delivered to an appropriate cell, for example, a T cell or an antigen-presenting cell, i.e., a cell that displays a peptide/MHC complex on its cell surface (e.g., a dendritic cell) and lacks CD8. The recombinant expression vectors may therefore also include, for example, lymphoid tissue-specific transcriptional regulatory elements (TRE) such as a B lymphocyte, T lymphocyte, or dendritic cell specific TRE. Lymphoid tissue specific TRE are known in the art (see, e.g., Thompson et al., *Mol. Cell. Biol.* 12:1043, 1992); Todd et al., *J. Exp. Med.* 177:1663, 1993); Penix et al., *J. Exp. Med.* 178:1483, 1993).

In addition to vectors, certain embodiments relate to host cells that comprise the vectors that are presently disclosed. One of skill in the art readily understands that many suitable host cells are available in the art. A host cell may include any individual cell or cell culture which may receive a vector or the incorporation of nucleic acids and/or proteins, as well as any progeny cells. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. For example, see Sambrook et al., *Molecular Cloning: A Laboratory Manual* 2d ed. (Cold Spring Harbor Laboratory, 1989).

Methods of Treatment

In certain aspects, the instant disclosure is directed to methods for treating a hyperproliferative disorder or a condition characterized by WT-1 overexpression by administering to human subject in need thereof a composition comprising a binding protein or high affinity recombinant TCR specific for human Wilms tumor protein 1 (WT-1) according to any the aforementioned binding proteins or TCRs.

The presence of a hyperproliferative disorder or malignant condition in a subject refers to the presence of dysplastic, cancerous and/or transformed cells in the subject, including, for example neoplastic, tumor, non-contact inhibited or oncogenically transformed cells, or the like (e.g., solid cancers; hematologic cancers including lymphomas and leukemias, such as acute myeloid leukemia, chronic myeloid leukemia, etc.), which are known in the art and for which criteria for diagnosis and classification are established (e.g., Hanahan and Weinberg, 2011 *Cell* 144:646; Hanahan and Weinberg 2000 *Cell* 100:57; Cavallo et al., 2011 *Canc. Immunol. Immunother.* 60:319; Kyrigideis et al., 2010 *J. Carcinog.* 9:3). In certain embodiments, such cancer cells may be cells of acute myeloid leukemia, B-cell lymphoblastic leukemia, T-cell lymphoblastic leukemia, or myeloma, including cancer stem cells that are capable of initiating and serially transplanting any of these types of cancer (see, e.g., Park et al. 2009 *Molec. Therap.* 17:219).

In certain embodiments, there are provided methods for treating a hyperproliferative disorder, such as a hematological malignancy or a solid cancer. Exemplary hematological malignancies include acute lymphoblastic leukemia (ALL), acute myeloid leukemia (AML), chronic myelogenous leukemia (CML), chronic eosinophilic leukemia (CEL), myelodysplastic syndrome (MDS), non-Hodgkin's lymphoma (NHL), or multiple myeloma (MM).

In further embodiments, there are provided methods for treating a hyperproliferative disorder, such as a solid cancer is selected from biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

As understood by a person skilled in the medical art, the terms, "treat" and "treatment," refer to medical management of a disease, disorder, or condition of a subject (i.e., patient, host, who may be a human or non-human animal) (see, e.g., Stedman's Medical Dictionary). In general, an appropriate dose and treatment regimen provide one or more of a binding protein or high affinity recombinant TCR specific for human WT-1 (e.g., SEQ ID NOS:1-15 and 21-31, and variants thereof) or a host cell expressing the same, and optionally an adjunctive therapy (e.g., a cytokine such as IL-2, IL-15, IL-21 or any combination thereof), in an amount sufficient to provide therapeutic or prophylactic benefit. Therapeutic or prophylactic benefit resulting from therapeutic treatment or prophylactic or preventative methods include, for example an improved clinical outcome, wherein the object is to prevent or retard or otherwise reduce (e.g., decrease in a statistically significant manner relative to an untreated control) an undesired physiological change or disorder, or to prevent, retard or otherwise reduce the expansion or severity of such a disease or disorder. Beneficial or desired clinical results from treating a subject include abatement, lessening, or alleviation of symptoms that result from or are associated the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; or overall survival.

"Treatment" can also mean prolonging survival when compared to expected survival if a subject were not receiving treatment. Subjects in need of the methods and compositions described herein include those who already have the disease or disorder, as well as subjects prone to have or at risk of developing the disease or disorder. Subjects in need of prophylactic treatment include subjects in whom the disease, condition, or disorder is to be prevented (i.e., decreasing the likelihood of occurrence or recurrence of the disease or disorder). The clinical benefit provided by the compositions (and preparations comprising the compositions) and methods described herein can be evaluated by design and execution of in vitro assays, preclinical studies, and clinical studies in subjects to whom administration of the compositions is intended to benefit, as described in the examples.

Cells expressing the binding protein or high affinity recombinant TCR specific for human WT-1 as described herein may be administered to a subject in a pharmaceutically or physiologically acceptable or suitable excipient or carrier. Pharmaceutically acceptable excipients are biologically compatible vehicles, e.g., physiological saline, which are described in greater detail herein, that are suitable for administration to a human or other non-human mammalian subject.

A therapeutically effective dose is an amount of host cells (expressing a binding protein or high affinity recombinant TCR specific for human WT-1) used in adoptive transfer that is capable of producing a clinically desirable result (i.e., a sufficient amount to induce or enhance a specific T cell immune response against cells overexpressing WT-1 (e.g., a cytotoxic T cell response) in a statistically significant manner) in a treated human or non-human mammal. As is well known in the medical arts, the dosage for any one patient depends upon many factors, including the patient's size, weight, body surface area, age, the particular therapy to be administered, sex, time and route of administration, general health, and other drugs being administered concurrently. Doses will vary, but a preferred dose for administration of a host cell comprising a recombinant expression vector as described herein is about $10^7$ cells/m$^2$, about $5 \times 10^7$ cells/m$^2$, about $10^8$ cells/m$^2$, about $5 \times 10^8$ cells/m$^2$, about $10^9$ cells/m$^2$, about $5 \times 10^9$ cells/m$^2$, about $10^{10}$ cells/m$^2$, about $5 \times 10^{10}$ cells/m$^2$, or about $10^{11}$ cells/m$^2$.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's disease, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

A condition associated with WT-1 overexpression includes any disorder or condition in which underactivity, overactivity or improper activity of a WT-1 cellular or molecular event is present, and typically results from unusually high (with statistical significance) levels of WT-1 expression in afflicted cells (e.g., leukemic cells), relative to normal cells. A subject having such a disorder or condition would benefit from treatment with a composition or method of the presently described embodiments. Some conditions associated with WT-1 overexpression thus may include acute as well as chronic disorders and diseases, such as those pathological conditions that predispose the subject to a particular disorder.

Some examples of conditions associated with WT-1 overexpression include hyperproliferative disorders, which refer to states of activated and/or proliferating cells (which may also be transcriptionally overactive) in a subject including tumors, neoplasms, cancer, malignancy, etc. In addition to activated or proliferating cells, the hyperproliferative disorder may also include an aberration or dysregulation of cell death processes, whether by necrosis or apoptosis. Such aberration of cell death processes may be associated with a variety of conditions, including cancer (including primary, secondary malignancies as well as metastasis), or other conditions.

According to certain embodiments, virtually any type of cancer that is characterized by WT-1 overexpression may be treated through the use of compositions and methods disclosed herein, including hematological cancers (e.g., leukemia including acute myeloid leukemia (AML), T or B cell lymphomas, myeloma, and others). Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer. Also contemplated within the presently disclosed embodiments are specific embodiments wherein only one of the above types of disease is included, or where specific conditions may be excluded regardless of whether or not they are characterized by WT-1 overexpression.

Certain methods of treatment or prevention contemplated herein include administering a host cell (which may be autologous, allogeneic or syngeneic) comprising a desired nucleic acid molecule as described herein that is stably integrated into the chromosome of the cell. For example, such a cellular composition may be generated ex vivo using autologous, allogeneic or syngeneic immune system cells (e.g., T cells, antigen-presenting cells, natural killer cells) in order to administer a desired, WT-1-targeted T-cell composition to a subject as an adoptive immunotherapy.

As used herein, administration of a composition or therapy refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., WT-1 specific recombinant host cells with one or more cytokines; immunosuppressive therapy such as calcineurin inhibitors, corticosteroids, microtubule inhibitors, low dose of a mycophenolic acid prodrug, or any combination thereof).

In certain embodiments, a plurality of doses of a recombinant host cell as described herein is administered to the subject, which may be administered at intervals between administrations of about two to about four weeks. In further embodiments, a cytokine is administered sequentially, provided that the subject was administered the recombinant host cell at least three or four times before cytokine administration. In certain embodiments, the cytokine is administered subcutaneously (e.g., IL-2, IL-15, IL-21). In still further embodiments, the subject being treated is further receiving immunosuppressive therapy, such as calcineurin inhibitors, corticosteroids, microtubule inhibitors, low dose of a mycophenolic acid prodrug, or any combination thereof. In yet further embodiments, the subject being treated has received a non-myeloablative or a myeloablative hematopoietic cell transplant, wherein the treatment may be administered at least two to at least three months after the non-myeloablative hematopoietic cell transplant.

An effective amount of a therapeutic or pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

The level of a CTL immune response may be determined by any one of numerous immunological methods described herein and routinely practiced in the art. The level of a CTL immune response may be determined prior to and following administration of any one of the herein described WT-1-specific binding proteins expressed by, for example, a T cell. Cytotoxicity assays for determining CTL activity may be performed using any one of several techniques and methods routinely practiced in the art (see, e.g., Henkart et al., "Cytotoxic T-Lymphocytes" in *Fundamental Immunology*, Paul (ed.) (2003 Lippincott Williams & Wilkins, Philadelphia, Pa.), pages 1127-50, and references cited therein).

Antigen-specific T cell responses are typically determined by comparisons of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen used to prime or activate the T cells, when presented by immunocompatible antigen-presenting cells) and T cells from the same source population that are exposed instead to a structurally distinct or irrelevant control antigen. A response to the cognate antigen that is greater, with statistical significance, than the response to the control antigen signifies antigen-specificity.

A biological sample may be obtained from a subject for determining the presence and level of an immune response to a WT-1-derived antigen peptide as described herein. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

The pharmaceutical compositions described herein may be presented in unit-dose or multi-dose containers, such as sealed ampoules or vials. Such containers may be frozen to preserve the stability of the formulation until. In certain embodiments, a unit dose comprises a recombinant host cell as described herein at a dose of about $10^7$ cells/m$^2$ to about $10^{11}$ cells/m$^2$. The development of suitable dosing and treatment regimens for using the particular compositions described herein in a variety of treatment regimens, including e.g., parenteral or intravenous administration or formulation.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of recombinant cells or active compound calculated to produce the desired therapeutic effect in association with an appropriate pharmaceutical carrier.

In general, an appropriate dosage and treatment regimen provides the active molecules or cells in an amount sufficient to provide therapeutic or prophylactic benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine in the art and may be performed using samples obtained from a subject before and after treatment.

EXAMPLES

Example 1

Methods

Lentiviral Constructs

Various TCR expression constructs were generated containing codon-optimized TCRα and TCRβ genes, derived from an HLA-A2-restricted CD8$^{+\ T\ cell\ clone}$ (C4), encoding a high affinity TCR specific for a WT-1 peptide RMFP-NAPYL (SEQ ID NO.:16) complexed with an HLA receptor. The TCRα- and TCRβ-encoding nucleic acid molecules were linked by a 2A element from the porcine teschovirus (P2A) to ensure coordinated expression under the control of a murine stem cell virus (MSCV) U3 promoter. In certain embodiments, the portions of the nucleic acid molecules encoding the constant domains of the C4 TCRα and TCRβ were modified to express complementary cysteine residues at positions 48 (Thr to Cys) and 57 (Ser to Cys), respectively, to promote inter-chain pairing of the C4 TCR chains and to minimize mispairing of the exogenous C4 TCR chains with endogenous TCR chains.

The vector pRRLSIN-C4α-P2A-C4β contained the TCR expression construct ligated into the pRRLSIN.cPPT.MSCV/GFP.WPRE lentiviral vector between the AscI and SalI restriction endonuclease sites, replacing GFP. The pRRLSIN.cPPT.MSCV/GFP.WPRE plasmid is a third-generation, self-inactivating lentiviral vector (see Yang et al., *J. Immunother.* 31:830, 2008).

Saturation Mutagenesis Libraries

Two saturation mutagenesis libraries were constructed to generate and identify mutations within the C4α CDR regions (particularly the CDR3) that resulted in a higher or enhanced affinity for HLA-A2/WT-1 complex. The CDR3 region of C4α is comprised of the following amino acids: CAATEDYQLIW (SEQ ID NO.:25). Two randomized libraries were constructed encompassing residues ATE and DYQ using the Quikchange II site-directed mutagenesis kit (Agilent), using the lentiviral vector pRRLSIN-C4α-P2A-β as a template. Mutagenesis primers were designed according to the modified Quikchange protocol described by Zheng et al. (*Nucleic Acids Res.* 32:e115, 2004), and incorporated randomized nucleotides NNK (where N=A, C, G, or T, and K=G or T) for each amino acid position to be randomized. This yielded 32 different codons, encoding all 20 amino acids, and one stop codon. High transformation efficiency (greater than 1×10$^{10}$) Electromax DH10B T1 cells were transformed with the mutagenesis reaction composition, and the number of independent clones was determined by titrating and culturing a fraction of the transformation reaction on LB-Ampicillin plates. After determining the total number of clones, the transformation mix was plated on LB-Ampicillin plates at about 5,000 clones per plate. After 18 hours of culture at 37° C., 0.5-1 mL LB was added to the library plates and all colonies were harvested together, centrifuged, and high quality plasmid library DNA was isolated using the Endofree plasmid Maxi kit (Qiagen).

The library size was estimated to include about 100,000 independent clones, which was estimated to result in a library that was about 95% complete. To measure the efficiency of the mutagenesis reaction and the diversity of the library, the combined library plasmid DNA was sequenced, and the proportion of each nucleotide at each of the randomized positions was determined to be equivalent by comparing the relative signal for each nucleotide on a sequencing chromatogram (data not shown).

Screening of Saturation Mutagenesis Libraries

For each library, lentivirus was generated by transducing three plates of 293T cells (about 7×10⁶ cells/plate) with the high quality plasmid library, concomitantly with the three packaging vectors pMDLg/pRRE, pMD2-G, and pRSV-REV. After 2 days, supernatant from the three plates were combined and aliquots were frozen for future use.

The lentiviral supernatant was titrated to determine the optimal concentration to utilize for transductions in order to minimize the probability that target cells are transduced with more than one library-derived TCR. Total transduction efficiency was determined by analyzing the percentage of cells expressing the transgenic beta chain (Vβ17). A dilution that yielded about a 20% transduction rate was chosen, and used to transduce about 2-5×10⁷ J.RT3 cells. Library transduced cells were sorted by flow cytometry for high levels of WT-1 tetramer staining in the presence or absence of 1 µg/ml of competing anti-MHC class I antibody and expanded in culture multiple times. Sorted populations that bound WT-1 tetramer at higher levels than J.RT3 cells transduced with the parental C4α-P2A-C4β construct were lysed, and genomic DNA was isolated using a DNeasy kit (Qiagen). The isolated DNA was used for PCR amplification of the lentiviral insert using primers that flank the TCR expression construct and that yielded a single band of the corresponding size. The PCR product was cloned into pENTR-D-Topo (Invitrogen), and clones were characterized by DNA sequence analysis.

Following sequence analysis of the isolated clones, a 750 bp AscI-BamHI fragment containing the C4α CDR3 region was excised from candidate clones and ligated into the parental pRRLSIN-C4α-P2A-C4β vector. Candidate mutants were then transduced into J.RT3 cells and PBMCs alongside the parental C4 construct, and mutants were assessed for binding affinity to HLA-A2/WT-1$^{126-134}$ (RMF-PNAPYL, SEQ ID NO.:16).

Relative Affinity by Tetramer Titration

T cell clones were stained with 2-fold serial dilutions of WT-1 tetramer and analyzed by flow cytometry. Statistical analysis was performed in Graphpad Prism. KD values were extrapolated using a non-linear regression algorithm to a saturation binding curve with the formula $Y=B_{max}*X/[K_D+X]$.

Example 2

Identification and Cloning of High Affinity WT-1-Specific TCRs

In order to identify high affinity HLA-A2-restricted WT-1$^{126-134}$-specific T cell clones, T cell clones were generated from the peripheral repertoire of more than 50 donors. The top ten clones that exhibited the highest apparent affinity by tetramer staining were further assessed by staining each clone with titrated concentrations of WT-1 tetramer and fitting the resulting mean fluorescence intensity data to a saturation binding curve (FIG. 1). TCRα and TCRβ gene sequences were identified by RACE PCR and sequencing of the four clones with the highest relative affinity was performed (C4, P1, P20, and P22).

To further characterize the WT-1$^{126-134}$-specific TCRs from these candidate T cell clones, codon-optimized expression constructs were generated for each TCRα and TCRβ chain pair. For each construct, the α and β chains were separated by a P2A element to promote coordinated expression of the TCRα and TCRβ chains (see, e.g., Szymczak et al., Nat. Biotechnol. 22:589, 2004; Dossett et al., Mol. Ther. 17:742, 2009). In addition, point mutations to create a second pair of cysteine residues in the external membrane-proximal regions of TCRα and TCRβ constant domains were introduced to promote preferential pairing of introduced TCR chains (Kuball et al., Blood 109:2331, 2007). Finally, these codon-optimized, cysteine-modified constructs were cloned into the lentiviral vector pRRLSIN-.cPPT-MSCV.WPRE (see FIG. 3C).

Figure 2A:
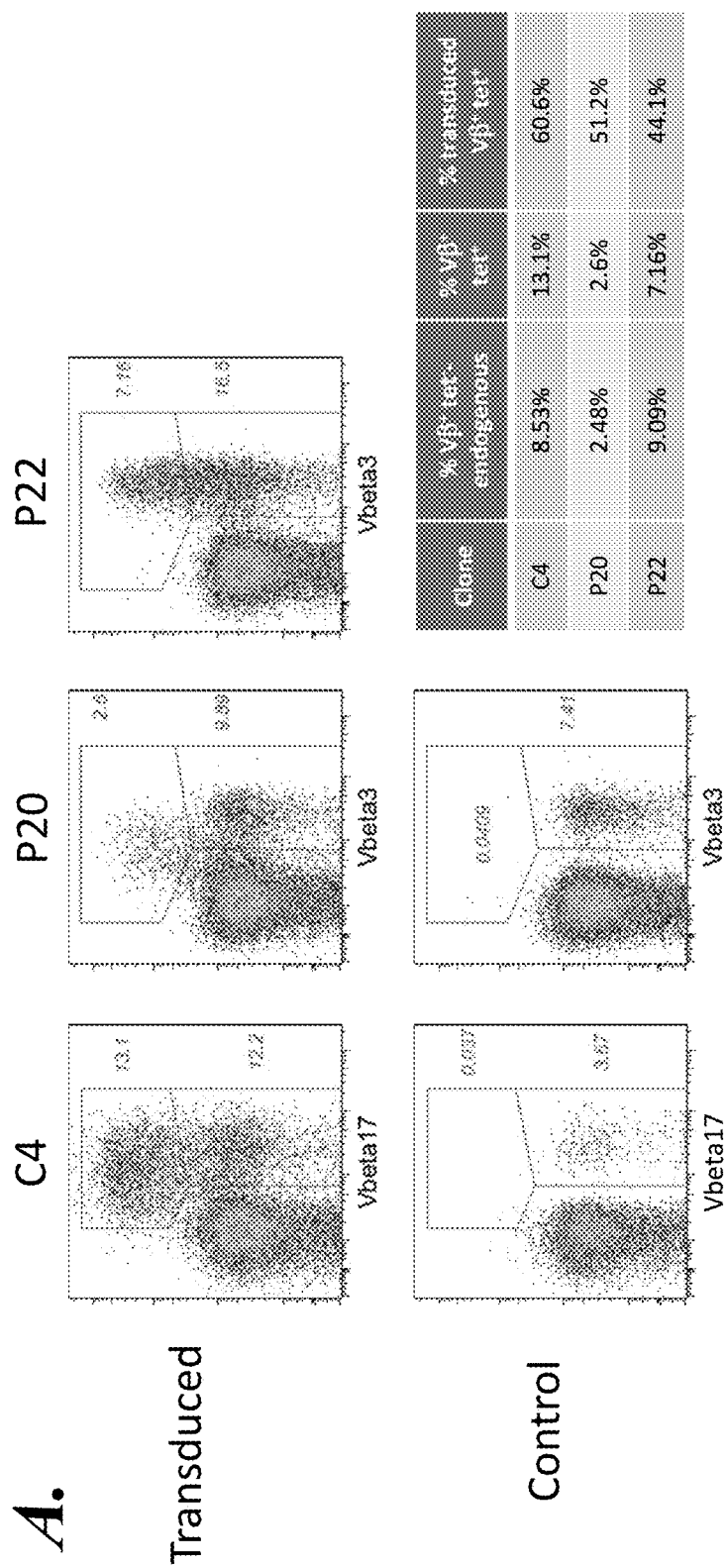
FIGS. 2A and 2B show that assessed high affinity TCR clones could efficiently outcompete endogenous TCR chains and bind WT-$1^{126-134}$ tetramers independently of CD8. Codon-optimized TCRα-P2A-β constructs were generated containing the TCRα and TCRβ chains from the three TCRs generated from the peripheral repertoires having the highest affinity for this WT-1 epitope (C4, P1, P22). (A) These constructs were transduced into PBMCs and the percentage of WT-$1^{126-134}$ tetramer staining cells within the transduced cell population was assessed by flow cytometry, with tetramer staining represented on the Y-axis and the respective transgenic β-chain staining represented on the X-axis. The transduced population was calculated as the total percentage of cells expressing the transgenic TCRβ chain minus the percentage of T cells endogenously expressing that TCRβ chain in an untransduced culture of the same PBMCs. (B) Tetramer binding by the different TCRs in the absence of CD8 was assessed by measuring WT-1 tetramer staining on transduced CD4$^+$ cells (CD8 negative, CD8$^-$) versus CD8$^+$ cells within the transduced population of PBMCs. One of the TCR clones, C4, exhibited the highest degree of tetramer binding on CD4$^+$CD8$^-$ cells

Next, the ability of each of the introduced TCRαβ pairs to out-compete endogenous TCR chains for association with CD3 components and expression on the T cell surface was examined (see, e.g., Heemskerk et al., Blood 109:235, 2007). The codon-optimized, cysteine-modified TCR$_{C4}$, TCR$_{P20}$ and TCR$_{P22}$ were transduced into PBMCs and the percentage of tetramer positive cells within the transduced CD8⁺ T cell population was determined (FIG. 2A). The total transduced population was determined by subtracting the percentage of endogenous Vβ chain expression in the untransduced control from the percentage of TCR Vβ-specific T cells in the transduced populations (FIG. 2A).

Figure 2B:
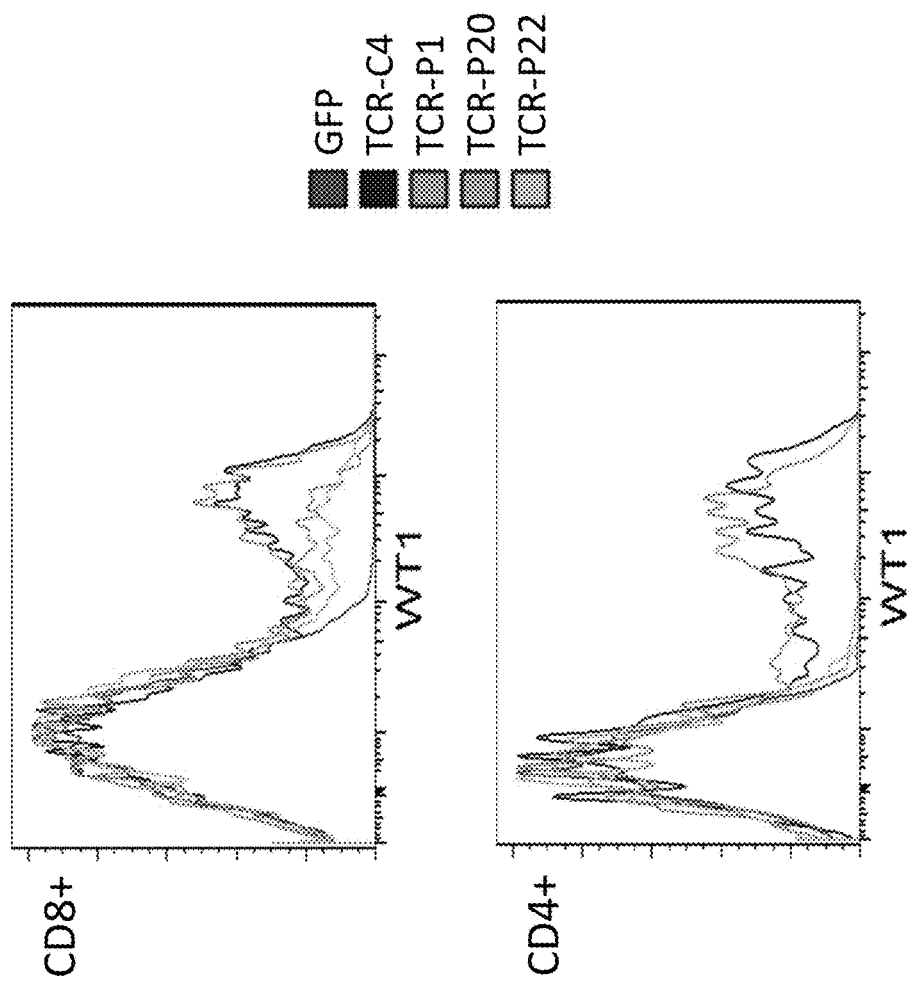

To determine the ability of each TCR to bind tetramer independently of CD8, which is associated with high affinity for peptide/MHC, transduced PBMCs were gated on CD4⁺ T cells and WT-1 tetramer staining was assessed (FIG. 2B). Both the TCR$_{C4}$ and TCR$_{P1}$ clones bound tetramer independently of CD8. Furthermore, TCR$_{C4}$ exhibited the highest levels of CD8-independent tetramer staining, and PBMCs transduced with the TCR$_{C4}$ construct exhibited the highest percentage of WT-1 tetramer positive T cells. The codon-optimized, cysteine-modified TCR$_{C4}$ clone, which also exhibited the highest relative affinity among all the clones studied, was selected for modification and functional studies.

Example 3

Improving the High Affinity WT-1-Specific TCR$_{C4}$ Construct

As described in Example 2, the wild-type (WT) TCR$_{C4}$ expression construct (C4αβ WT) was generated from full-length TCRα and TCRβ produced by 5'-RACE PCR from the TCR$_{C4}$ clone. This construct included the nucleic acid encoding the C4 TCRα chain in the 5'-position, followed by a P2A element, and then the nucleic acid encoding the C4 TCRβ chain. Although T cells expressing this construct expressed similar levels of transgenic Vβ17 chain on the cell surface, WT-1 tetramer staining was essentially undetectable, indicating that despite the cysteine modification, this construct did not result in sufficient TCR gene expression to out-compete the endogenous TCR. As described in Example 2, the next step was to generate a codon optimized TCR$_{C4}$ construct (see Scholten et al., Clin. Immunol. 119:135, 2006), which showed a substantial increase in tetramer staining (see FIGS. 2A and 3A).

Figure 3A:
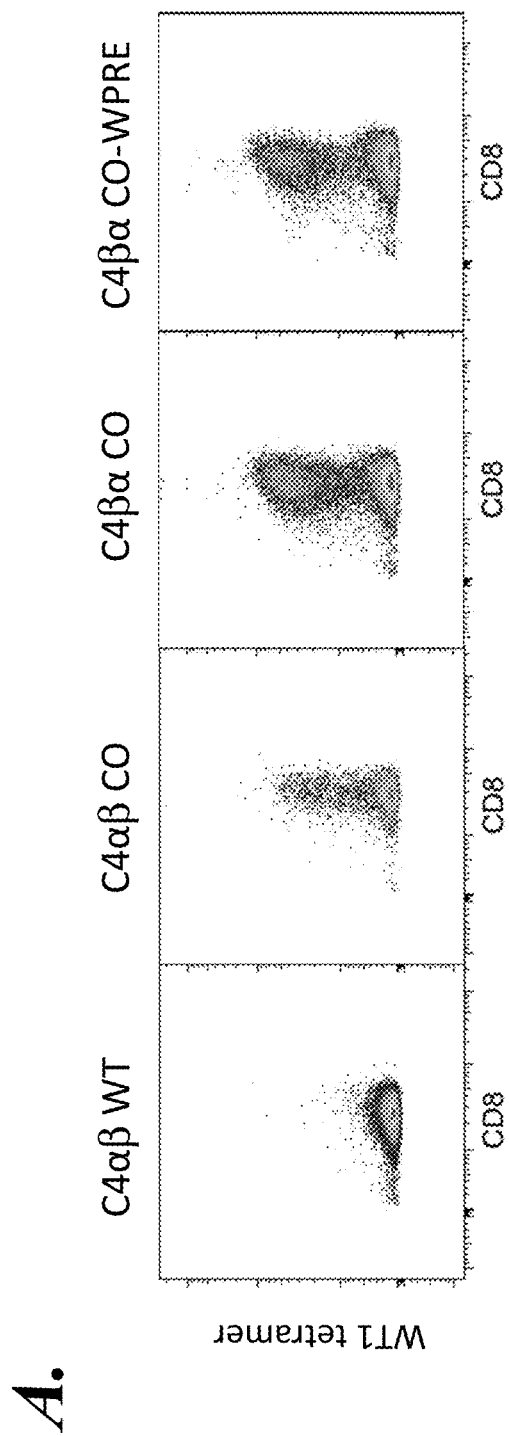
FIGS. 3A-3C show a comparison of TCR surface expression for various different C4-derived TCR constructs. Three different C4-derived TCR constructs, each with a 2A element from the porcine teschovirus (P2A) linking the α and β chains, have the following features: (1) C4α-P2A-β (C4αβWT), (2) a codon-optimized version of C4α-P2A-β (C4αβ CO), and (3) a variant of the codon optimized TCR in which the C4β rather than C4α precedes the P2A element (C4βα CO). (A) Surface expression was detected as a measure of WT-1:HLA-A tetramer binding. (B) Differences in TCR expression between the C4α-P2A-β CO and C4β-P2A-α CO constructs over time were examined and observed to be more apparent towards the end of the T cell's cycle, when endogenous TCRs were expressed at higher levels. (C) Shown is a schematic drawing of a C4 TCRβα construct.
Figure 3B:
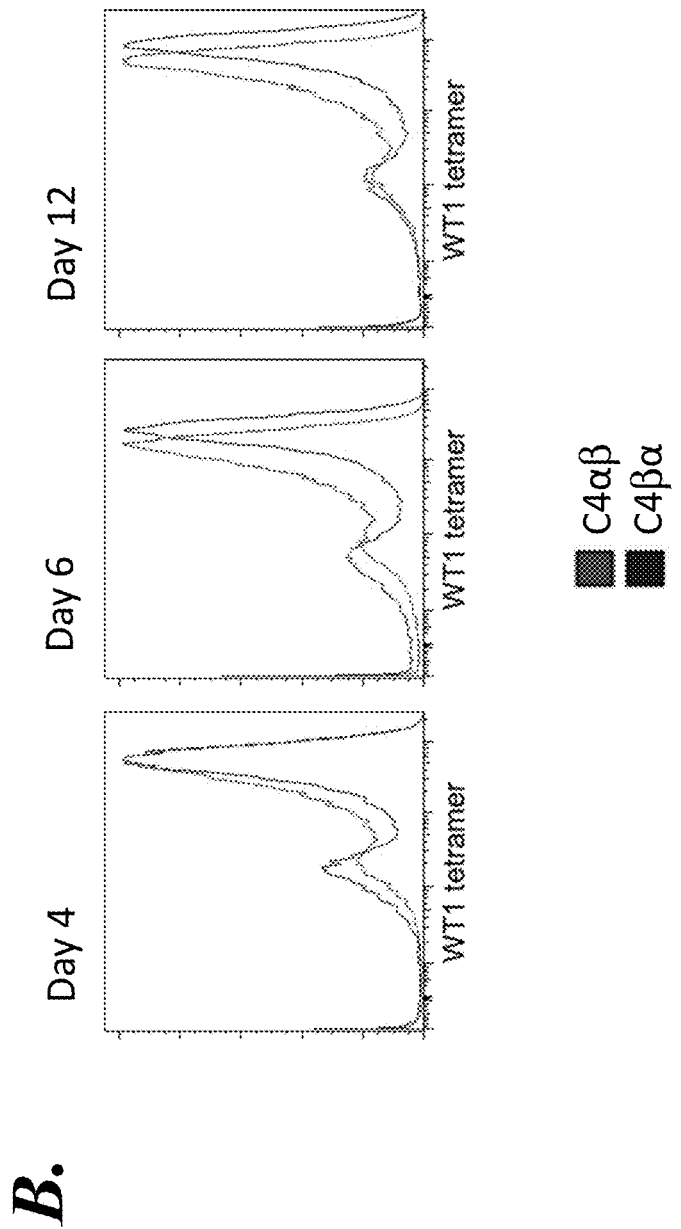
Figure 3C:
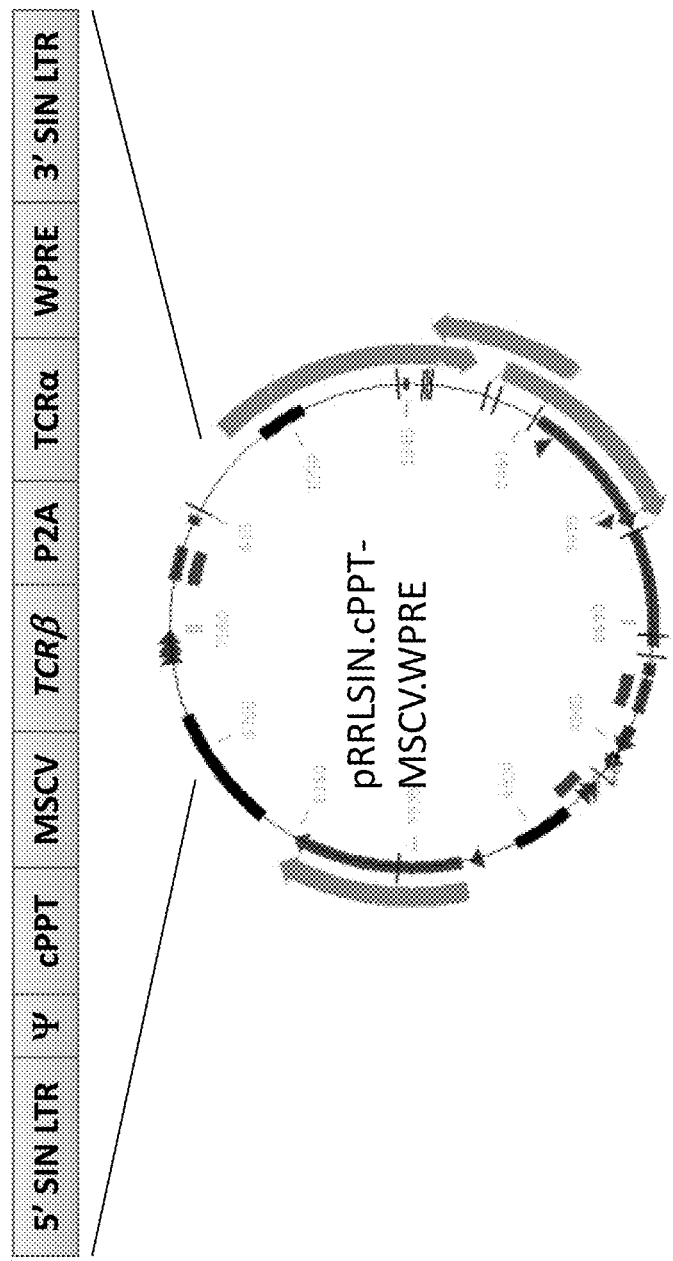

C4αβ and C4βα constructs were examined to determine whether a positional effect of the variable chains might influence surface expression of TCR$_{C4}$ (see Leisegang et al., J. Mol. Med. 86:573, 2008). FIGS. 3A and 3B show a clear increase in tetramer staining when the C4 TCRβ chain was positioned 5' of the P2A element, and this effect was more pronounced at later time-points post-stimulation, indicating that the C4αβ TCR construct was relatively less efficient than the C4βα TCR construct at competing for surface expression with the endogenous TCR, which is down-regulated following the initial T cell stimulation, and gradually increases with time.

These data indicate that (1) the C4βα TCR construct was more efficient at competing for surface expression with the endogenous TCR than the C4αβ TCR construct, and (2) the 21 P2A amino acids affected the TCRα protein function more than the TCRβ protein when located in the 5' position of the P2A-linked TCR$_{C4}$ construct.

Example 4

Cell Surface Stability of Functional WT-1-Specific TCR$_{C4}$

Figure 8A:
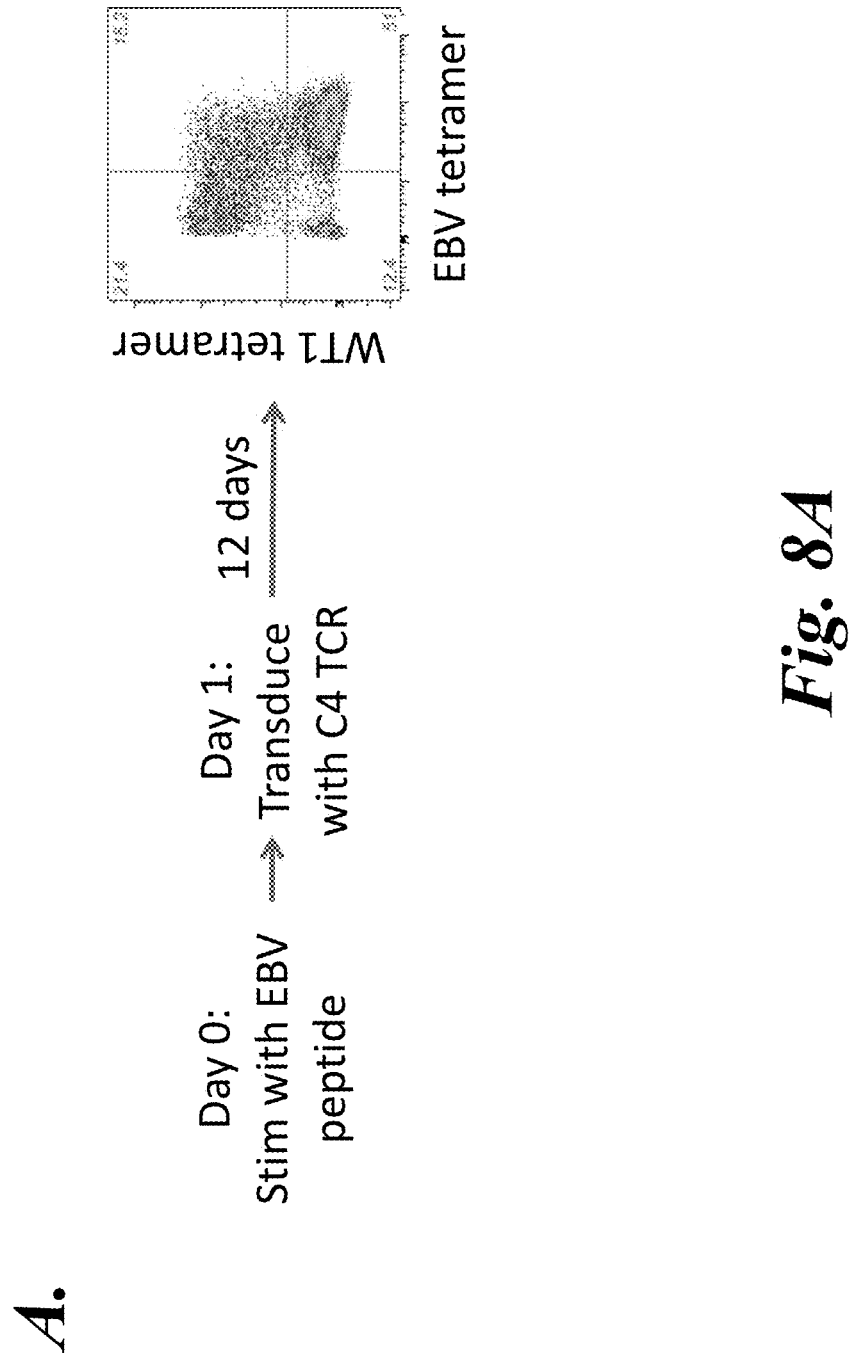
FIGS. 8A-8C show results demonstrating cell surface stability of functional WT-1-specific TCR. (A) Donor PBMCs were stimulated with dendritic cells (DCs) presenting EBV peptide GLCTLVAML (SEQ ID NO.:127), transduced with the C4 TCR construct 24 hours later, and sorted on WT_1 tetramer$^+$, EBV tetramer$^+$, or double positive populations on day 12 as indicated. (B) Sorted populations were analyzed immediately post-sorting, or following 12 days of additional in vitro culture. (C) Donor PBMCs were stimulated with DCs presenting EBV peptide GLCTLVAML (SEQ ID NO.:127) and then sorted for EBV tetramer$^+$ T cells after 12 days of culture. Sorted cells were then re-stimulated with or without C4 TCR transduction on day 1 post stimulation and analyzed by flow cytometry on day 6.

In order to study the stability of functional TCR$_{C4}$ expression on the surface of transduced T cells, CD8$^+$ T cells from an A2+ donor were stimulated with EBV peptide GLCTLVAML (SEQ ID NO.:127) to generate a population of EBV-specific T cells for which endogenous TCR expression could be monitored by EBV tetramer staining T cells were transduced with the TCR$_{C4}$ expression construct 24 hours following EBV peptide stimulation, resulting in preferential transduction of EBV-specific T cells. This approach resulted in a population of EBV+ T cells, a readily detectable population of TCR$_{C4}$ transduced WT-1 tetrame$^+$/EBV tetramer$^+$ double positive (DP) T cells, and a population of TCR$_{C4}$-transduced WT-1 tetramer$^+$ and EBV tetramer$^-$ T cells that either were not reactive to EBV or that had lost EBV TCR surface expression due to competition with TCR$_{C4}$ (FIG. 8A).

Figure 8B:
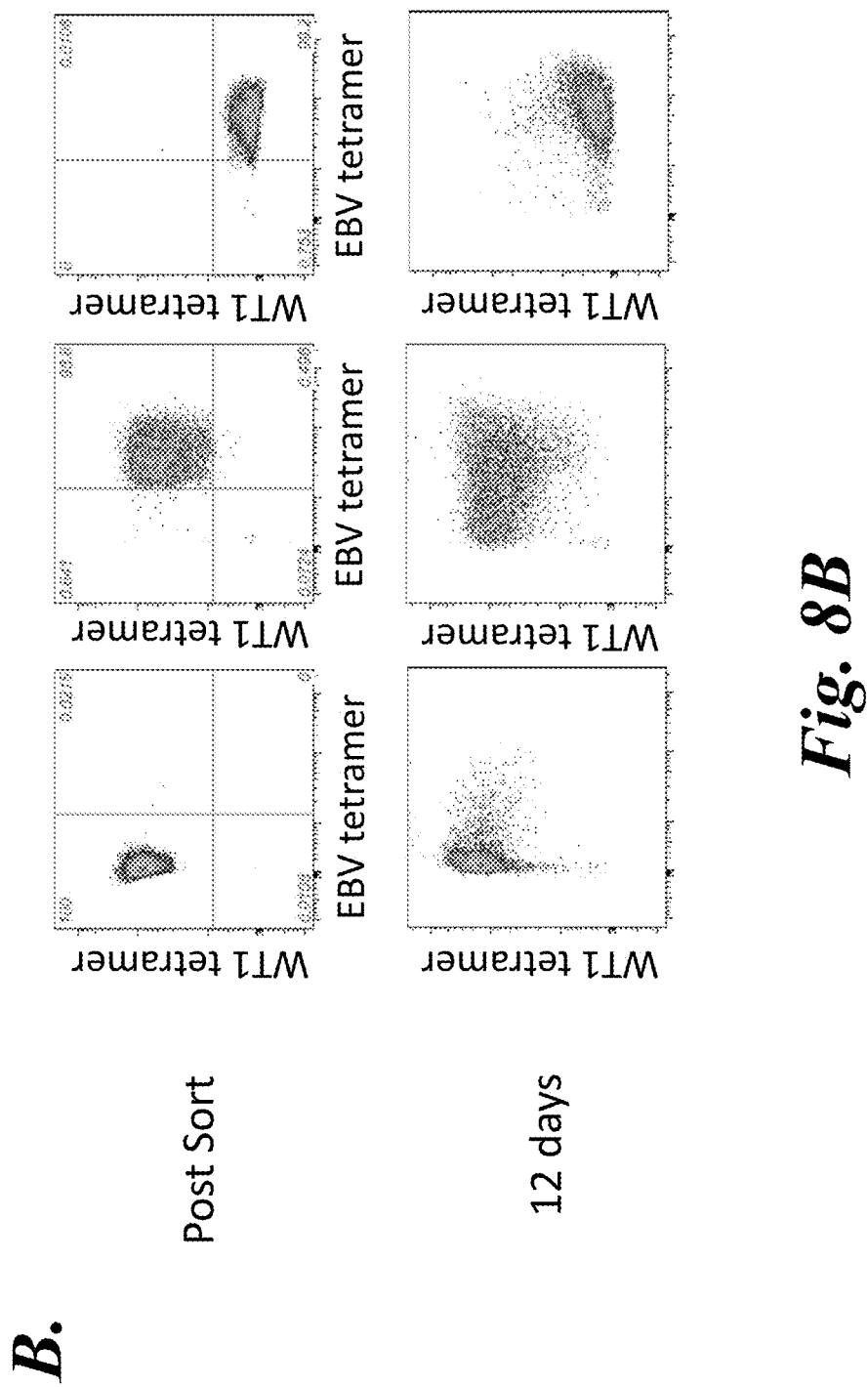

Each of these populations was then sorted and expanded to directly assess the stability of functional TCR$_{C4}$ expression on cells co-expressing an EBV-reactive TCR (FIG. 8B). After 12 days, cultures were analyzed for WT-1 and EBV tetramer staining T cell populations that initially bound only one of the tetramers remained almost exclusively single positive (SP). However, T cells that were uniformly DP for both tetramers following cell sorting, preferentially became single positive for WT-1 tetramer expression following 12 days of in vitro culture, while very few cells lost WT-1-tetramer staining to become EBV SP (FIG. 8B). These results indicate that TCR$_{C4}$ can readily outcompete endogenous TCRs for surface expression.

Figure 8C:
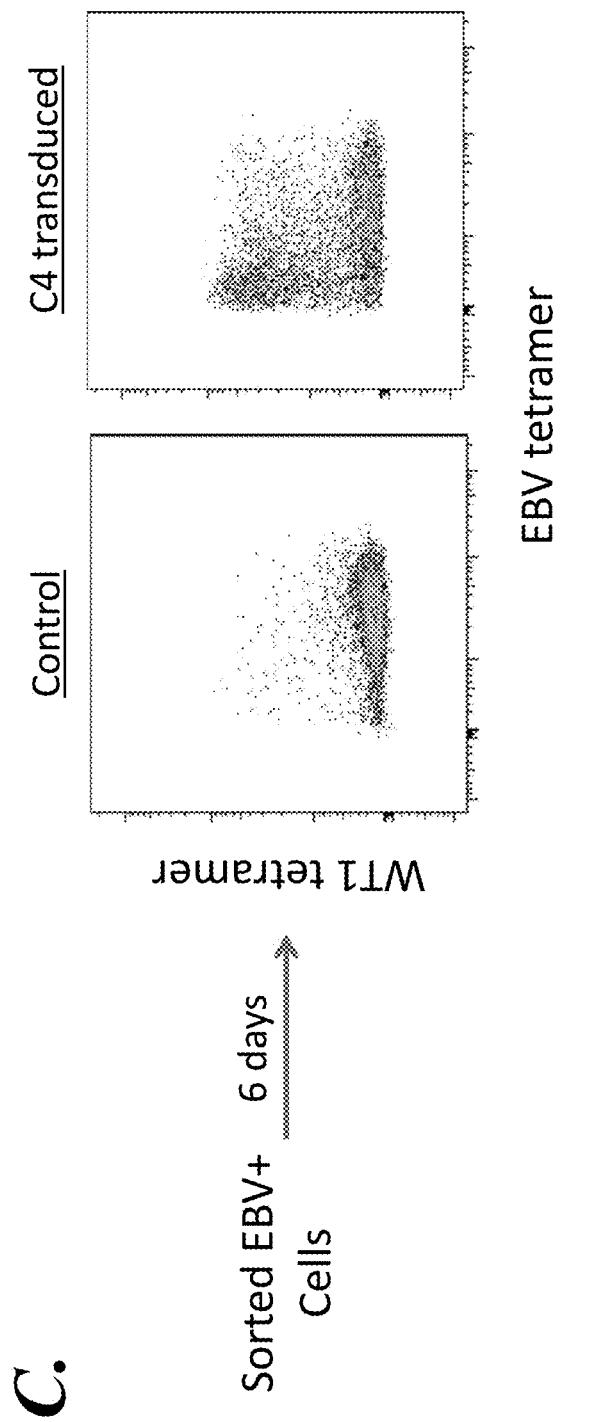

To determine whether the WT-1 tetramer SP population contains primarily cells that had out-competed the endogenous TCR for surface expression, EBV tetramer$^+$ T cells were sorted, and this purified population was then either transduced with the TCR$_{C4}$ construct following restimulation with anti-CD3/CD28, or restimulated without further manipulation (FIG. 8C). EBV-specific T cells that were transduced with the TCR$_{C4}$ construct almost exclusively bound the WT-1-tetramer, indicating that the TCR$_{C4}$ is capable of outcompeting most endogenous TCRs for expression on the surface of T cells.

Example 5

Generation of Variant High Affinity WT-1-Specific TCRs

Even the highest affinity WT-1-specific T cell clones identified from the peripheral T cell repertoire generally will have an attenuated affinity compared to T cells specific for non-self antigens (for example, virus antigens), due to the influence of negative selection during T cell development, which promotes self-tolerance and protects against autoimmunity. Accordingly, saturation mutagenesis techniques were used to generate and identify high affinity TCRs having enhanced affinity in vitro. Two saturation mutagenesis libraries were generated that span the CDR3 region of the C4 TCRα chain (CAATEDYQLIW, SEQ ID NO.:25), as described in Example 1. Both libraries were screened for variants that had an enhanced affinity for the WT-1 epitope following transduction into J.RT3 cells followed by cell sorting based on high level binding of HLA-A2/WT-1 tetramer.

Figure 4A:
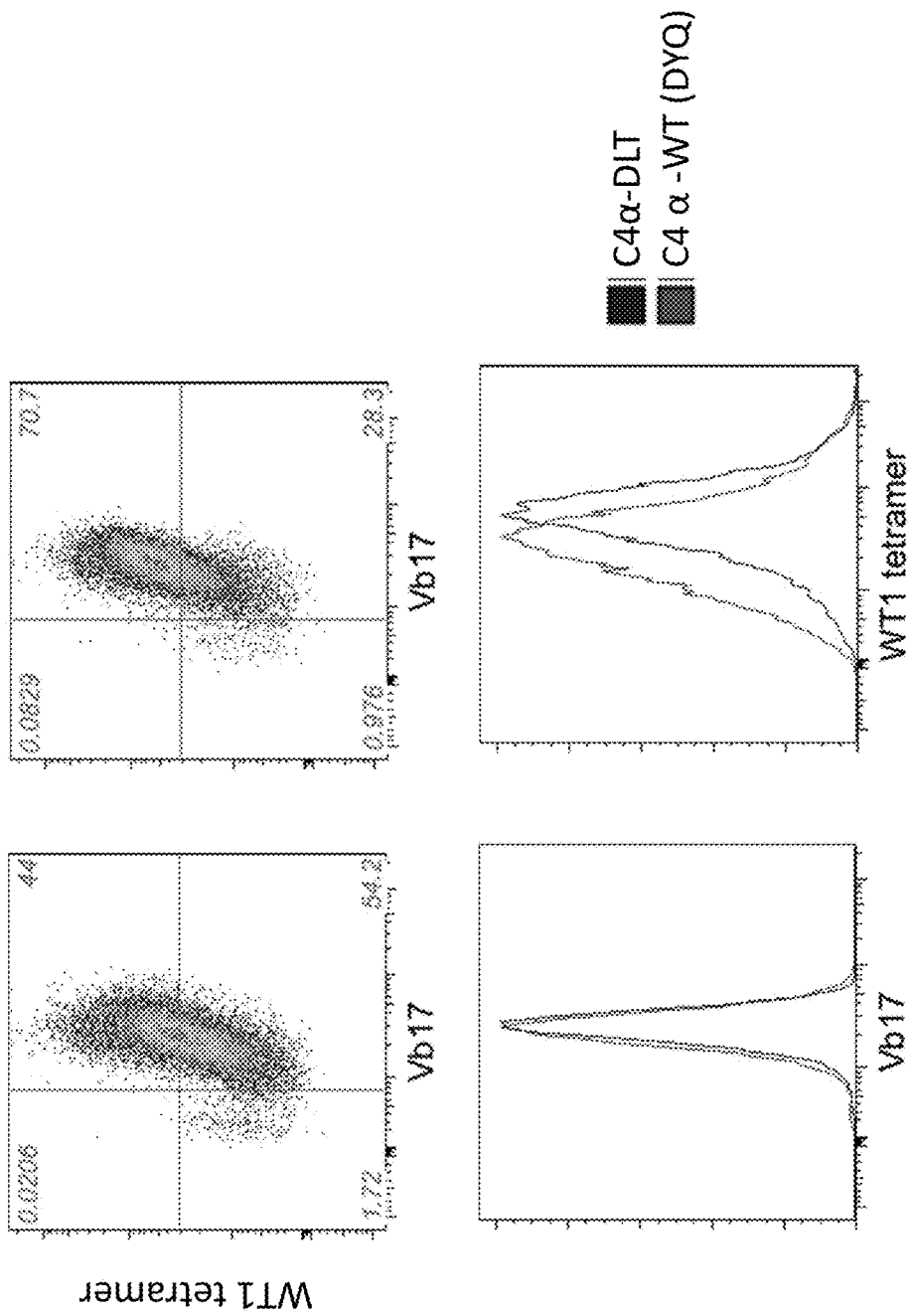
FIGS. 4A-4C show detection and analysis of an enhanced affinity variant of C4 TCR identified by saturation mutagenesis. (A) PBMCs were transduced to express either the wildtype C4α-P2A-C4β construct or the enhanced affinity C4α-P2A-C4β (DLT) construct; transduced cells were isolated by cell sorting, expanded, and analyzed for relative WT-$1^{126-134}$ tetramer staining on cells expressing equivalent levels of the introduced TCR (as measured by Vβ17 staining) (B) Sorted PBMCs expressing either the wildtype C4α-P2A-C4β construct or the enhanced affinity C4α-P2A-C4-β(DLT) were stained with WT-1 peptide/MHC tetramer, analyzed by flow cytometry, and mean fluorescence intensity of tetramer staining was determined using FlowJo software (Treestar). $K_D$ measurements were performed using 2-fold dilutions of PE-conjugated tetramers at a range of concentrations. Apparent $K_D$ values were determined from binding curves by non-linear regression, as the concentration of ligand that yielded half-maximal binding. (C) Sorted PBMCs expressing either the wildtype C4α-P2A-C4β construct or the enhanced affinity C4α-P2A-C4-β (DLT) were incubated with $^{51}$Chromium loaded target cells pulsed with decreasing concentrations of WT-1$^{126\text{-}134}$ peptide as indicated, and specific T cell mediated killing was measured as a percent of maximum chromium release.

Candidate HLA-A2/WT-1 tetramer-binding variants were isolated from both libraries, and one variant having a DYQ to DLT mutation (C4-DLT) exhibited higher levels of HLA-A2/WT-1 tetramer binding compared to the unmutated C4 TCR (C4-WT), and was found to have enhanced HLA-A2/WT-1 tetramer equilibrium binding kinetics (FIG. 4A). It should be noted that these experiments were done in the presence of CD8, which contributes significantly to TCR-peptide/MHC interactions, which thus may decrease apparent differences in the relative affinity between TCRs.

Figure 4B:
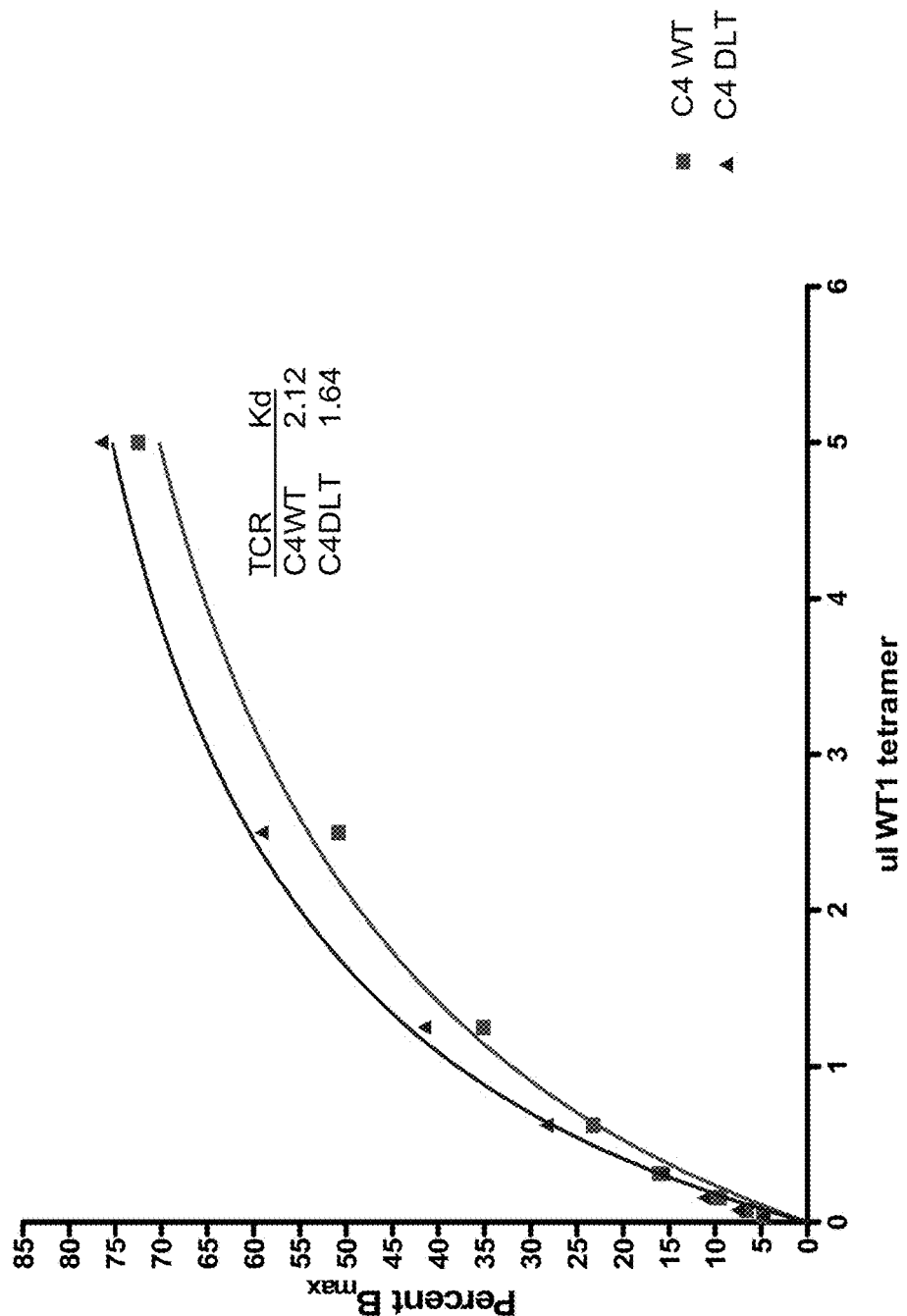
Figure 4C:
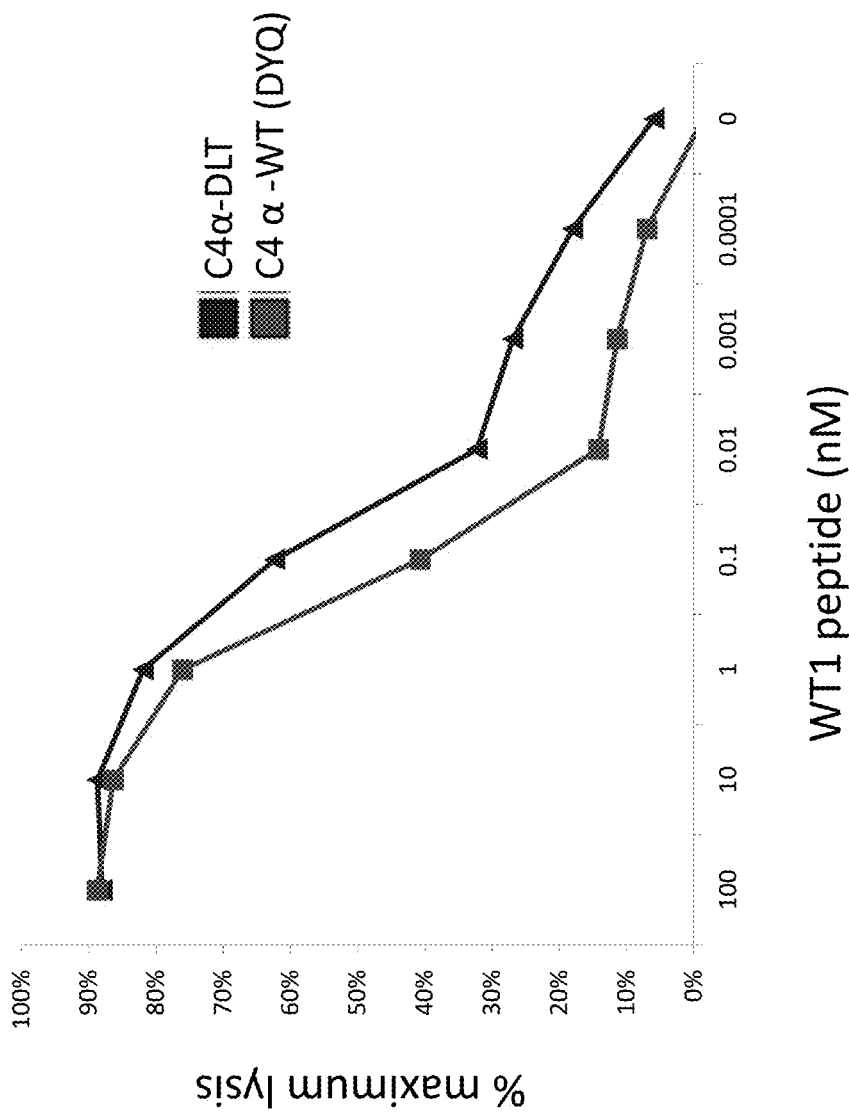
Figure 5:
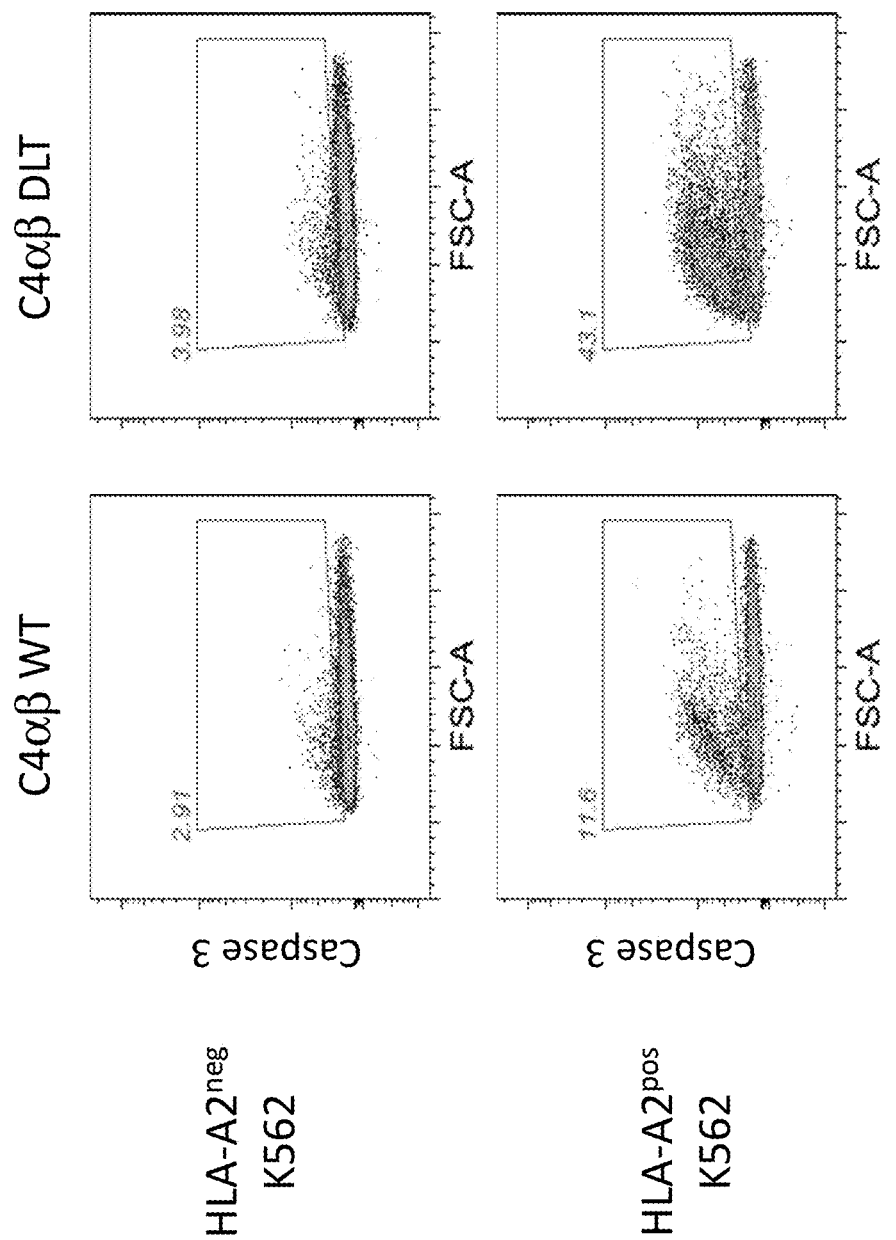
FIG. 5 shows PBMCs transduced with the C4αβ(DLT) TCR show enhanced killing of tumor cells naturally presenting WT-1 antigen. The HLA-A2 negative K562 tumor cell line or K562 cells transduced to express HLA-A2 were used as target cells for PBMCs expressing either the wildtype C4α-P2A-C4β construct or the enhanced affinity C4α-P2A-C4-β(DLT) TCR. Tumor killing was determined by measuring cleaved caspase-3 in tumor cells by flow cytometry.

When transferred into CD8+ T cells and assessed for the ability to kill target cells pulsed with decreasing concentrations of peptide, C4-DLT showed a 5-10 fold increase in antigen sensitivity compared to C4-WT (FIG. 4B), and a similar increase in antigen sensitivity was observed when cytokine production (IFNγ) in response to limiting peptide concentrations was assayed (FIG. 4C). Likewise, T cells expressing C4-DLT exhibited enhanced killing (through caspase-3 activation) compared to T cells expressing C4-WT when targeting an HLA-2 expressing version of the leukemia cell line K562, which expresses WT-1, and can process and present the WT-1 peptide RMFPNAPYL (SEQ ID NO.:16) epitope to C4-WT and C4-DLT when transduced with HLA-A2 (FIG. 5).

Example 6

Kinetic and Cytolytic Activity of TCR C4α Mutant as Compared to Wild-Type TCR C4

Figure 6A:
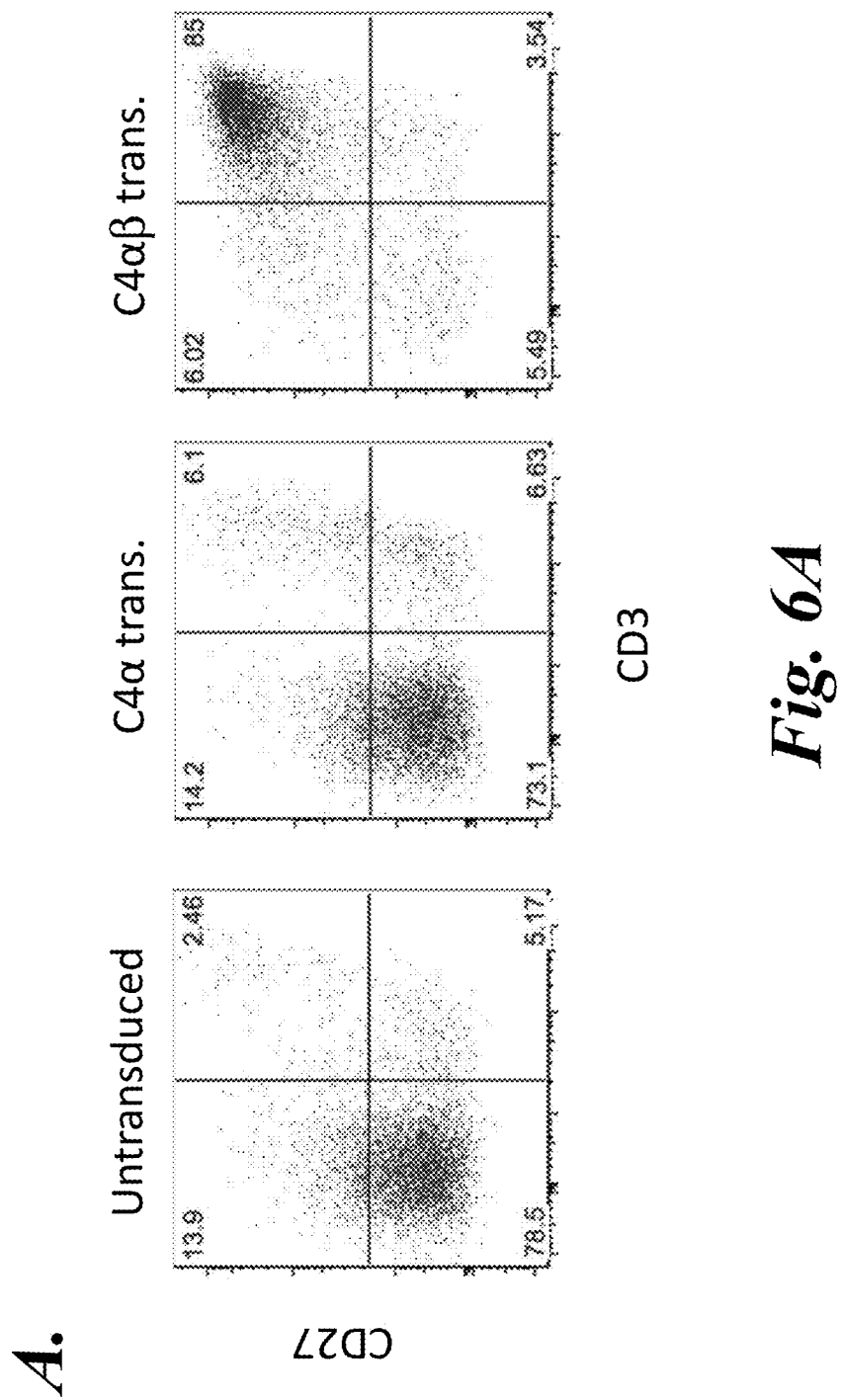
FIGS. 6A-6C show results from the generation and screening of human agonist-selected TCRβ libraries. CD34+ HPCs were purified from umbilical cord blood, lentivirally transduced with either C4α-IRES-GFP or C4αβ and co-cultured with the OP9-A2-DL1 cell line in the presence of 1 μg/mL WT-1 peptide. (A) Cultures were analyzed on day 31 for expression of CD3 and CD27. (B) On day 34, cultures were analyzed for expression of CD27 and Vβ17, and about 2.5×10$^5$ Vβ17+CD27+ cells were sorted for TCRβ library generation. (C) Vβ17-Cβ1 and Vβ17-Cβ2 libraries were generated, transduced into the H9.CD8-C4α cell line, followed by sorting for transduced C4α-GFP+ Vβ17+ cells. Cells were then sorted twice with WT-1-tetramer and analyzed for tetramer and Vβ17 staining by flow cytometry.
Figure 6B:
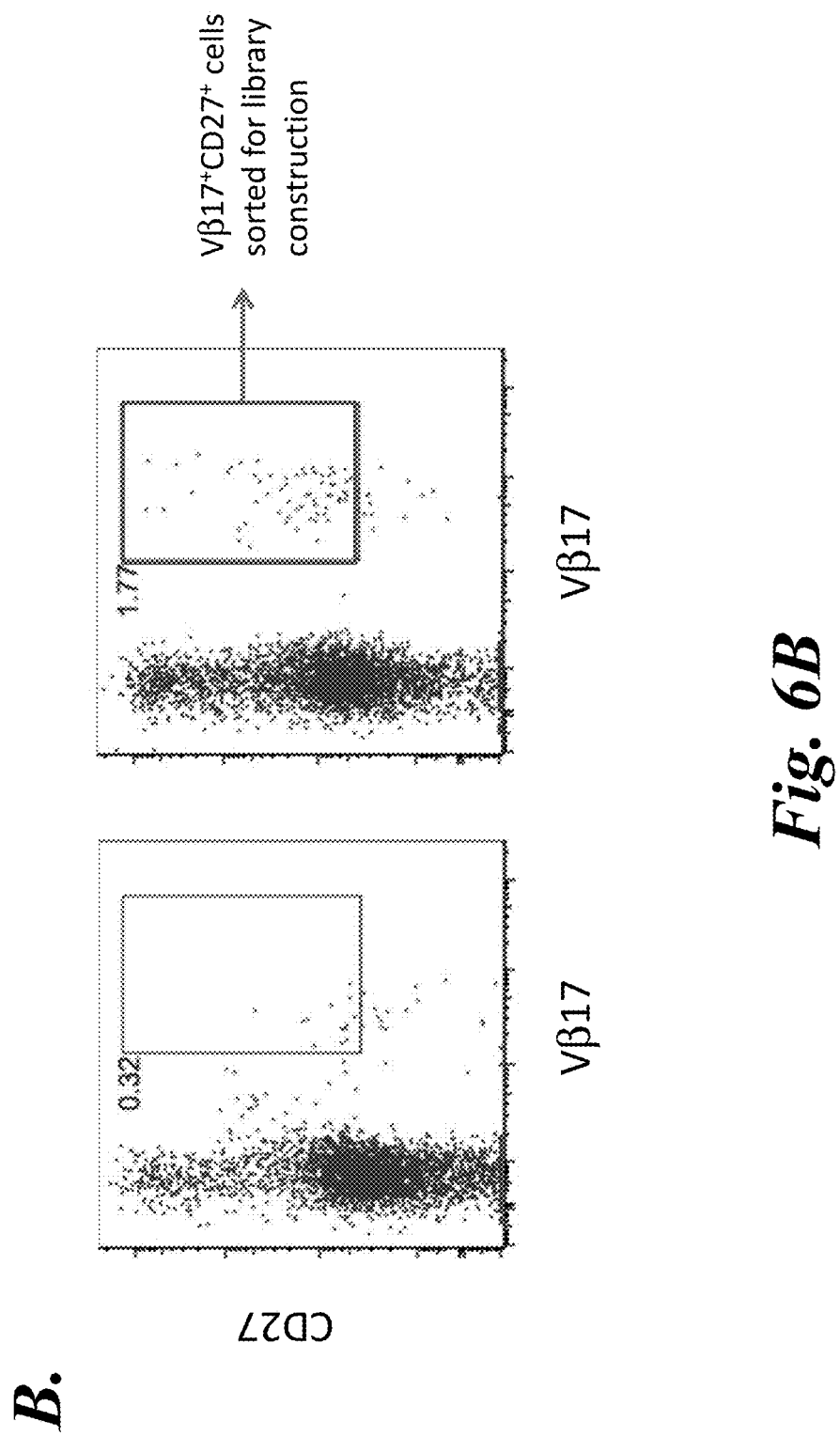

Cord blood-derived CD34$^+$ HPCs were transduced to express the TCRα chain of a high affinity HLA-A2-restricted WT-1-specific TCR (TCR$_{C4}$) studied in clinical trials as described in Example 7. The transduced cells were cultured on OP9-DL1 cells expressing HLA-A2 (OP9-A2-DL1) in the presence of WT1 peptide. As a positive control, cord blood HSCs were also transduced with both the TCRα and TCRβ chains of TCR$_{C4}$ (C4αβ). The majority of human γδ-T cell progenitors express CD4 and CD8 during development on OP9-DL1 (Van Coppernolle et al., *Leukemia* 26:127, 2011), but since phenotypically mature γδ T cells (similar to murine DN CD24$^-$ cells) express high levels of CD27 (Van Coppernolle et al., *J. Immunol.* 183:4859, 2009), expression of CD27 and the parental Vβ17 TCRβ chain were used to enrich for agonist-selected T cells. The relative proportion of CD3$^+$CD27$^+$ cells was analyzed for untransduced, C4α-transduced, and C4αβ-transduced cells after 31 days of in vitro culture. The majority of cells in the C4αβ-transduced cultures were CD3$^+$CD27$^+$. The C4α-transduced cultures had an increased percentage of CD3$^+$CD27$^+$ cells compared to untransduced controls, and a 5-fold increase in the percentage of CD3$^+$ cells expressing the parental Vβ17 (FIG. 6A). Only Vβ17$^+$CD27$^+$ cells were collected for the TCRβ library construction on day 34 of culture (FIG. 6B).

Figure 6C:
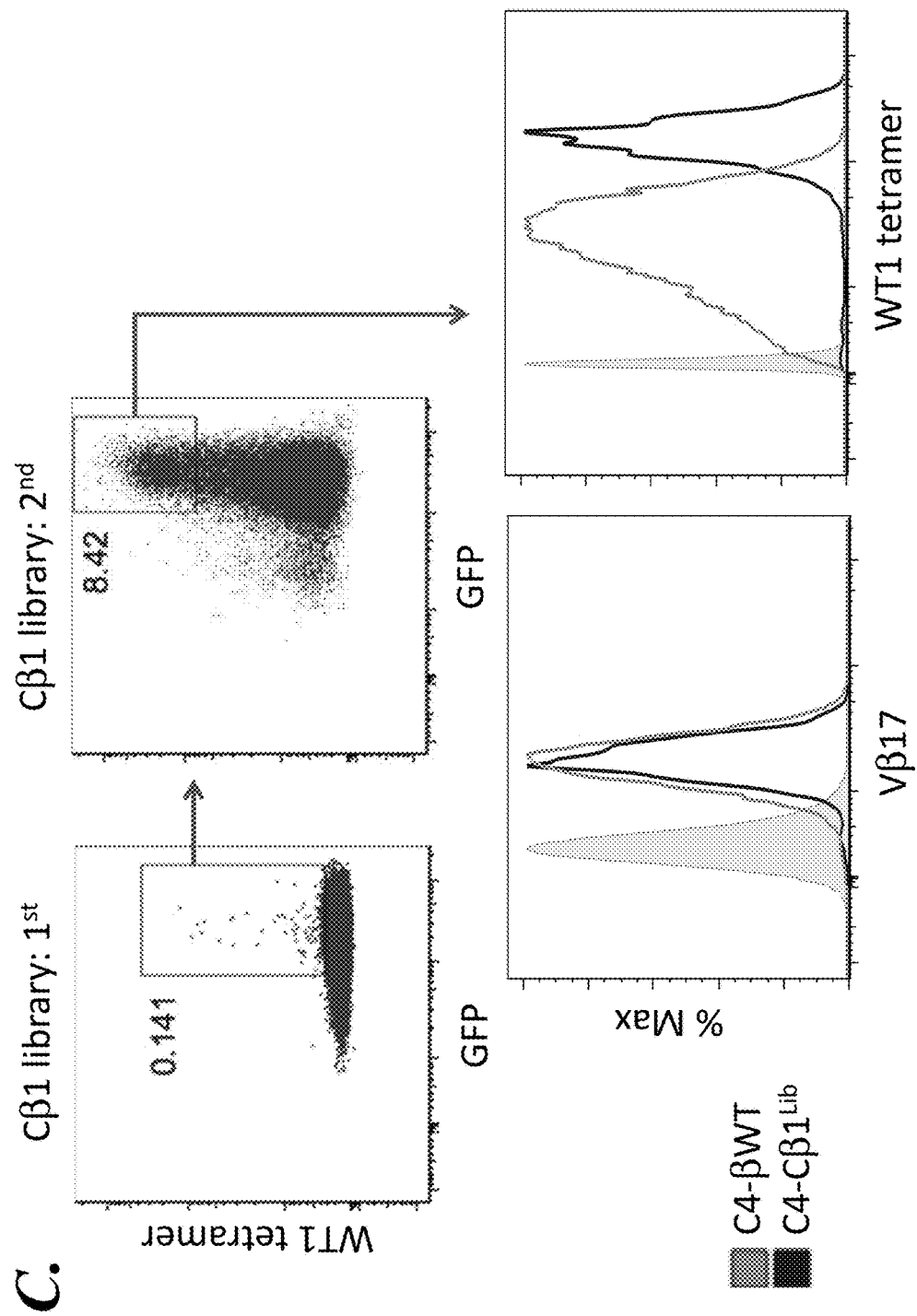

Vβ17-Cβ1 and Vβ17-Cβ2 libraries were transduced into H9.CD8-C4α cells and sorted for WT-1 tetramer$^+$ cells within the transduced population. After a single WT-1 MHC tetramer sort, cells transduced with Vβ17-Cβ1 library exhibited a range of tetramer reactivity, indicating that multiple TCRβ chains present in the Vβ17-sorted population could confer WT-1 antigen specificity. Cells exhibiting the highest level of WT-1 MHC tetramer staining were isolated by a second WT-1 MHC tetramer sort, and compared to H9.CD8-C4α cells expressing the parental C4β chain. While both transduced cell populations expressed similar levels of Vβ17, substantially higher tetramer staining was observed for the tetramer$^{hi}$ cells enriched from the Vβ17-Cβ1 library (FIG. 6C). In some embodiments, these high affinity, Cβ1 library-derived TCRβ chains can have utility as second generation WT-1-specific receptors in TCR gene therapy trials.

The retroviral packaging line PlatE was obtained from Cell Biolabs (San Diego, Calif.). The OP9-K$^b$D$^b$DL1 cell line was generated by transducing the OP9 cell line (Riken, Japan) with a retroviral construct containing the Dll-1 gene followed by an IRES and H-2D$^b$ (to generate OP9-K$^b$DL1 cells), and separately transduced with H-2K$^b$. The OP9-K$^b$D$^b$DL1-WT1 cell line was further transduced to express murine WT1. The OP9-A2-DL1 cell line was generated by transducing OP9-K$^b$DL1 cells with a retroviral construct encoding HLA-A2-IRES-human β2M. The OP9 cells and a retroviral construct containing the Dll1 gene followed by IRES-GFP were obtained from the lab of Juan Carlos Zúñiga-Pflücker. The 58$^{-/-}$3 D-PYYα cell line was generated by retrovirally tranducing the TCRα/TCRβ-deficient cell line 58–/– with Mig2-3D-PYYα. The H9.CD8-C4α cell line was generated by lentivirally transducing the human T cell line H9 with a CD8α-P2A-β construct followed by lentiviral transduction to express C4α-IRES-GFP.

Example 7

Donor-Derived, Virus Specific CD8+ T Cells Expressing a WT-1-Specific T Cell Receptor Provides Anti-Leukemic Relapse Activity in AML Patients Relapse is the leading cause of death following allogeneic hematopoietic cell transplant (HCT) for hematological malignancies. Although evidence suggests that the beneficial donor T cell-mediated graft versus leukemia (GVL) effect can reduce post-HCT relapse rates, this effect is often mitigated by morbidity and mortality associated with the accompanying graft versus host disease (GVHD). Thus, providing antigen-specific T cells that selectively target leukemia associated antigen (LAA) can provide a distinct opportunity to promote GVL activity without inducing GVHD. Wilms Tumor protein 1 (WT-1) is a non-polymorphic zinc finger transcription factor that plays a key role in cell growth and differentiation. WT-1 has very limited expression in normal adult tissues, is expressed 10-1000 fold more in leukemia cells as compared to normal CD34$^+$ cells, and has been shown to contribute to leukemogenesis. Furthermore, the magnitude of expression of WT-1 in leukemic cells correlates with prognosis and clinical aggressiveness. WT-1 is immunogenic and, thus, constitutes an attractive candidate immunotherapeutic target for induced CD8$^+$ cytotoxic T-cells (CTL) responses (Cheever et al., *Clin. Cancer Res.* 15:5323, 2009). Transferred donor derived WT-1-reactive CD8+ CTL clones can persist in post-transplant patients and mediate anti-leukemic activity (Chapuis et al., *Sci. Transl. Med.* 5:174ra27, 2013).

In this study, escalating doses of donor-derived virus specific CD8+ T cells that had been transduced to express a high affinity T cell receptor specific for the HLA A*02:01-restricted WT1$_{126-134}$ (RMFPNAPYL, SEQ ID NO.:16) epitope were administered to high-risk acute myeloid leukemia (AML) patients after allogeneic HCT, with escalating doses withheld if a previous dose persisted at a frequency of >3% of peripheral blood CD8+ T cells. At one observation point, at which nine patients had been treated in the study and received a total of 22 infusions, three (3) patients had completed the four T cell infusions, with the last infusion followed by a two week course of IL-2. CTC Grade≥3 Adverse Events had been transient hypotension and a febrile reaction, and transient leukopenia, lymphopenia and thrombocytopenia. No end-organ toxicities attributed to the infused T cells had been observed. One patient had experienced exacerbation of acute GVHD after T cell infusion, and one patient developed chronic GVHD, although there was no evidence the GVHD in either patient reflected activity of the infused T cells.

Three patients who were treated with T cells after a second allogeneic HCT for relapsed AML (two of whom had persistent/relapse disease after second transplant) were alive with no evidence of disease 14, 8 and 7 months after initiation of T cell infusion (16, 26, and 9 months after second transplant accordingly) with no additional anti-leukemic therapy after completion of study treatment. One patient with high risk AML who was treated prophylactically after allogeneic HCT for AML in second complete remission (CR2) was alive and with no evidence of disease 13 months after initiation of study treatment (15 months after transplant) (Table 1).

Figure 7:
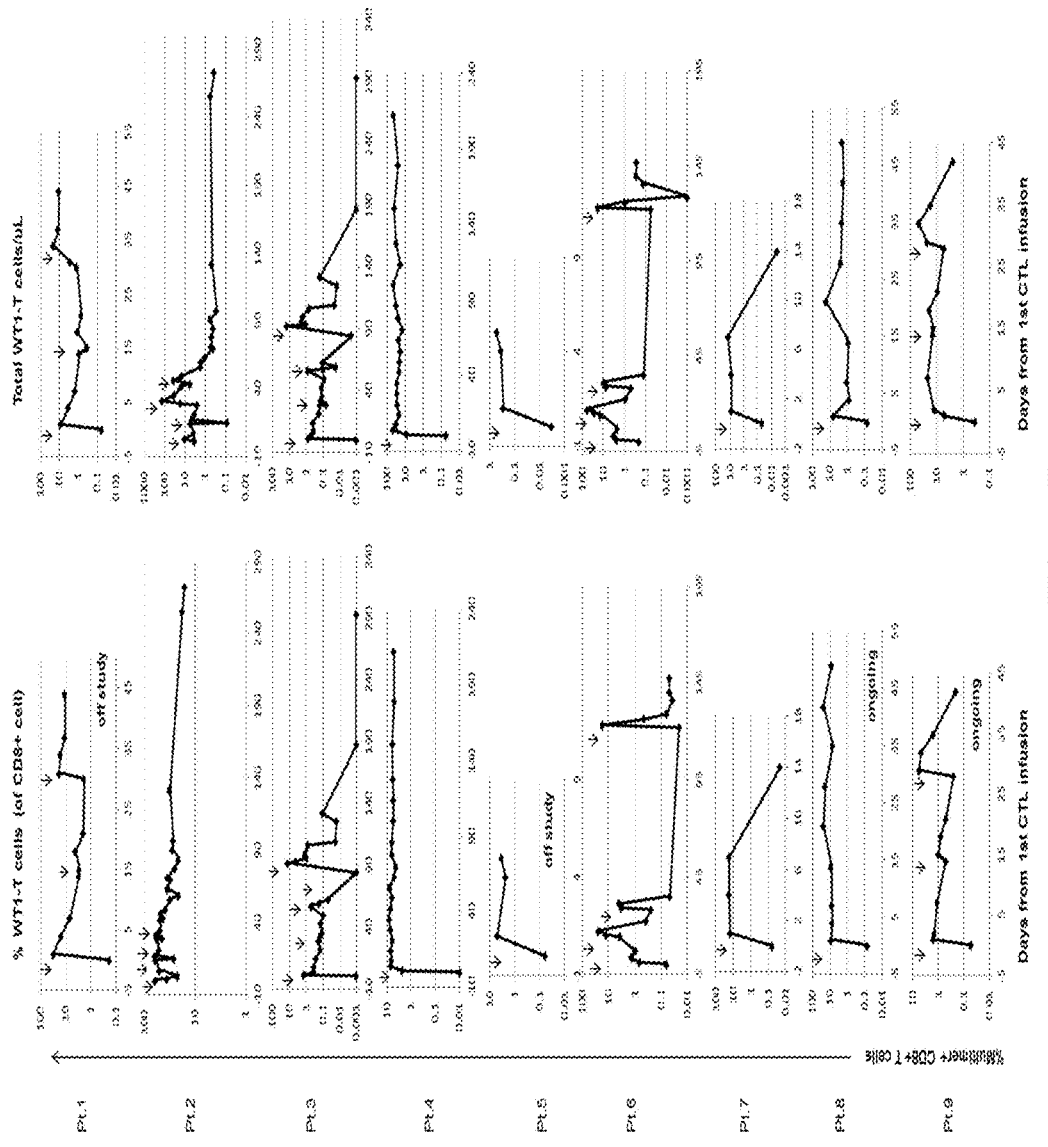
FIG. 7 shows the persistence in 9 leukemia patients of donor-derived virus-specific CD8 T cells transduced to express the C4βα TCR construct. Donor T cells were stimulated with a peptide from either EBV or CMV to specifically activate a population of virus-specific T cells with a central memory phenotype, and to target lentiviral transduction preferentially to these activated and, thus, rapidly dividing cells. Cells were transduced with the C4βα TCR construct and sorted for T cells that stained positive for both HLA-A2/WT-1 and HLA-A2/viral peptide-specific tetramers by flow cytometric cell sorting. Sorted cells were expanded and infused into leukemia patients at the timepoints indicated with a down-facing arrow.

Persistence of the transduced CTL in vivo was observed as being variable, with transferred CTL detectable between 4 to at least 290 days after T cell infusions (Table 1, FIG. 7).

TABLE 1

| | | | Clinical Outcomes | | | | |
|---|---|---|---|---|---|---|---|
| Patient | Diagnosis | Disease Status prior to Study Treatment | Disease Burden during T cell Infusion | Number of Infusions | CTL Persistence (Days after last Infusion) | Outcome* | Survival* |
| 1 | AML | Relapse 5 years after allogeneic HCT (medullary and extramedullary disease) | Present | 3 | 14+ | Progressive disease | Alive |
| 2 | AML | Relapse 10 years after first allogeneic HCT. MRD early after second HCT | Present | 4(+IL2) | 290+ | Remission 16 mos. after transplant | Alive |

TABLE 1-continued

Clinical Outcomes

| Patient | Diagnosis | Disease Status prior to Study Treatment | Disease Burden during T cell Infusion | Number of Infusions | CTL Persistence (Days after last Infusion) | Outcome* | Survival* |
|---|---|---|---|---|---|---|---|
| 3 | AML | HCT at CR2. No evidence of disease after HCT | Absent | 4(+IL2) | 20 | Remission 15 mos. after transplant | Alive |
| 4 | AML | Relapse with extramedulary disease one year after second allogeneic HCT | Absent | 1 | 210+ | Remission 26 mos. after transplant (8 mos. after treatment) | Alive |
| 5 | MDS → AML | Persistent disease after HCT | Present | 1 | 5+ | Progressive disease | Dead |
| 6 | AML | Second HCT for relapse 4 years after first HCT | Absent | 4(+IL2) | 4 | Remission 9 mos. after transplant | Alive |
| 7 | AML | Persistence disease after HCT | Present | 1 | 30+ | Progressive disease | Dead |
| 8 | AML | HCT in CR2. MRD early after transplant | Present | 1 | 50+ | Ongoing treatment | Alive |
| 9 | AML | HCT in CR2. Relapse early after transplant | Absent | 3 | 14+ | Ongoing treatment | Alive |

*as of July 2014
+persisting T cells detected at most recent analysis as of the assessment These preliminary results of this study indicate that transfer of donor-derived virus specific CD8+ T cells transduced to express a WT-1-specific T cell receptor of provided embodiments (α-chain SEQ ID NO.:5 or 6 and β-chain SEQ ID NO.:12 or 13, respectively) could be accomplished without significant toxicity and that such therapy could provide anti-leukemic activity.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated polynucleotide encoding a binding protein, comprising a polynucleotide encoding a human TCR α-chain variable (V$_α$) domain that contains the complementarity determining region 3 (CDR3) amino acid sequence of SEQ ID NO.:25 or 26, the CDR1 amino acid sequence of SEQ ID NO: 23, and the CDR2 amino acid sequence of SEQ ID NO: 24, wherein the polynucleotide encoding the V$_α$ domain is at least 80% identical to the nucleotide sequence of SEQ ID NO 78, 128 or 80, provided that the Vα domain comprises the CDR3 of SEQ ID NO:25 or 26, the CDR1 of SEQ ID NO:23 and the CDR2 of SEQ ID NO:24; and a polynucleotide encoding a human TCR β-chain variable (V$_β$) domain that contains the CDR3 amino acid sequence of SEQ ID NO.:29, the CDR1 amino acid sequence of SEQ ID NO:27, and the CDR2 amino acid sequence of SEQ ID NO:28, wherein the polynucleotide encoding the V$_β$ domain is at least 80% identical to the nucleotide sequence of SEQ ID NO. 89, provided that the Vβ domain comprises the CDR3 of SEQ ID NO:29, the CDR1 of SEQ ID NO:27 and the CDR2 of SEQ ID NO:28; and wherein the encoded binding protein specifically binds to a RMFPNAPYL (SEQ ID NO.:16):human leukocyte antigen-A*201 (HLA-A*201) complex.

2. The isolated polynucleotide of claim 1, wherein the encoded V$_α$ domain has at least 90% sequence identity to the amino acid sequence of SEQ ID NO.:1 or 2.

3. The isolated polynucleotide of claim 2, wherein:
(a) the V$_α$ domain encoding polynucleotide comprises the nucleotide sequence of SEQ ID NO.:78, 128, or 80; or
(b) the V$_α$ domain encoding polynucleotide consists of the nucleotide sequence of SEQ ID NO.:78, 128, or 80.

4. The isolated polynucleotide of claim 1, wherein the encoded V$_β$ domain has at least 90% sequence identity to the amino acid sequence of SEQ ID NO.:9.

5. The isolated polynucleotide of claim 4, wherein:
(a) the V$_β$ domain encoding polynucleotide comprises the nucleotide sequence of SEQ ID NO.:89; or
(b) the V$_β$ domain encoding polynucleotide consists of the nucleotide sequence of SEQ ID NO.:89.

6. The isolated polynucleotide of claim 1, wherein the V$_α$ domain encoding polynucleotide comprises a polynucleotide encoding an α-chain constant domain having at least 90% sequence identity to the amino acid sequence of SEQ ID NO.:3 or 4 and the polynucleotide encoding the α-chain constant domain is at least 80% identical to the nucleotide sequence of SEQ ID NO.:82 or 84.

7. The isolated polynucleotide of claim 6, wherein:
(a) the α-chain constant domain encoding polynucleotide comprises the nucleotide sequence of SEQ ID NO.:82 or 84; or
(b) the α-chain constant domain encoding polynucleotide consists of the nucleotide sequence of SEQ ID NO.:82 or 84.

8. The isolated polynucleotide of claim 1, wherein the V$_β$ domain encoding polynucleotide comprises a polynucleotide encoding a β-chain constant domain having at least 90% sequence identity to the amino acid sequence of SEQ ID NO.:10 or 11 and the polynucleotide encoding the β-chain constant domain is at least 80% identical to the nucleotide sequence of SEQ ID NO.:92 or 93.

9. The isolated polynucleotide of claim 8, wherein:
(a) the β-chain constant domain encoding polynucleotide comprises the nucleotide sequence of SEQ ID NO.:92 or 93; or
(b) the β-chain constant domain encoding polynucleotide consists of the nucleotide sequence of SEQ ID NO.:92 or 93.

10. The isolated polynucleotide of claim 1, wherein the V$_α$ domain encoding polynucleotide comprises a polynucleotide encoding an α-chain constant domain having at least 90% sequence identity to the amino acid sequence of SEQ ID NO.:3 or 4 and the polynucleotide encoding the α-chain constant domain is at least 80% identical to the nucleotide sequence of SEQ ID NO.:82 or 84; and the V$_β$ domain encoding polynucleotide comprises a polynucleotide encoding a β-chain constant domain having at least 90% sequence identity to the amino acid sequence of SEQ ID NO.:10 or 11 and the polynucleotide encoding the β-chain constant domain is at least 80% identical to the nucleotide sequence of SEQ ID NO.:92 or 93.

11. The isolated polynucleotide of claim 10, wherein:
(a) the α-chain constant domain encoding polynucleotide comprises the nucleotide sequence of SEQ ID NO.:82 or 84; or
(b) the α-chain constant domain encoding polynucleotide consists of the nucleotide sequence of SEQ ID NO.:82 or 84.

12. The isolated polynucleotide of claim 10, wherein:
(a) the β-chain constant domain encoding polynucleotide comprises the nucleotide sequence of SEQ ID NO.:92 or 93; or
(b) the β-chain constant domain encoding polynucleotide consists of the nucleotide sequence of SEQ ID NO.:92 or 93.

13. The isolated polynucleotide of claim 10, wherein:
(i) (a) the α-chain constant domain encoding polynucleotide comprises the nucleotide sequence of SEQ ID NO.:82 or 84; or
(b) the α-chain constant domain encoding polynucleotide consists of the nucleotide sequence of SEQ ID NO.:82 or 84; and
(ii) (a) the β-chain constant domain encoding polynucleotide comprises the nucleotide sequence of SEQ ID NO.:92 or 93; or
(b) the β-chain constant domain encoding polynucleotide consists of the nucleotide sequence of SEQ ID NO.:92 or 93.

14. The isolated polynucleotide of claim 1, wherein the V$_α$ domain encoding polynucleotide is contained in a polynucleotide encoding a T cell receptor (TCR) α-chain having at least 90% sequence identity to the amino acid sequence of any one of SEQ ID NOS.:5-8 and the polynucleotide encoding the TCR α-chain is at least 80% identical to the nucleotide sequence of SEQ ID NO.:86 or 87.

15. The isolated polynucleotide of claim 14, wherein:
(a) the TCR α-chain encoding polynucleotide comprises the nucleotide sequence of SEQ ID NO.:86 or 87; or
(b) the TCR α-chain encoding polynucleotide consists of the nucleotide sequence of SEQ ID NO.:86 or 87.

16. The isolated polynucleotide of claim 1, wherein the $V_\beta$ domain encoding polynucleotide is contained in a polynucleotide encoding a TCR β-chain having at least 90% sequence identity to the amino acid sequence of SEQ ID NO.:12 or 13 and the polynucleotide encoding the TCR β-chain is at least 80% identical to the nucleotide sequence of SEQ ID NO.:95.

17. The isolated polynucleotide of claim 16, wherein:
(a) the TCR β-chain encoding polynucleotide comprises the nucleotide sequence of SEQ ID NO.:95; or
(b) the TCR β-chain encoding polynucleotide consists of the nucleotide sequence of SEQ ID NO.:95.

18. The isolated polynucleotide of claim 1, wherein the $V_\alpha$ domain encoding polynucleotide is contained in a polynucleotide encoding a TCR α-chain having at least 90% sequence identity to the amino acid sequence of any one of SEQ ID NOS.:5-8 and the polynucleotide encoding the TCR α-chain is at least 80% identical to the nucleotide sequence of SEQ ID NO.:86 or 87; and the $V_\beta$ domain encoding polynucleotide is contained in a polynucleotide encoding a TCR β-chain having at least 90% sequence identity to the amino acid sequence of SEQ ID NO.:12 or 13 and the polynucleotide encoding the TCR β-chain is at least 80% identical to the nucleotide sequence of SEQ ID NO.:95.

19. The isolated polynucleotide of claim 18, wherein:
(i) (a) the TCR α-chain encoding polynucleotide comprises the nucleotide sequence of SEQ ID NO.:86; or
(b) the TCR α-chain encoding polynucleotide consists of the nucleotide sequence of SEQ ID NO.:86; and
(ii) (a) the TCR β-chain encoding polynucleotide comprises the nucleotide sequence of SEQ ID NO.:95; or
(b) the TCR β-chain encoding polynucleotide consists of the nucleotide sequence of SEQ ID NO.:95.

20. The isolated polynucleotide of claim 18, wherein:
(i) (a) the TCR α-chain encoding polynucleotide comprises the nucleotide sequence of SEQ ID NO.:87; or
(b) the TCR α-chain encoding polynucleotide consists of the nucleotide sequence of SEQ ID NO.:87; and
(ii) (a) the TCR β-chain encoding polynucleotide comprises the nucleotide sequence of SEQ ID NO.:95; or
(b) the TCR β-chain encoding polynucleotide consists of the nucleotide sequence of SEQ ID NO.:95.

21. The isolated polynucleotide of claim 1, wherein the polynucleotide encodes a self-cleaving peptide disposed between the $V_\alpha$ domain encoding polynucleotide and the $V_\beta$ domain encoding polynucleotide.

22. The isolated polynucleotide of claim 21, wherein the polynucleotide has a structure from 5'-end to 3'-end of ($V_\alpha$ domain encoding polynucleotide)-(self-cleaving peptide)-($V_\beta$ domain encoding polynucleotide) or ($V_\beta$ domain encoding polynucleotide)-(self-cleaving peptide)-($V_\alpha$ domain encoding polynucleotide).

23. The isolated polynucleotide of claim 21, wherein the encoded self-cleaving peptide has at least 90% sequence identity to the amino acid sequence of any one of SEQ ID NOS.:17-20 and the polynucleotide encoding the self-cleaving peptide is at least 80% identical to the nucleotide sequence of any one of SEQ ID NOS.:98-102, respectively.

24. The isolated polynucleotide of claim 18, wherein the polynucleotide encodes a self-cleaving peptide disposed between the TCR α-chain encoding polynucleotide and the TCR β-chain encoding polynucleotide.

25. The isolated polynucleotide of claim 24, wherein the polynucleotide has a structure from 5'-end to 3'-end of ($V_\alpha$ domain encoding polynucleotide)-(self-cleaving peptide)-($V_\beta$ domain encoding polynucleotide) or ($V_\beta$ domain encoding polynucleotide)-(self-cleaving peptide)-($V_\alpha$ domain encoding polynucleotide).

26. The isolated polynucleotide of claim 24, wherein the encoded self-cleaving peptide has at least 90% sequence identity to the amino acid sequence of any one of SEQ ID NOS.:17-20 and the polynucleotide encoding the self-cleaving peptide is at least 80% identical to the nucleotide sequence of any one of SEQ ID NOS.:98-102, respectively.

27. The isolated polynucleotide of claim 21, wherein:
(a) the polynucleotide encoding the $V_\alpha$ domain, the self-cleaving peptide, and the $V_\beta$ domain comprises the nucleotide sequence of SEQ ID NO.:96 or 97; or
(b) the polynucleotide encoding the $V_\alpha$ domain, the self-cleaving peptide, and the $V_\beta$ domain consists of the nucleotide sequence of SEQ ID NO.:96 or 97.

28. The isolated polynucleotide of claim 1, wherein the binding protein is a T cell receptor (TCR), a chimeric antigen receptor or an antigen-binding fragment of a TCR.

29. The isolated polynucleotide of claim 1, wherein the binding protein is a TCR and the TCR binds to a RMFP-NAPYL (SEQ ID NO.:16):human leukocyte antigen (HLA) complex with a $K_d$ less than or equal to about 8 nM or less than or equal to about 5 nM.

30. An expression vector, comprising a polynucleotide of claim 1 operably linked to an expression control sequence.

31. The expression vector of claim 30, wherein the vector is capable of delivering the polynucleotide to a host cell.

32. The expression vector of claim 31, wherein the host cell is a hematopoietic progenitor cell or a human immune system cell.

33. The expression vector according to claim 32, wherein the immune system cell is a T cell, a natural killer cell, a dendritic cell, or any combination thereof.

34. The expression vector according to claim 33, wherein the T cell is a naïve T cell, a central memory T cell, an effector memory T cell, or any combination thereof.

35. The expression vector according of claims 31, wherein the vector is a viral vector.

36. The expression vector according to claim 35, wherein the viral vector comprises a lentiviral vector or a retroviral vector.

37. A recombinant host cell, comprising an expression vector of claim 30, wherein the host cell expresses on its cell surface the binding protein encoded by the polynucleotide.

38. An isolated polynucleotide encoding a binding protein, comprising a polynucleotide encoding a human TCR α chain variable (Vα) domain, wherein the polynucleotide encoding the Vα domain comprises the nucleotide sequence of SEQ ID NO.:128; and a polynucleotide encoding a human TCR β chain variable (Vβ) domain, wherein the polynucleotide encoding the Vβ domain comprises the nucleotide sequence of SEQ ID NO.:89.

39. The isolated polynucleotide of claim 38, wherein the polynucleotide encoding the Vα domain consists of the nucleotide sequence of SEQ ID NO.:128 and the polynucleotide encoding the Vβ domain consists of the nucleotide sequence of SEQ ID NO.:89.

40. The isolated polynucleotide of claim 38, further comprising:
(a) a polynucleotide encoding an α-chain constant domain that:
  (i) comprises the nucleotide sequence of SEQ ID NO:84; or
  (ii) consists of the nucleotide sequence of SEQ ID NO:84;
(b) a polynucleotide encoding a β-chain constant domain that:
  (i) comprises the nucleotide sequence of SEQ ID NO:93; or
  (ii) consists of the nucleotide sequence of SEQ ID NO:93; or
(c) a polynucleotide of (a)(i) or (a)(ii), and a polynucleotide of (b)(i) or (b)(ii).

41. The isolated polynucleotide of claim 39, further comprising:
(a) a polynucleotide encoding an α-chain constant domain that:
  (i) comprises of the nucleotide sequence of SEQ ID NO:84; or
  (ii) consists of the nucleotide sequence of SEQ ID NO:84;
(b) a polynucleotide encoding a β-chain constant domain that:
  (i) comprises the nucleotide sequence of SEQ ID NO:93; or
  (ii) consists of the nucleotide sequence of SEQ ID NO:93; or
(c) a polynucleotide of (a)(i) or (a)(ii), and a polynucleotide of (b)(i) or (b)(ii).

42. An isolated polynucleotide comprising the nucleotide sequence of SEQ ID NO:96.

43. An isolated polynucleotide comprising the nucleotide sequence of SEQ ID NO:97.

44. The isolated polynucleotide of claim 38, wherein the encoded binding protein is a T cell receptor (TCR), a chimeric antigen receptor, or an antigen-binding fragment of a TCR.

45. The isolated polynucleotide of claim 1, wherein the encoded $V_\alpha$ domain has at least 90% identity to the amino acid sequence set forth in SEQ ID NO:1 or 2 and the encoded $V_\beta$ has at least 90% identity to the amino acid sequence set forth in SEQ ID NO:9.

46. The isolated polynucleotide of claim 1, wherein the encoded $V_\alpha$ domain has at least 95% identity to the amino acid sequence set forth in SEQ ID NO:1 or 2 and the encoded $V_\beta$ has at least 95% identity to the amino acid sequence set forth in SEQ ID NO:9.

47. The isolated polynucleotide of claim 1, wherein the encoded $V_\alpha$ domain comprises the amino acid sequence set forth in SEQ ID NO:1 or 2 and the encoded $V_\beta$ comprises the amino acid sequence set forth in SEQ ID NO:9.

* * * * *

SEQUENCE LISTING

```
<160> NUMBER OF SEQ ID NOS: 128

<210> SEQ ID NO 1
<211> LENGTH: 129
<212> TYPE: PRT
<213> ORGANISM: Artificial Sequence
<220> FEATURE:
<223> OTHER INFORMATION: C4 alpha chain variable domain

<400> SEQUENCE: 1

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
```

```
                85                  90                  95

Thr Glu Thr Gln Pro Glu Asp Ser Ala Val Tyr Phe Cys Ala Ala Thr
                100                 105                 110

Glu Asp Tyr Gln Leu Ile Trp Gly Ala Gly Thr Lys Leu Ile Ile Lys
            115                 120                 125

Pro

<210> SEQ ID NO 2
<211> LENGTH: 129
<212> TYPE: PRT
<213> ORGANISM: Artificial Sequence
<220> FEATURE:
<223> OTHER INFORMATION: C4 alpha -DLT chain variable domain

<400> SEQUENCE: 2

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Thr
                100                 105                 110

Glu Asp Leu Thr Leu Ile Trp Gly Ala Gly Thr Lys Leu Ile Ile Lys
            115                 120                 125

Pro

<210> SEQ ID NO 3
<211> LENGTH: 141
<212> TYPE: PRT
<213> ORGANISM: Artificial Sequence
<220> FEATURE:
<223> OTHER INFORMATION: (C4alpha, P1, P18) chain constant domain

<400> SEQUENCE: 3

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
            115                 120                 125
```

Gly Phe Asn Leu Leu Met Thr Leu Arg Leu Trp Ser Ser
130                 135                 140

<210> SEQ ID NO 4
<211> LENGTH: 141
<212> TYPE: PRT
<213> ORGANISM: Artificial Sequence
<220> FEATURE:
<223> OTHER INFORMATION: (C4alpha , P1, P18) (T177C, T185C, T184C) chain
      constant domain

<400> SEQUENCE: 4

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 5
<211> LENGTH: 270
<212> TYPE: PRT
<213> ORGANISM: Artificial Sequence
<220> FEATURE:
<223> OTHER INFORMATION: C4alpha  chain

<400> SEQUENCE: 5

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Thr
            100                 105                 110

Glu Asp Tyr Gln Leu Ile Trp Gly Ala Gly Thr Lys Leu Ile Ile Lys
        115                 120                 125

Pro Asp Ile Gln Asn Pro Asp Pro Ala Val Tyr Gln Leu Arg Asp Ser
    130                 135                 140

```
Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
            165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
            195                 200                 205

Ser Ile Ile Pro Glu Asp Thr Phe Phe Pro Ser Pro Glu Ser Ser Cys
            210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
            245                 250                 255

Ala Gly Phe Asn Leu Leu Met Thr Leu Arg Leu Trp Ser Ser
            260                 265                 270

<210> SEQ ID NO 6
<211> LENGTH: 270
<212> TYPE: PRT
<213> ORGANISM: Artificial Sequence
<220> FEATURE:
<223> OTHER INFORMATION: C4alpha (T177C) chain

<400> SEQUENCE: 6

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Arg Pro Gln
        50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Thr
            100                 105                 110

Glu Asp Tyr Gln Leu Ile Trp Gly Ala Gly Thr Lys Leu Ile Ile Lys
            115                 120                 125

Pro Asp Ile Gln Asn Pro Asp Pro Ala Val Tyr Gln Leu Arg Asp Ser
            130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
            165                 170                 175

Cys Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
            195                 200                 205

Ser Ile Ile Pro Glu Asp Thr Phe Phe Pro Ser Pro Glu Ser Ser Cys
            210                 215                 220

Asp Val Lys Leu Val Glu Lys Ser Phe Glu Thr Asp Thr Asn Leu Asn
225                 230                 235                 240
```

```
Phe Gln Asn Leu Ser Val Ile Gly Phe Arg Ile Leu Leu Leu Lys Val
            245                 250                 255

Ala Gly Phe Asn Leu Leu Met Thr Leu Arg Leu Trp Ser Ser
            260                 265                 270
```

<210> SEQ ID NO 7
<211> LENGTH: 270
<212> TYPE: PRT
<213> ORGANISM: Artificial Sequence
<220> FEATURE:
<223> OTHER INFORMATION: C4alpha -DLT chain

<400> SEQUENCE: 7

```
Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Thr
            100                 105                 110

Glu Asp Leu Thr Leu Ile Trp Gly Ala Gly Thr Lys Leu Ile Ile Lys
        115                 120                 125

Pro Asp Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 8
<211> LENGTH: 270
<212> TYPE: PRT
<213> ORGANISM: Artificial Sequence
<220> FEATURE:
<223> OTHER INFORMATION: C4alpha -DLT (T177C) chain

<400> SEQUENCE: 8

```
Met Thr Ser Ile Arg Ala Val Phe Ile Phe Leu Trp Leu Gln Leu Asp
1               5                   10                  15
```

-continued

```
Leu Val Asn Gly Glu Asn Val Glu Gln His Pro Ser Thr Leu Ser Val
             20                  25                  30

Gln Glu Gly Asp Ser Ala Val Ile Lys Cys Thr Tyr Ser Asp Ser Ala
         35                  40                  45

Ser Asn Tyr Phe Pro Trp Tyr Lys Gln Glu Leu Gly Lys Arg Pro Gln
 50                  55                  60

Leu Ile Ile Asp Ile Arg Ser Asn Val Gly Glu Lys Lys Asp Gln Arg
 65                  70                  75                  80

Ile Ala Val Thr Leu Asn Lys Thr Ala Lys His Phe Ser Leu His Ile
                 85                  90                  95

Thr Glu Thr Gln Pro Glu Asp Ser Ala Val Tyr Phe Cys Ala Ala Thr
            100                 105                 110

Glu Asp Leu Thr Leu Ile Trp Gly Ala Gly Thr Lys Leu Ile Ile Lys
            115                 120                 125

Pro Asp Ile Gln Asn Pro Asp Pro Ala Val Tyr Gln Leu Arg Asp Ser
130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Cys Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
            195                 200                 205

Ser Ile Ile Pro Glu Asp Thr Phe Phe Pro Ser Pro Glu Ser Ser Cys
210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 9
<211> LENGTH: 131
<212> TYPE: PRT
<213> ORGANISM: Artificial Sequence
<220> FEATURE:
<223> OTHER INFORMATION: C4beta chain variable domain

<400> SEQUENCE: 9

Met Ser Asn Gln Val Leu Cys Cys Val Val Leu Cys Phe Leu Gly Ala
 1               5                  10                  15

Asn Thr Val Asp Gly Gly Ile Thr Gln Ser Pro Lys Tyr Leu Phe Arg
                20                  25                  30

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
 50                  55                  60

Ile Tyr Tyr Ser Gln Ile Val Asn Asp Phe Gln Lys Gly Asp Ile Ala
 65                  70                  75                  80

Glu Gly Tyr Ser Val Ser Arg Glu Lys Lys Glu Ser Phe Pro Leu Thr
                 85                  90                  95

Val Thr Ser Ala Gln Lys Asn Pro Thr Ala Phe Tyr Leu Cys Ala Ser
            100                 105                 110
```

```
Ser Pro Gly Ala Leu Tyr Glu Gln Tyr Phe Gly Pro Gly Thr Arg Leu
        115                 120                 125

Thr Val Thr
    130

<210> SEQ ID NO 10
<211> LENGTH: 179
<212> TYPE: PRT
<213> ORGANISM: Artificial Sequence
<220> FEATURE:
<223> OTHER INFORMATION: (C4, P1, P15, P22)beta chain constant domain

<400> SEQUENCE: 10

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 11
<211> LENGTH: 179
<212> TYPE: PRT
<213> ORGANISM: Artificial Sequence
<220> FEATURE:
<223> OTHER INFORMATION: (C4, P1, P15, P22)beta chain (S188C, S191C,
      S190C, S186C) constant domain

<400> SEQUENCE: 11

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
```

```
                        85                  90                  95
Gln Val Gln Phe Tyr Gly Leu Ser Glu Asn Asp Glu Trp Thr Gln Asp
                    100                 105                 110

Arg Ala Lys Pro Val Thr Gln Ile Val Ser Ala Glu Ala Trp Gly Arg
                115                 120                 125

Ala Asp Cys Gly Phe Thr Ser Glu Ser Tyr Gln Gln Gly Val Leu Ser
            130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                    165                 170                 175

Ser Arg Gly

<210> SEQ ID NO 12
<211> LENGTH: 310
<212> TYPE: PRT
<213> ORGANISM: Artificial Sequence
<220> FEATURE:
<223> OTHER INFORMATION: C4beta  chain

<400> SEQUENCE: 12

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
                20                  25                  30

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
        50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
                100                 105                 110

Ser Pro Gly Ala Leu Tyr Glu Gln Tyr Phe Gly Pro Gly Thr Arg Leu
            115                 120                 125

Thr Val Thr Glu Asp Leu Lys Asn Val Phe Pro Pro Glu Val Ala Val
        130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270
```

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
290                 295                 300

Arg Lys Asp Ser Arg Gly
305                 310

<210> SEQ ID NO 13
<211> LENGTH: 310
<212> TYPE: PRT
<213> ORGANISM: Artificial Sequence
<220> FEATURE:
<223> OTHER INFORMATION: C4beta (S188C) chain

<400> SEQUENCE: 13

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Pro Gly Ala Leu Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 14
<211> LENGTH: 602
<212> TYPE: PRT
<213> ORGANISM: Artificial Sequence
<220> FEATURE:
<223> OTHER INFORMATION: C4beta (S188C)-P2A-C4alpha (T177C)

<400> SEQUENCE: 14

```
Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Pro Gly Ala Leu Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly Gly Ser Gly Ala Thr Asn Phe Ser Leu Leu
305                 310                 315                 320

Lys Gln Ala Gly Asp Val Glu Glu Asn Pro Gly Pro Met Thr Ser Ile
                325                 330                 335

Arg Ala Val Phe Ile Phe Leu Trp Leu Gln Leu Asp Leu Val Asn Gly
            340                 345                 350

Glu Asn Val Glu Gln His Pro Ser Thr Leu Ser Val Gln Glu Gly Asp
        355                 360                 365
```

```
Ser Ala Val Ile Lys Cys Thr Tyr Ser Asp Ser Ala Ser Asn Tyr Phe
    370                 375                 380

Pro Trp Tyr Lys Gln Glu Leu Gly Lys Arg Pro Gln Leu Ile Ile Asp
385                 390                 395                 400

Ile Arg Ser Asn Val Gly Glu Lys Lys Asp Gln Arg Ile Ala Val Thr
                405                 410                 415

Leu Asn Lys Thr Ala Lys His Phe Ser Leu His Ile Thr Glu Thr Gln
                420                 425                 430

Pro Glu Asp Ser Ala Val Tyr Phe Cys Ala Ala Thr Glu Asp Tyr Gln
            435                 440                 445

Leu Ile Trp Gly Ala Gly Thr Lys Leu Ile Ile Lys Pro Asp Ile Gln
    450                 455                 460

Asn Pro Asp Pro Ala Val Tyr Gln Leu Arg Asp Ser Lys Ser Ser Asp
465                 470                 475                 480

Lys Ser Val Cys Leu Phe Thr Asp Phe Asp Ser Gln Thr Asn Val Ser
                485                 490                 495

Gln Ser Lys Asp Ser Asp Val Tyr Ile Thr Asp Lys Cys Val Leu Asp
                500                 505                 510

Met Arg Ser Met Asp Phe Lys Ser Asn Ser Ala Val Ala Trp Ser Asn
            515                 520                 525

Lys Ser Asp Phe Ala Cys Ala Asn Ala Phe Asn Asn Ser Ile Ile Pro
    530                 535                 540

Glu Asp Thr Phe Phe Pro Ser Pro Glu Ser Ser Cys Asp Val Lys Leu
545                 550                 555                 560

Val Glu Lys Ser Phe Glu Thr Asp Thr Asn Leu Asn Phe Gln Asn Leu
                565                 570                 575

Ser Val Ile Gly Phe Arg Ile Leu Leu Leu Lys Val Ala Gly Phe Asn
            580                 585                 590

Leu Leu Met Thr Leu Arg Leu Trp Ser Ser
    595                 600

<210> SEQ ID NO 15
<211> LENGTH: 602
<212> TYPE: PRT
<213> ORGANISM: Artificial Sequence
<220> FEATURE:
<223> OTHER INFORMATION: C4beta (S188C)-P2A-C4alpha-DLT (T177C)

<400> SEQUENCE: 15

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
                20                  25                  30

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
                100                 105                 110

Ser Pro Gly Ala Leu Tyr Glu Gln Tyr Phe Gly Pro Gly Thr Arg Leu
            115                 120                 125
```

```
Thr Val Thr Glu Asp Leu Lys Asn Val Phe Pro Glu Val Ala Val
    130                 135                 140
Phe Glu Pro Ser Glu Ala Glu Ile Ser His Thr Gln Lys Ala Thr Leu
145                 150                 155                 160
Val Cys Leu Ala Thr Gly Phe Tyr Pro Asp His Val Glu Leu Ser Trp
                    165                 170                 175
Trp Val Asn Gly Lys Glu Val His Ser Gly Val Cys Thr Asp Pro Gln
                180                 185                 190
Pro Leu Lys Glu Gln Pro Ala Leu Asn Asp Ser Arg Tyr Cys Leu Ser
            195                 200                 205
Ser Arg Leu Arg Val Ser Ala Thr Phe Trp Gln Asn Pro Arg Asn His
210                 215                 220
Phe Arg Cys Gln Val Gln Phe Tyr Gly Leu Ser Glu Asn Asp Glu Trp
225                 230                 235                 240
Thr Gln Asp Arg Ala Lys Pro Val Thr Gln Ile Val Ser Ala Glu Ala
                245                 250                 255
Trp Gly Arg Ala Asp Cys Gly Phe Thr Ser Glu Ser Tyr Gln Gln Gly
                260                 265                 270
Val Leu Ser Ala Thr Ile Leu Tyr Glu Ile Leu Leu Gly Lys Ala Thr
            275                 280                 285
Leu Tyr Ala Val Leu Val Ser Ala Leu Val Leu Met Ala Met Val Lys
    290                 295                 300
Arg Lys Asp Ser Arg Gly Gly Ser Gly Ala Thr Asn Phe Ser Leu Leu
305                 310                 315                 320
Lys Gln Ala Gly Asp Val Glu Glu Asn Pro Gly Pro Met Thr Ser Ile
                325                 330                 335
Arg Ala Val Phe Ile Phe Leu Trp Leu Gln Leu Asp Leu Val Asn Gly
                340                 345                 350
Glu Asn Val Glu Gln His Pro Ser Thr Leu Ser Val Gln Glu Gly Asp
            355                 360                 365
Ser Ala Val Ile Lys Cys Thr Tyr Ser Asp Ser Ala Ser Asn Tyr Phe
370                 375                 380
Pro Trp Tyr Lys Gln Glu Leu Gly Lys Arg Pro Gln Leu Ile Ile Asp
385                 390                 395                 400
Ile Arg Ser Asn Val Gly Glu Lys Lys Asp Gln Arg Ile Ala Val Thr
                405                 410                 415
Leu Asn Lys Thr Ala Lys His Phe Ser Leu His Ile Thr Glu Thr Gln
                420                 425                 430
Pro Glu Asp Ser Ala Val Tyr Phe Cys Ala Ala Thr Glu Asp Leu Thr
            435                 440                 445
Leu Ile Trp Gly Ala Gly Thr Lys Leu Ile Ile Lys Pro Asp Ile Gln
    450                 455                 460
Asn Pro Asp Pro Ala Val Tyr Gln Leu Arg Asp Ser Lys Ser Ser Asp
465                 470                 475                 480
Lys Ser Val Cys Leu Phe Thr Asp Phe Asp Ser Gln Thr Asn Val Ser
                485                 490                 495
Gln Ser Lys Asp Ser Asp Val Tyr Ile Thr Asp Lys Cys Val Leu Asp
            500                 505                 510
Met Arg Ser Met Asp Phe Lys Ser Asn Ser Ala Val Ala Trp Ser Asn
    515                 520                 525
Lys Ser Asp Phe Ala Cys Ala Asn Ala Phe Asn Asn Ser Ile Ile Pro
530                 535                 540
```

```
Glu Asp Thr Phe Phe Pro Ser Pro Glu Ser Ser Cys Asp Val Lys Leu
545                 550                 555                 560

Val Glu Lys Ser Phe Glu Thr Asp Thr Asn Leu Asn Phe Gln Asn Leu
                565                 570                 575

Ser Val Ile Gly Phe Arg Ile Leu Leu Lys Val Ala Gly Phe Asn
            580                 585                 590

Leu Leu Met Thr Leu Arg Leu Trp Ser Ser
        595                 600

<210> SEQ ID NO 16
<211> LENGTH: 9
<212> TYPE: PRT
<213> ORGANISM: Artificial Sequence
<220> FEATURE:
<223> OTHER INFORMATION: WT-1 Peptide Antigen

<400> SEQUENCE: 16

Arg Met Phe Pro Asn Ala Pro Tyr Leu
1               5

<210> SEQ ID NO 17
<211> LENGTH: 22
<212> TYPE: PRT
<213> ORGANISM: Artificial Sequence
<220> FEATURE:
<223> OTHER INFORMATION: Porcine teschovirus-1 2A (P2A) peptide

<400> SEQUENCE: 17

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 18
<211> LENGTH: 21
<212> TYPE: PRT
<213> ORGANISM: Artificial Sequence
<220> FEATURE:
<223> OTHER INFORMATION: Thoseaasigna virus 2A (T2A) peptide

<400> SEQUENCE: 18

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 19
<211> LENGTH: 23
<212> TYPE: PRT
<213> ORGANISM: Artificial Sequence
<220> FEATURE:
<223> OTHER INFORMATION: Equine rhinitis A virus (ERAV) 2A (E2A) peptide

<400> SEQUENCE: 19

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 20
<211> LENGTH: 25
<212> TYPE: PRT
<213> ORGANISM: Artificial Sequence
<220> FEATURE:
```

<223> OTHER INFORMATION: Foot-and-Mouth disease virus 2A (F2A) peptide

<400> SEQUENCE: 20

Gly Ser

Leu Ile Ile Lys Pro
    130

<210> SEQ ID NO 23
<211> LENGTH: 6
<212> TYPE: PRT
<213> ORGANISM: Artificial Sequence
<220> FEATURE:
<223> OTHER INFORMATION: C4alpha CDR1

<400> SEQUENCE: 23

Asp Ser Ala Ser Asn Tyr
1               5

<210> SEQ ID NO 24
<211> LENGTH: 7
<212> TYPE: PRT
<213> ORGANISM: Artificial Sequence
<220> FEATURE:
<223> OTHER INFORMATION: C4alpha CDR2

<400> SEQUENCE: 24

Ile Arg Ser Asn Val Gly Glu
1               5

<210> SEQ ID NO 25
<211> LENGTH: 11
<212> TYPE: PRT
<213> ORGANISM: Artificial Sequence
<220> FEATURE:
<223> OTHER INFORMATION: C4alpha (DYQ) CDR3

<400> SEQUENCE: 25

Cys Ala Ala Thr Glu Asp Tyr Gln Leu Ile Trp
1               5                   10

<210> SEQ ID NO 26
<211> LENGTH: 11
<212> TYPE: PRT
<213> ORGANISM: Artificial Sequence
<220> FEATURE:
<223> OTHER INFORMATION: C4alpha (DLT) CDR3

<400> SEQUENCE: 26

Cys Ala Ala Thr Glu Asp Leu Thr Leu Ile Trp
1               5                   10

<210> SEQ ID NO 27
<211> LENGTH: 5
<212> TYPE: PRT
<213> ORGANISM: Artificial Sequence
<220> FEATURE:
<223> OTHER INFORMATION: C4beta CDR1

<400> SEQUENCE: 27

Leu Asn His Asp Ala
1               5

<210> SEQ ID NO 28
<211> LENGTH: 6
<212> TYPE: PRT
<213> ORGANISM: Artificial Sequence
<220> FEATURE:
<223> OTHER INFORMATION: C4beta CD2

<400> SEQUENCE: 28

Ser Gln Ile Val Asn Asp
1               5

<210> SEQ ID NO 29
<211> LENGTH: 13
<212> TYPE: PRT
<213> ORGANISM: Artificial Sequence
<220> FEATURE:
<223> OTHER INFORMATION: C4beta CDR3

<400> SEQUENCE: 29

Cys Ala Ser Ser Pro Gly Ala Leu Tyr Glu Gln Tyr Phe
1               5                   10

<210> SEQ ID NO 30
<211> LENGTH: 7
<212> TYPE: PRT
<213> ORGANISM: Artificial Sequence
<220> FEATURE:
<223> OTHER INFORMATION: P1alpha CDR1

<400> SEQUENCE: 30

Thr Arg Asp Thr Thr Tyr Tyr
1               5

<210> SEQ ID NO 31
<211> LENGTH: 7
<212> TYPE: PRT
<213> ORGANISM: Artificial Sequence
<220> FEATURE:
<223> OTHER INFORMATION: P1alpha CDR2

<400> SEQUENCE: 31

Arg Asn Ser Phe Asp Glu Gln
1               5

<210> SEQ ID NO 32
<211> LENGTH: 16
<212> TYPE: PRT
<213> ORGANISM: Artificial Sequence
<220> FEATURE:
<223> OTHER INFORMATION: P1alpha CDR3

<400> SEQUENCE: 32

Cys Ala Leu Ser Glu Ala His Arg Asp Ser Asn Tyr Gln Leu Ile Trp
1               5                   10                  15

<210> SEQ ID NO 33
<211> LENGTH: 5
<212> TYPE: PRT
<213> ORGANISM: Artificial Sequence
<220> FEATURE:
<223> OTHER INFORMATION: P1beta CDR1

<400> SEQUENCE: 33

Leu Gly His Asn Ala
1               5

<210> SEQ ID NO 34
<211> LENGTH: 6
<212> TYPE: PRT
<213> ORGANISM: Artificial Sequence
<220> FEATURE:
<223> OTHER INFORMATION: P1beta CD2

<400> SEQUENCE: 34

```
Tyr Asn Phe Lys Glu Gln
1               5

<210> SEQ ID NO 35
<211> LENGTH: 15
<212> TYPE: PRT
<213> ORGANISM: Artificial Sequence
<220> FEATURE:
<223> OTHER INFORMATION: P1beta CDR3

<400> SEQUENCE: 35

Cys Ala Ser Ser Gln Asp Glu Gln Phe Leu Tyr Asn Glu Gln Phe
1               5                   10                  15

<210> SEQ ID NO 36
<211> LENGTH: 6
<212> TYPE: PRT
<213> ORGANISM: Artificial Sequence
<220> FEATURE:
<223> OTHER INFORMATION: P15alpha CDR1

<400> SEQUENCE: 36

Asn Thr Ala Phe Asp Tyr
1               5

<210> SEQ ID NO 37
<211> LENGTH: 7
<212> TYPE: PRT
<213> ORGANISM: Artificial Sequence
<220> FEATURE:
<223> OTHER INFORMATION: P15alpha CDR2

<400> SEQUENCE: 37

Ile Arg Pro Asp Val Ser Glu
1               5

<210> SEQ ID NO 38
<211> LENGTH: 15
<212> TYPE: PRT
<213> ORGANISM: Artificial Sequence
<220> FEATURE:
<223> OTHER INFORMATION: P15alpha CDR3

<400> SEQUENCE: 38

Cys Ala Ala Ser Pro Gln Gly Ala Gly Ser Tyr Gln Leu Thr Phe
1               5                   10                  15

<210> SEQ ID NO 39
<211> LENGTH: 5
<212> TYPE: PRT
<213> ORGANISM: Artificial Sequence
<220> FEATURE:
<223> OTHER INFORMATION: P15beta CDR1

<400> SEQUENCE: 39

Ser Glu His Asn Arg
1               5

<210> SEQ ID NO 40
<211> LENGTH: 6
<212> TYPE: PRT
<213> ORGANISM: Artificial Sequence
<220> FEATURE:
<223> OTHER INFORMATION: P15beta CD2

<400> SEQUENCE: 40

Phe Gln Asn Glu Ala Gln
1               5
```

```
1               5
```

<210> SEQ ID NO 41
<211> LENGTH: 14
<212> TYPE: PRT
<213> ORGANISM: Artificial Sequence
<220> FEATURE:
<223> OTHER INFORMATION: P15beta CDR3

<400> SEQUENCE: 41

```
Cys Ala Ser Ser Leu Ala Tyr Gly Lys Asp Thr Gln Tyr Phe
1               5                   10
```

<210> SEQ ID NO 42
<211> LENGTH: 7
<212> TYPE: PRT
<213> ORGANISM: Artificial Sequence
<220> FEATURE:
<223> OTHER INFORMATION: P18alpha CDR1

<400> SEQUENCE: 42

```
Thr Ser Asp Gln Ser Tyr Gly
1               5
```

<210> SEQ ID NO 43
<211> LENGTH: 7
<212> TYPE: PRT
<213> ORGANISM: Artificial Sequence
<220> FEATURE:
<223> OTHER INFORMATION: P18alpha CDR2

<400> SEQUENCE: 43

```
Gln Gly Ser Tyr Asp Glu Gln
1               5
```

<210> SEQ ID NO 44
<211> LENGTH: 15
<212> TYPE: PRT
<213> ORGANISM: Artificial Sequence
<220> FEATURE:
<223> OTHER INFORMATION: P18alpha CDR3

<400> SEQUENCE: 44

```
Cys Ala Ile Pro Thr Leu Met Asp Ser Asn Tyr Gln Leu Ile Trp
1               5                   10                  15
```

<210> SEQ ID NO 45
<211> LENGTH: 5
<212> TYPE: PRT
<213> ORGANISM: Artificial Sequence
<220> FEATURE:
<223> OTHER INFORMATION: P18beta CDR1

<400> SEQUENCE: 45

```
Ser Gly His Asp Tyr
1               5
```

<210> SEQ ID NO 46
<211> LENGTH: 6
<212> TYPE: PRT
<213> ORGANISM: Artificial Sequence
<220> FEATURE:
<223> OTHER INFORMATION: P18beta CD2

<400> SEQUENCE: 46

```
Phe Asn Asn Asn Val Pro
1               5
```

<210> SEQ ID NO 47
<211> LENGTH: 11
<212> TYPE: PRT
<213> ORGANISM: Artificial Sequence
<220> FEATURE:
<223> OTHER INFORMATION: P18beta CDR3

<400> SEQUENCE: 47

Cys Ala Ser Ser Val Ser Gly Ser Glu Ala Phe
1               5                   10

<210> SEQ ID NO 48
<211> LENGTH: 6
<212> TYPE: PRT
<213> ORGANISM: Artificial Sequence
<220> FEATURE:
<223> OTHER INFORMATION: (P20, P22)alpha CDR1

<400> SEQUENCE: 48

Asp Arg Gly Ser Gln Ser
1               5

<210> SEQ ID NO 49
<211> LENGTH: 7
<212> TYPE: PRT
<213> ORGANISM: Artificial Sequence
<220> FEATURE:
<223> OTHER INFORMATION: (P20, P22)alpha CDR2

<400> SEQUENCE: 49

Ser Ile Tyr Ser Asn Gly Asp
1               5

<210> SEQ ID NO 50
<211> LENGTH: 11
<212> TYPE: PRT
<213> ORGANISM: Artificial Sequence
<220> FEATURE:
<223> OTHER INFORMATION: P20alpha CDR3

<400> SEQUENCE: 50

Cys Ala Val Leu Glu Gly Gln Lys Leu Leu Phe
1               5                   10

<210> SEQ ID NO 51
<211> LENGTH: 12
<212> TYPE: PRT
<213> ORGANISM: Artificial Sequence
<220> FEATURE:
<223> OTHER INFORMATION: P22alpha CDR3

<400> SEQUENCE: 51

Cys Ala Ala Asn Asn Ala Gly Asn Met Leu Thr Phe
1               5                   10

<210> SEQ ID NO 52
<211> LENGTH: 5
<212> TYPE: PRT
<213> ORGANISM: Artificial Sequence
<220> FEATURE:
<223> OTHER INFORMATION: (P20, P22)beta CDR1

<400> SEQUENCE: 52

Met Asp His Glu Asn
1               5

<210> SEQ ID NO 53
<211> LENGTH: 6
<212> TYPE: PRT
<213> ORGANISM: Artificial Sequence
<220> FEATURE:
<223> OTHER INFORMATION: (P20, P22)beta CD2

<400> SEQUENCE: 53

Ser Tyr Asp Val Lys Met
1               5

<210> SEQ ID NO 54
<211> LENGTH: 10
<212> TYPE: PRT
<213> ORGANISM: Artificial Sequence
<220> FEATURE:
<223> OTHER INFORMATION: P20beta CDR3

<400> SEQUENCE: 54

Cys Ala Thr Ser His Gln Pro Gln His Phe
1               5                   10

<210> SEQ ID NO 55
<211> LENGTH: 10
<212> TYPE: PRT
<213> ORGANISM: Artificial Sequence
<220> FEATURE:
<223> OTHER INFORMATION: P22beta CDR3

<400> SEQUENCE: 55

Cys Ala Ser Ser Ser Ile Asn Glu Gln Phe
1               5                   10

<210> SEQ ID NO 56
<211> LENGTH: 137
<212> TYPE: PRT
<213> ORGANISM: Artificial Sequence
<220> FEATURE:
<223> OTHER INFORMATION: P1alpha chain variable domain

<400> SEQUENCE: 56

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Glu Ala His Arg Asp Ser Asn Tyr Gln Leu Ile Trp Gly
        115                 120                 125

Ala Gly Thr Lys Leu Ile Ile Lys Pro
    130                 135

<210> SEQ ID NO 57
<211> LENGTH: 142

<212> TYPE: PRT
<213> ORGANISM: Artificial Sequence
<220> FEATURE:
<223> OTHER INFORMATION: P15alpha chain variable domain

<400> SEQUENCE: 57

Met Asp Lys Ile Leu Gly Ala Ser Phe Leu Val Leu Trp Leu Gln Leu
1               5                   10                  15

Cys Trp Val Ser Gly Gln Gln Lys Glu Lys Ser Asp Gln Gln Gln Val
            20                  25                  30

Lys Gln Ser Pro Gln Ser Leu Ile Val Gln Lys Gly Gly Ile Ser Ile
        35                  40                  45

Ile Asn Cys Ala Tyr Glu Asn Thr Ala Phe Asp Tyr Phe Pro Trp Tyr
50                  55                  60

Gln Gln Phe Pro Gly Lys Gly Pro Ala Leu Leu Ile Ala Ile Arg Pro
65                  70                  75                  80

Asp Val Ser Glu Lys Lys Glu Gly Arg Phe Thr Ile Ser Phe Asn Lys
                85                  90                  95

Ser Ala Lys Gln Phe Ser Leu His Ile Met Asp Ser Gln Pro Gly Asp
            100                 105                 110

Ser Ala Thr Tyr Phe Cys Ala Ala Ser Pro Gly Ala Gly Ser Tyr
        115                 120                 125

Gln Leu Thr Phe Gly Lys Gly Thr Lys Leu Ser Val Ile Pro
    130                 135                 140

<210> SEQ ID NO 58
<211> LENGTH: 136
<212> TYPE: PRT
<213> ORGANISM: Artificial Sequence
<220> FEATURE:
<223> OTHER INFORMATION: P18alpha chain variable domain

<400> SEQUENCE: 58

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Ile Pro Thr Leu Met Asp Ser Asn Tyr Gln Leu Ile Trp Gly Ala
        115                 120                 125

Gly Thr Lys Leu Ile Ile Lys Pro
    130                 135

<210> SEQ ID NO 59
<211> LENGTH: 131
<212> TYPE: PRT
<213> ORGANISM: Artificial Sequence
<220> FEATURE:
<223> OTHER INFORMATION: P20alpha chain variable domain -continued

```
<400> SEQUENCE: 59

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Leu Glu Gly Gln Lys Leu Leu Phe Ala Arg Gly Thr Met Leu Lys
        115                 120                 125

Val Asp Leu
    130

<210> SEQ ID NO 60
<211> LENGTH: 132
<212> TYPE: PRT
<213> ORGANISM: Artificial Sequence
<220> FEATURE:
<223> OTHER INFORMATION: P22alpha chain variable domain

<400> SEQUENCE: 60

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Val Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Ala Asn Asn Ala Gly Asn Met Leu Thr Phe Gly Gly Gly Thr Arg Leu
        115                 120                 125

Met Val Lys Pro
    130

<210> SEQ ID NO 61
<211> LENGTH: 141
<212> TYPE: PRT
<213> ORGANISM: Artificial Sequence
<220> FEATURE:
<223> OTHER INFORMATION: (P15, P20)alpha chain constant domain

<400> SEQUENCE: 61

Asn Ile Gln Asn Pro Asp Pro Ala Val Tyr Gln Leu Arg Asp Ser Lys
1               5                   10                  15
```

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
            50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Thr Asn Leu Asn Phe
            100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
            130                 135                 140

<210> SEQ ID NO 62
<211> LENGTH: 141
<212> TYPE: PRT
<213> ORGANISM: Artificial Sequence
<220> FEATURE:
<223> OTHER INFORMATION: (P15, P20)alpha chain

<400> SEQUENCE: 62

Asn Ile Gln Asn Pro Asp Pro Ala Val Tyr Gln Leu Arg Asp Ser Lys
 1               5                  10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Cys
            35                  40                  45

Val Leu Asp Met Arg Ser Met Asp Phe Lys Ser Asn Ser Ala Val Ala
            50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Thr Asn Leu Asn Phe
            100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
            130                 135                 140

<210> SEQ ID NO 63
<211> LENGTH: 141
<212> TYPE: PRT
<213> ORGANISM: Artificial Sequence
<220> FEATURE:
<223> OTHER INFORMATION: P22alpha chain constant domain

<400> SEQUENCE: 63

His Ile Gln Asn Pro Asp Pro Ala Val Tyr Gln Leu Arg Asp Ser Lys
 1               5                  10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                 85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 64
<211> LENGTH: 141
<212> TYPE: PRT
<213> ORGANISM: Artificial Sequence
<220> FEATURE:
<223> OTHER INFORMATION: P22alpha chain (T180C) constant domain

<400> SEQUENCE: 64

His Ile Gln Asn Pro Asp Pro Ala Val Tyr Gln Leu Arg Asp Ser Lys
 1               5                  10                  15

Ser Ser Asp Lys Ser Val Cys Leu Phe Thr Asp Phe Asp Ser Gln Thr
             20                  25                  30

Asn Val Ser Gln Ser Lys Asp Ser Asp Val Tyr Ile Thr Asp Lys Cys
         35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                 85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 65
<211> LENGTH: 134
<212> TYPE: PRT
<213> ORGANISM: Artificial Sequence
<220> FEATURE:
<223> OTHER INFORMATION: P1beta chain variable domain

<400> SEQUENCE: 65

Met Gly Cys Arg Leu Leu Cys Cys Ala Val Leu Cys Leu Leu Gly Ala
 1               5                  10                  15

Val Pro Met Glu Thr Gly Val Thr Gln Thr Pro Arg His Leu Val Met
             20                  25                  30

Gly Met Thr Asn Lys Lys Ser Leu Lys Cys Glu Gln His Leu Gly His
         35                  40                  45

Asn Ala Met Tyr Trp Tyr Lys Gln Ser Ala Lys Lys Pro Leu Glu Leu
    50                  55                  60

Met Phe Val Tyr Asn Phe Lys Glu Gln Thr Glu Asn Asn Ser Val Pro

```
                65                  70                  75                  80
Ser Arg Phe Ser Pro Glu Cys Pro Asn Ser Ser His Leu Phe Leu His
                    85                  90                  95

Leu His Thr Leu Gln Pro Glu Asp Ser Ala Leu Tyr Leu Cys Ala Ser
                    100                 105                 110

Ser Gln Asp Glu Gln Phe Leu Tyr Asn Glu Gln Phe Phe Gly Pro Gly
                    115                 120                 125

Thr Arg Leu Thr Val Leu
                    130

<210> SEQ ID NO 66
<211> LENGTH: 133
<212> TYPE: PRT
<213> ORGANISM: Artificial Sequence
<220> FEATURE:
<223> OTHER INFORMATION: P15beta  chain variable domain

<400> SEQUENCE: 66

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
                20                  25                  30

Lys Arg Gly Gln Asn Val Thr Phe Arg Cys Asp Pro Ile Ser Glu His
                35                  40                  45

Asn Arg Leu Tyr Trp Tyr Arg Gln Thr Leu Gly Gln Gly Pro Glu Phe
                50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                    85                  90                  95

Glu Ile Gln Arg Thr Glu Gln Gly Asp Ser Ala Met Tyr Leu Cys Ala
                    100                 105                 110

Ser Ser Leu Ala Tyr Gly Lys Asp Thr Gln Tyr Phe Gly Pro Gly Thr
                    115                 120                 125

Arg Leu Thr Val Leu
                    130

<210> SEQ ID NO 67
<211> LENGTH: 131
<212> TYPE: PRT
<213> ORGANISM: Artificial Sequence
<220> FEATURE:
<223> OTHER INFORMATION: P18beta chain variable domain

<400> SEQUENCE: 67

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
                35                  40                  45

Asp Tyr Leu Phe Trp Tyr Arg Gln Thr Met Met Arg Gly Leu Glu Leu
                50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                    85                  90                  95
```

```
Lys Ile Gln Pro Ser Glu Pro Arg Asp Ser Ala Val Tyr Phe Cys Ala
            100                 105                 110

Ser Ser Val Ser Gly Ser Glu Ala Phe Phe Gly Gln Gly Thr Arg Leu
        115                 120                 125

Thr Val Val
        130

<210> SEQ ID NO 68
<211> LENGTH: 128
<212> TYPE: PRT
<213> ORGANISM: Artificial Sequence
<220> FEATURE:
<223> OTHER INFORMATION: P20beta chain variable domain

<400> SEQUENCE: 68

Met Gly Ile Arg Leu Leu Cys Arg Val Ala Phe Cys Phe Leu Ala Val
  1               5                  10                  15

Gly Leu Val Asp Val Lys Val Thr Gln Ser Ser Arg Tyr Leu Val Lys
             20                  25                  30

Arg Thr Gly Glu Lys Val Phe Leu Glu Cys Val Gln Asp Met Asp His
         35                  40                  45

Glu Asn Met Phe Trp Tyr Arg Gln Asp Pro Gly Leu Gly Leu Arg Leu
     50                  55                  60

Ile Tyr Phe Ser Tyr Asp Val Lys Met Lys Glu Lys Gly Asp Ile Pro
 65                  70                  75                  80

Glu Gly Tyr Ser Val Ser Arg Glu Lys Lys Glu Arg Phe Ser Leu Ile
                 85                  90                  95

Leu Glu Ser Ala Ser Thr Asn Gln Thr Ser Met Tyr Leu Cys Ala Thr
            100                 105                 110

Ser His Gln Pro Gln His Phe Gly Asp Gly Thr Arg Leu Ser Ile Leu
        115                 120                 125

<210> SEQ ID NO 69
<211> LENGTH: 129
<212> TYPE: PRT
<213> ORGANISM: Artificial Sequence
<220> FEATURE:
<223> OTHER INFORMATION: P22beta chain variable domain

<400> SEQUENCE: 69

Met Gly Ile Arg Leu Leu Cys Arg Val Ala Phe Cys Phe Leu Ala Val
  1               5                  10                  15

Gly Leu Val Asp Val Lys Val Thr Gln Ser Ser Arg Tyr Leu Val Lys
             20                  25                  30

Arg Thr Gly Glu Lys Val Phe Leu Glu Cys Val Gln Asp Met Asp His
         35                  40                  45

Glu Asn Met Phe Trp Tyr Arg Gln Asp Pro Gly Leu Gly Leu Arg Leu
     50                  55                  60

Ile Tyr Phe Ser Tyr Asp Val Lys Met Lys Glu Lys Gly Asp Ile Pro
 65                  70                  75                  80

Glu Gly Tyr Ser Val Ser Arg Glu Lys Lys Glu Arg Phe Ser Leu Ile
                 85                  90                  95

Leu Glu Ser Ala Ser Thr Asn Gln Thr Ser Met Tyr Leu Cys Ala Ser
            100                 105                 110

Ser Ser Ile Asn Glu Gln Phe Phe Gly Pro Gly Thr Arg Leu Thr Val
        115                 120                 125

Leu
```

<210> SEQ ID NO 70
<211> LENGTH: 177
<212> TYPE: PRT
<213> ORGANISM: Artificial Sequence
<220> FEATURE:
<223> OTHER INFORMATION: (P18, P20)beta chain constant domain

<400> SEQUENCE: 70

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 71
<211> LENGTH: 177
<212> TYPE: PRT
<213> ORGANISM: Artificial Sequence
<220> FEATURE:
<223> OTHER INFORMATION: (P18, P20)beta chain

<400> SEQUENCE: 71

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

```
Ala Asp Cys Gly Phe Thr Ser Val Ser Tyr Gln Gln Gly Val Leu Ser
    130                 135                 140
Ala Thr Ile Leu Tyr Glu Ile Leu Leu Gly Lys Ala Thr Leu Tyr Ala
145                 150                 155                 160
Val Leu Val Ser Ala Leu Val Leu Met Ala Met Val Lys Arg Lys Asp
                165                 170                 175
Phe
```

<210> SEQ ID NO 72
<211> LENGTH: 613
<212> TYPE: PRT
<213> ORGANISM: Artificial Sequence
<220> FEATURE:
<223> OTHER INFORMATION: P1alpha (T185C)-P2A-P1beta

<400> SEQUENCE: 72

```
Met Leu Thr Ala Ser Leu Leu Arg Ala Val Ile Ala Ser Ile Cys Val
1               5                   10                  15
Val Ser Ser Met Ala Gln Lys Val Thr Gln Ala Gln Thr Glu Ile Ser
                20                  25                  30
Val Val Glu Lys Glu Asp Val Thr Leu Asp Cys Val Tyr Glu Thr Arg
            35                  40                  45
Asp Thr Thr Tyr Tyr Leu Phe Trp Tyr Lys Gln Pro Pro Ser Gly Glu
    50                  55                  60
Leu Val Phe Leu Ile Arg Arg Asn Ser Phe Asp Glu Gln Asn Glu Ile
65                  70                  75                  80
Ser Gly Arg Tyr Ser Trp Asn Phe Gln Lys Ser Thr Ser Ser Phe Asn
                85                  90                  95
Phe Thr Ile Thr Ala Ser Gln Val Val Asp Ser Ala Val Tyr Phe Cys
            100                 105                 110
Ala Leu Ser Glu Ala His Arg Asp Ser Asn Tyr Gln Leu Ile Trp Gly
    115                 120                 125
Ala Gly Thr Lys Leu Ile Ile Lys Pro Asp Ile Gln Asn Pro Asp Pro
130                 135                 140
Ala Val Tyr Gln Leu Arg Asp Ser Lys Ser Ser Asp Lys Ser Val Cys
145                 150                 155                 160
Leu Phe Thr Asp Phe Asp Ser Gln Thr Asn Val Ser Gln Ser Lys Asp
                165                 170                 175
Ser Asp Val Tyr Ile Thr Asp Lys Cys Val Leu Asp Met Arg Ser Met
            180                 185                 190
Asp Phe Lys Ser Asn Ser Ala Val Ala Trp Ser Asn Lys Ser Asp Phe
    195                 200                 205
Ala Cys Ala Asn Ala Phe Asn Asn Ser Ile Ile Pro Glu Asp Thr Phe
210                 215                 220
Phe Pro Ser Pro Glu Ser Ser Cys Asp Val Lys Leu Val Glu Lys Ser
225                 230                 235                 240
Phe Glu Thr Asp Thr Asn Leu Asn Phe Gln Asn Leu Ser Val Ile Gly
                245                 250                 255
Phe Arg Ile Leu Leu Leu Lys Val Ala Gly Phe Asn Leu Leu Met Thr
            260                 265                 270
Leu Arg Leu Trp Ser Ser Gly Ser Gly Ala Thr Asn Phe Ser Leu Leu
    275                 280                 285
Lys Gln Ala Gly Asp Val Glu Glu Asn Pro Gly Pro Met Gly Cys Arg
290                 295                 300
Leu Leu Cys Cys Ala Val Leu Cys Leu Leu Gly Ala Val Pro Met Glu
```

```
                305                 310                 315                 320
         Thr Gly Val Thr Gln Thr Pro Arg His Leu Val Met Gly Met Thr Asn
                         325                 330                 335

Lys Lys Ser Leu Lys Cys Glu Gln His Leu Gly His Asn Ala Met Tyr
                     340                 345                 350

Trp Tyr Lys Gln Ser Ala Lys Lys Pro Leu Glu Leu Met Phe Val Tyr
                     355                 360                 365

Asn Phe Lys Glu Gln Thr Glu Asn Asn Ser Val Pro Ser Arg Phe Ser
                 370                 375                 380

Pro Glu Cys Pro Asn Ser Ser His Leu Phe Leu His Leu His Thr Leu
         385                 390                 395                 400

Gln Pro Glu Asp Ser Ala Leu Tyr Leu Cys Ala Ser Ser Gln Asp Glu
                             405                 410                 415

Gln Phe Leu Tyr Asn Glu Gln Phe Phe Gly Pro Gly Thr Arg Leu Thr
                         420                 425                 430

Val Leu Glu Asp Leu Lys Asn Val Phe Pro Pro Glu Val Ala Val Phe
                     435                 440                 445

Glu Pro Ser Glu Ala Glu Ile Ser His Thr Gln Lys Ala Thr Leu Val
                 450                 455                 460

Cys Leu Ala Thr Gly Phe Tyr Pro Asp His Val Glu Leu Ser Trp Trp
         465                 470                 475                 480

Val Asn Gly Lys Glu Val His Ser Gly Val Cys Thr Asp Pro Gln Pro
                             485                 490                 495

Leu Lys Glu Gln Pro Ala Leu Asn Asp Ser Arg Tyr Cys Leu Ser Ser
                         500                 505                 510

Arg Leu Arg Val Ser Ala Thr Phe Trp Gln Asn Pro Arg Asn His Phe
                     515                 520                 525

Arg Cys Gln Val Gln Phe Tyr Gly Leu Ser Glu Asn Asp Glu Trp Thr
                 530                 535                 540

Gln Asp Arg Ala Lys Pro Val Thr Gln Ile Val Ser Ala Glu Ala Trp
         545                 550                 555                 560

Gly Arg Ala Asp Cys Gly Phe Thr Ser Glu Ser Tyr Gln Gln Gly Val
                             565                 570                 575

Leu Ser Ala Thr Ile Leu Tyr Glu Ile Leu Leu Gly Lys Ala Thr Leu
                         580                 585                 590

Tyr Ala Val Leu Val Ser Ala Leu Val Leu Met Ala Met Val Lys Arg
                     595                 600                 605

Lys Asp Ser Arg Gly
                 610

<210> SEQ ID NO 73
<211> LENGTH: 617
<212> TYPE: PRT
<213> ORGANISM: Artificial Sequence
<220> FEATURE:
<223> OTHER INFORMATION: P15alpha (T190C)-P2A-P15beta (S190C)

<400> SEQUENCE: 73

Met Asp Lys Ile Leu Gly Ala Ser Phe Leu Val Leu Trp Leu Gln Leu
1               5                   10                  15

Cys Trp Val Ser Gly Gln Gln Lys Glu Lys Ser Asp Gln Gln Gln Val
                20                  25                  30

Lys Gln Ser Pro Gln Ser Leu Ile Val Gln Lys Gly Gly Ile Ser Ile
            35                  40                  45

Ile Asn Cys Ala Tyr Glu Asn Thr Ala Phe Asp Tyr Phe Pro Trp Tyr
```

```
            50                  55                  60
Gln Gln Phe Pro Gly Lys Gly Pro Ala Leu Leu Ile Ala Ile Arg Pro
65                  70                  75                  80

Asp Val Ser Glu Lys Lys Glu Gly Arg Phe Thr Ile Ser Phe Asn Lys
                85                  90                  95

Ser Ala Lys Gln Phe Ser Leu His Ile Met Asp Ser Gln Pro Gly Asp
            100                 105                 110

Ser Ala Thr Tyr Phe Cys Ala Ala Ser Pro Gln Gly Ala Gly Ser Tyr
            115                 120                 125

Gln Leu Thr Phe Gly Lys Gly Thr Lys Leu Ser Val Ile Pro Asn Ile
            130                 135                 140

Gln Asn Pro Asp Pro Ala Val Tyr Gln Leu Arg Asp Ser Lys Ser Ser
145                 150                 155                 160

Asp Lys Ser Val Cys Leu Phe Thr Asp Phe Asp Ser Gln Thr Asn Val
                165                 170                 175

Ser Gln Ser Lys Asp Ser Asp Val Tyr Ile Thr Asp Lys Cys Val Leu
            180                 185                 190

Asp Met Arg Ser Met Asp Phe Lys Ser Asn Ser Ala Val Ala Trp Ser
            195                 200                 205

Asn Lys Ser Asp Phe Ala Cys Ala Asn Ala Phe Asn Asn Ser Ile Ile
            210                 215                 220

Pro Glu Asp Thr Phe Phe Pro Ser Pro Glu Ser Ser Cys Asp Val Lys
225                 230                 235                 240

Leu Val Glu Lys Ser Phe Glu Thr Asp Thr Asn Leu Asn Phe Gln Asn
                245                 250                 255

Leu Ser Val Ile Gly Phe Arg Ile Leu Leu Leu Lys Val Ala Gly Phe
            260                 265                 270

Asn Leu Leu Met Thr Leu Arg Leu Trp Ser Ser Gly Ser Gly Ala Thr
            275                 280                 285

Asn Phe Ser Leu Leu Lys Gln Ala Gly Asp Val Glu Glu Asn Pro Gly
            290                 295                 300

Pro Met Gly Thr Ser Leu Leu Cys Trp Met Ala Leu Cys Leu Leu Gly
305                 310                 315                 320

Ala Asp His Ala Asp Thr Gly Val Ser Gln Asp Pro Arg His Lys Ile
                325                 330                 335

Thr Lys Arg Gly Gln Asn Val Thr Phe Arg Cys Asp Pro Ile Ser Glu
            340                 345                 350

His Asn Arg Leu Tyr Trp Tyr Arg Gln Thr Leu Gly Gln Gly Pro Glu
            355                 360                 365

Phe Leu Thr Tyr Phe Gln Asn Glu Ala Gln Leu Glu Lys Ser Arg Leu
            370                 375                 380

Leu Ser Asp Arg Phe Ser Ala Glu Arg Pro Lys Gly Ser Phe Ser Thr
385                 390                 395                 400

Leu Glu Ile Gln Arg Thr Glu Gln Gly Asp Ser Ala Met Tyr Leu Cys
                405                 410                 415

Ala Ser Ser Leu Ala Tyr Gly Lys Asp Thr Gln Tyr Phe Gly Pro Gly
            420                 425                 430

Thr Arg Leu Thr Val Leu Glu Asp Leu Lys Asn Val Phe Pro Pro Glu
            435                 440                 445

Val Ala Val Phe Glu Pro Ser Glu Ala Glu Ile Ser His Thr Gln Lys
            450                 455                 460

Ala Thr Leu Val Cys Leu Ala Thr Gly Phe Tyr Pro Asp His Val Glu
465                 470                 475                 480
```

```
Leu Ser Trp Trp Val Asn Gly Lys Glu Val His Ser Gly Val Cys Thr
                485                 490                 495

Asp Pro Gln Pro Leu Lys Glu Gln Pro Ala Leu Asn Asp Ser Arg Tyr
            500                 505                 510

Cys Leu Ser Ser Arg Leu Arg Val Ser Ala Thr Phe Trp Gln Asn Pro
        515                 520                 525

Arg Asn His Phe Arg Cys Gln Val Gln Phe Tyr Gly Leu Ser Glu Asn
    530                 535                 540

Asp Glu Trp Thr Gln Asp Arg Ala Lys Pro Val Thr Gln Ile Val Ser
545                 550                 555                 560

Ala Glu Ala Trp Gly Arg Ala Asp Cys Gly Phe Thr Ser Glu Ser Tyr
                565                 570                 575

Gln Gln Gly Val Leu Ser Ala Thr Ile Leu Tyr Glu Ile Leu Leu Gly
            580                 585                 590

Lys Ala Thr Leu Tyr Ala Val Leu Val Ser Ala Leu Val Leu Met Ala
        595                 600                 605

Met Val Lys Arg Lys Asp Ser Arg Gly
    610                 615

<210> SEQ ID NO 74
<211> LENGTH: 607
<212> TYPE: PRT
<213> ORGANISM: Artificial Sequence
<220> FEATURE:
<223> OTHER INFORMATION: P18alpha (T184C)-P2A-P18beta (S188C)

<400> SEQUENCE: 74

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Ile Pro Thr Leu Met Asp Ser Asn Tyr Gln Leu Ile Trp Gly Ala
        115                 120                 125

Gly Thr Lys Leu Ile Ile Lys Pro Asp Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220
```

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
            245                 250                 255

Arg Ile Leu Leu Leu Lys Val Ala Gly Phe Asn Leu Leu Met Thr Leu
                260                 265                 270

Arg Leu Trp Ser Ser Gly Ser Gly Ala Thr Asn Phe Ser Leu Leu Lys
            275                 280                 285

Gln Ala Gly Asp Val Glu Glu Asn Pro Gly Pro Met Gly Ser Trp Thr
290                 295                 300

Leu Cys Cys Val Ser Leu Cys Ile Leu Val Ala Lys His Thr Asp Ala
305                 310                 315                 320

Gly Val Ile Gln Ser Pro Arg His Glu Val Thr Glu Met Gly Gln Glu
                325                 330                 335

Val Thr Leu Arg Cys Lys Pro Ile Ser Gly His Asp Tyr Leu Phe Trp
                340                 345                 350

Tyr Arg Gln Thr Met Met Arg Gly Leu Glu Leu Leu Ile Tyr Phe Asn
            355                 360                 365

Asn Asn Val Pro Ile Asp Asp Ser Gly Met Pro Glu Asp Arg Phe Ser
370                 375                 380

Ala Lys Met Pro Asn Ala Ser Phe Ser Thr Leu Lys Ile Gln Pro Ser
385                 390                 395                 400

Glu Pro Arg Asp Ser Ala Val Tyr Phe Cys Ala Ser Ser Val Ser Gly
                405                 410                 415

Ser Glu Ala Phe Phe Gly Gln Gly Thr Arg Leu Thr Val Val Glu Asp
            420                 425                 430

Leu Asn Lys Val Phe Pro Pro Glu Val Ala Val Phe Glu Pro Ser Glu
            435                 440                 445

Ala Glu Ile Ser His Thr Gln Lys Ala Thr Leu Val Cys Leu Ala Thr
450                 455                 460

Gly Phe Phe Pro Asp His Val Glu Leu Ser Trp Trp Val Asn Gly Lys
465                 470                 475                 480

Glu Val His Ser Gly Val Cys Thr Asp Pro Gln Pro Leu Lys Glu Gln
                485                 490                 495

Pro Ala Leu Asn Asp Ser Arg Tyr Cys Leu Ser Ser Arg Leu Arg Val
            500                 505                 510

Ser Ala Thr Phe Trp Gln Asn Pro Arg Asn His Phe Arg Cys Gln Val
            515                 520                 525

Gln Phe Tyr Gly Leu Ser Glu Asn Asp Glu Trp Thr Gln Asp Arg Ala
530                 535                 540

Lys Pro Val Thr Gln Ile Val Ser Ala Glu Ala Trp Gly Arg Ala Asp
545                 550                 555                 560

Cys Gly Phe Thr Ser Val Ser Tyr Gln Gln Gly Val Leu Ser Ala Thr
                565                 570                 575

Ile Leu Tyr Glu Ile Leu Leu Gly Lys Ala Thr Leu Tyr Ala Val Leu
            580                 585                 590

Val Ser Ala Leu Val Leu Met Ala Met Val Lys Arg Lys Asp Phe
595                 600                 605

<210> SEQ ID NO 75
<211> LENGTH: 599
<212> TYPE: PRT
<213> ORGANISM: Artificial Sequence
<220> FEATURE:

<223> OTHER INFORMATION: P20alpha (T179C)-P2A-P20beta (S185C)

<400> SEQUENCE: 75

```
Met Met Lys Ser Leu Arg Val Leu Leu Val Ile Leu Trp Leu Gln Leu
1               5                   10                  15
Ser Trp Val Trp Ser Gln Gln Lys Glu Val Glu Gln Asn Ser Gly Pro
            20                  25                  30
Leu Ser Val Pro Glu Gly Ala Ile Ala Ser Leu Asn Cys Thr Tyr Ser
        35                  40                  45
Asp Arg Gly Ser Gln Ser Phe Phe Trp Tyr Arg Gln Tyr Ser Gly Lys
    50                  55                  60
Ser Pro Glu Leu Ile Met Ser Ile Tyr Ser Asn Gly Asp Lys Glu Asp
65                  70                  75                  80
Gly Arg Phe Thr Ala Gln Leu Asn Lys Ala Ser Gln Tyr Val Ser Leu
                85                  90                  95
Leu Ile Arg Asp Ser Gln Pro Ser Asp Ser Ala Thr Tyr Leu Cys Ala
            100                 105                 110
Val Leu Glu Gly Gln Lys Leu Leu Phe Ala Arg Gly Thr Met Leu Lys
        115                 120                 125
Val Asp Leu Asn Ile Gln Asn Pro Asp Pro Ala Val Tyr Gln Leu Arg
    130                 135                 140
Asp Ser Lys Ser Ser Asp Lys Ser Val Cys Leu Phe Thr Asp Phe Asp
145                 150                 155                 160
Ser Gln Thr Asn Val Ser Gln Ser Lys Asp Ser Asp Val Tyr Ile Thr
                165                 170                 175
Asp Lys Cys Val Leu Asp Met Arg Ser Met Asp Phe Lys Ser Asn Ser
            180                 185                 190
Ala Val Ala Trp Ser Asn Lys Ser Asp Phe Ala Cys Ala Asn Ala Phe
        195                 200                 205
Asn Asn Ser Ile Ile Pro Glu Asp Thr Phe Phe Pro Ser Pro Glu Ser
    210                 215                 220
Ser Cys Asp Val Lys Leu Val Glu Lys Ser Phe Glu Thr Asp Thr Asn
225                 230                 235                 240
Leu Asn Phe Gln Asn Leu Ser Val Ile Gly Phe Arg Ile Leu Leu Leu
                245                 250                 255
Lys Val Ala Gly Phe Asn Leu Leu Met Thr Leu Arg Leu Trp Ser Ser
            260                 265                 270
Gly Ser Gly Ala Thr Asn Phe Ser Leu Leu Lys Gln Ala Gly Asp Val
        275                 280                 285
Glu Glu Asn Pro Gly Pro Met Gly Ile Arg Leu Leu Cys Arg Val Ala
    290                 295                 300
Phe Cys Phe Leu Ala Val Gly Leu Val Asp Val Lys Val Thr Gln Ser
305                 310                 315                 320
Ser Arg Tyr Leu Val Lys Arg Thr Gly Glu Lys Val Phe Leu Glu Cys
                325                 330                 335
Val Gln Asp Met Asp His Glu Asn Met Phe Trp Tyr Arg Gln Asp Pro
            340                 345                 350
Gly Leu Gly Leu Arg Leu Ile Tyr Phe Ser Tyr Asp Val Lys Met Lys
        355                 360                 365
Glu Lys Gly Asp Ile Pro Glu Gly Tyr Ser Val Ser Arg Glu Lys Lys
    370                 375                 380
Glu Arg Phe Ser Leu Ile Leu Glu Ser Ala Ser Thr Asn Gln Thr Ser
385                 390                 395                 400
```

Met Tyr Leu Cys Ala Thr Ser His Gln Pro Gln His Phe Gly Asp Gly
              405                 410                 415

Thr Arg Leu Ser Ile Leu Glu Asp Leu Asn Lys Val Phe Pro Pro Glu
        420                 425                 430

Val Ala Val Phe Glu Pro Ser Glu Ala Glu Ile Ser His Thr Gln Lys
            435                 440                 445

Ala Thr Leu Val Cys Leu Ala Thr Gly Phe Phe Pro Asp His Val Glu
    450                 455                 460

Leu Ser Trp Trp Val Asn Gly Lys Glu Val His Ser Gly Val Cys Thr
465                 470                 475                 480

Asp Pro Gln Pro Leu Lys Glu Gln Pro Ala Leu Asn Asp Ser Arg Tyr
                485                 490                 495

Cys Leu Ser Ser Arg Leu Arg Val Ser Ala Thr Phe Trp Gln Asn Pro
                500                 505                 510

Arg Asn His Phe Arg Cys Gln Val Gln Phe Tyr Gly Leu Ser Glu Asn
                515                 520                 525

Asp Glu Trp Thr Gln Asp Arg Ala Lys Pro Val Thr Gln Ile Val Ser
            530                 535                 540

Ala Glu Ala Trp Gly Arg Ala Asp Cys Gly Phe Thr Ser Val Ser Tyr
545                 550                 555                 560

Gln Gln Gly Val Leu Ser Ala Thr Ile Leu Tyr Glu Ile Leu Leu Gly
                565                 570                 575

Lys Ala Thr Leu Tyr Ala Val Leu Val Ser Ala Leu Val Leu Met Ala
                580                 585                 590

Met Val Lys Arg Lys Asp Phe
            595

<210> SEQ ID NO 76
<211> LENGTH: 603
<212> TYPE: PRT
<213> ORGANISM: Artificial Sequence
<220> FEATURE:
<223> OTHER INFORMATION: P22alpha (T180C)-P2A-P22beta (S186C)

<400> SEQUENCE: 76

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Val Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Ala Asn Asn Ala Gly Asn Met Leu Thr Phe Gly Gly Gly Thr Arg Leu
        115                 120                 125

Met Val Lys Pro His Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

-continued

Asp Ser Gln Thr Asn Val Ser Gln Ser Lys Asp Ser Asp Val Tyr Ile
                165                 170                 175
Thr Asp Lys Cys Val Leu Asp Met Arg Ser Met Asp Phe Lys Ser Asn
            180                 185                 190
Ser Ala Val Ala Trp Ser Asn Lys Ser Asp Phe Ala Cys Ala Asn Ala
        195                 200                 205
Phe Asn Asn Ser Ile Ile Pro Glu Asp Thr Phe Phe Pro Ser Pro Glu
    210                 215                 220
Ser Ser Cys Asp Val Lys Leu Val Glu Lys Ser Phe Glu Thr Asp Thr
225                 230                 235                 240
Asn Leu Asn Phe Gln Asn Leu Ser Val Ile Gly Phe Arg Ile Leu Leu
                245                 250                 255
Leu Lys Val Ala Gly Phe Asn Leu Leu Met Thr Leu Arg Leu Trp Ser
            260                 265                 270
Ser Gly Ser Gly Ala Thr Asn Phe Ser Leu Leu Lys Gln Ala Gly Asp
        275                 280                 285
Val Glu Glu Asn Pro Gly Pro Met Gly Ile Arg Leu Leu Cys Arg Val
    290                 295                 300
Ala Phe Cys Phe Leu Ala Val Gly Leu Val Asp Val Lys Val Thr Gln
305                 310                 315                 320
Ser Ser Arg Tyr Leu Val Lys Arg Thr Gly Glu Lys Val Phe Leu Glu
                325                 330                 335
Cys Val Gln Asp Met Asp His Glu Asn Met Phe Trp Tyr Arg Gln Asp
            340                 345                 350
Pro Gly Leu Gly Leu Arg Leu Ile Tyr Phe Ser Tyr Asp Val Lys Met
        355                 360                 365
Lys Glu Lys Gly Asp Ile Pro Glu Gly Tyr Ser Val Ser Arg Glu Lys
    370                 375                 380
Lys Glu Arg Phe Ser Leu Ile Leu Glu Ser Ala Ser Thr Asn Gln Thr
385                 390                 395                 400
Ser Met Tyr Leu Cys Ala Ser Ser Ile Asn Glu Gln Phe Phe Gly
                405                 410                 415
Pro Gly Thr Arg Leu Thr Val Leu Glu Asp Leu Lys Asn Val Phe Pro
            420                 425                 430
Pro Glu Val Ala Val Phe Glu Pro Ser Glu Ala Glu Ile Ser His Thr
        435                 440                 445
Gln Lys Ala Thr Leu Val Cys Leu Ala Thr Gly Phe Tyr Pro Asp His
    450                 455                 460
Val Glu Leu Ser Trp Trp Val Asn Gly Lys Glu Val His Ser Gly Val
465                 470                 475                 480
Cys Thr Asp Pro Gln Pro Leu Lys Glu Gln Pro Ala Leu Asn Asp Ser
                485                 490                 495
Arg Tyr Cys Leu Ser Ser Arg Leu Arg Val Ser Ala Thr Phe Trp Gln
            500                 505                 510
Asn Pro Arg Asn His Phe Arg Cys Gln Val Gln Phe Tyr Gly Leu Ser
        515                 520                 525
Glu Asn Asp Glu Trp Thr Gln Asp Arg Ala Lys Pro Val Thr Gln Ile
    530                 535                 540
Val Ser Ala Glu Ala Trp Gly Arg Ala Asp Cys Gly Phe Thr Ser Glu
545                 550                 555                 560
Ser Tyr Gln Gln Gly Val Leu Ser Ala Thr Ile Leu Tyr Glu Ile Leu
                565                 570                 575
Leu Gly Lys Ala Thr Leu Tyr Ala Val Leu Val Ser Ala Leu Val Leu

```
                580            585            590
Met Ala Met Val Lys Arg Lys Asp Ser Arg Gly
        595            600
```

<210> SEQ ID NO 77
<211> LENGTH: 387
<212> TYPE: DNA
<213> ORGANISM: Artificial Sequence
<220> FEATURE:
<223> OTHER INFORMATION: C4alpha chain variable domain WT

<400> SEQUENCE: 77

```
atgacatcca ttcgagctgt atttatattc ctgtggctgc agctggactt ggtgaatgga    60
gagaatgtgg agcagcatcc ttcaaccctg agtgtccagg agggagacag cgctgttatc   120
aagtgtactt attcagacag tgcctcaaac tacttccctt ggtataagca agaacttgga   180
aaaagacctc agcttattat agacattcgt tcaaatgtgg gcgaaaagaa agaccaacga   240
attgctgtta cattgaacaa gacagccaaa catttctccc tgcacatcac agagacccaa   300
cctgaagact cggctgtcta cttctgtgca gcgaccgaag actatcagtt aatctggggc   360
gctgggacca agctaattat aaagcca                                      387
```

<210> SEQ ID NO 78
<211> LENGTH: 387
<212> TYPE: DNA
<213> ORGANISM: Artificial Sequence
<220> FEATURE:
<223> OTHER INFORMATION: C4 alpha chain variable domain - Codon
      Optimized

<400> SEQUENCE: 78

```
atgaccagca tccgggccgt gttcatcttc ctgtggctgc agctggacct cgtcaacggc    60
gagaacgtgg aacagcaccc cagcaccctg agcgtgcagg aaggcgacag cgccgtcatc   120
aagtgcacct acagcgactc cgccagcaac tacttcccct ggtacaagca ggaactgggc   180
aagcggcccc agctgatcat cgacatccgg tccaacgtgg gcgagaagaa ggaccagcgg   240
atcgccgtga ccctgaacaa gaccgccaag cacttcagcc tgcacatcac cgagacacag   300
cccgaggact ccgccgtgta cttctgtgcc gccaccgagg attaccagct gatctgggga   360
gccggcacca agctgatcat taagccc                                      387
```

<210> SEQ ID NO 79
<211> LENGTH: 387
<212> TYPE: DNA
<213> ORGANISM: Artificial Sequence
<220> FEATURE:
<223> OTHER INFORMATION: C4alpha-DLT chain variable domain

<400> SEQUENCE: 79

```
atgacatcca ttcgagctgt atttatattc ctgtggctgc agctggactt ggtgaatgga    60
gagaatgtgg agcagcatcc ttcaaccctg agtgtccagg agggagacag cgctgttatc   120
aagtgtactt attcagacag tgcctcaaac tacttccctt ggtataagca agaacttgga   180
aaaagacctc agcttattat agacattcgt tcaaatgtgg gcgaaaagaa agaccaacga   240
attgctgtta cattgaacaa gacagccaaa catttctccc tgcacatcac agagacccaa   300
cctgaagact cggctgtcta cttctgtgca gcgaccgaag acctgacgtt aatctggggc   360
gctgggacca agctaattat aaagcca                                      387
```

<210> SEQ ID NO 80
<211> LENGTH: 387
<212> TYPE: DNA
<213> ORGANISM: Artificial Sequence
<220> FEATURE:
<223> OTHER INFORMATION: C4alpha-DLT chain variable domain, Codon Optimized

<400> SEQUENCE: 80

```
atgaccagca tccgggccgt gttcatcttc ctgtggctgc agctggacct cgtcaacggc    60
gagaacgtgg aacagcaccc cagcaccctg agcgtgcagg aaggcgacag cgccgtcatc   120
aagtgcacct acagcgactc cgccagcaac tacttcccct ggtacaagca ggaactgggc   180
aagcggcccc agctgatcat cgacatccgg tccaacgtgg cgagaagaa ggaccagcgg   240
atcgccgtga ccctgaacaa gaccgccaag cacttcagcc tgcacatcac cgagacacag   300
cccgaggact ccgccgtgta cttctgtgcc gccaccgagg atctgacgct gatctgggga   360
gccggcacca agctgatcat taagccc                                       387
```

<210> SEQ ID NO 81
<211> LENGTH: 426
<212> TYPE: DNA
<213> ORGANISM: Artificial Sequence
<220> FEATURE:
<223> OTHER INFORMATION: C4alpha chain constant domain WT

<400> SEQUENCE: 81

```
gatatccaga accctgaccc tgccgtgtac agctgagag actctaaatc cagtgacaag    60
tctgtctgcc tattcaccga ttttgattct caaacaaatg tgtcacaaag taaggattct   120
gatgtgtata tcacagacaa aactgtgcta gacatgaggt ctatggactt caagagcaac   180
agtgctgtgg cctggagcaa caaatctgac tttgcatgtg caaacgcctt caacaacagc   240
attattccag aagacacctt cttccccagc ccagaaagtt cctgtgatgt caagctggtc   300
gagaaaagct ttgaaacaga tacgaaccta aactttcaaa acctgtcagt gattgggttc   360
cgaatcctcc tcctgaaagt ggccgggttt aatctgctca tgacgctgcg gctgtggtcc   420
agctga                                                               426
```

<210> SEQ ID NO 82
<211> LENGTH: 426
<212> TYPE: DNA
<213> ORGANISM: Artificial Sequence
<220> FEATURE:
<223> OTHER INFORMATION: C4alpha chain constant domain - Codon-Optimized

<400> SEQUENCE: 82

```
gacatccaga accccgaccc tgccgtgtac agctgcggg acagcaagag cagcgacaag    60
agcgtgtgcc tgttcaccga cttcgacagc cagaccaacg tgtcccagag caaggacagc   120
gacgtgtaca tcaccgataa gaccgtgctg gacatgcgga gcatggactt caagagcaac   180
agcgccgtgg cctggtccaa caagagcgac ttcgcctgcg ccaacgcctt caacaacagc   240
attatccccg aggacacatt cttcccaagc ccgagagca gctgcgacgt gaagctggtg   300
gaaaagagct cgagacaga caccaacctg aacttccaga acctcagcgt gatcggcttc   360
cggatcctgc tgctgaaggt ggccggcttc aacctgctga tgaccctgcg gctgtggtcc   420
agctga                                                               426
```

<210> SEQ ID NO 83
<211> LENGTH: 426

<210> SEQ ID NO 83
<211> LENGTH: 426
<212> TYPE: DNA
<213> ORGANISM: Artificial Sequence
<220> FEATURE:
<223> OTHER INFORMATION: C4alpha chain constant domain - Cys
    Modification

<400> SEQUENCE: 83

| | |
|---|---|
| gatatccaga accctgaccc tgccgtgtac cagctgagag actctaaatc cagtgacaag | 60 |
| tctgtctgcc tattcaccga ttttgattct caaacaaatg tgtcacaaag taaggattct | 120 |
| gatgtgtata tcacagacaa atgcgtgcta gacatgaggt ctatggactt caagagcaac | 180 |
| agtgctgtgg cctggagcaa caaatctgac tttgcatgtg caaacgcctt caacaacagc | 240 |
| attattccag aagacacctt cttccccagc ccagaaagtt cctgtgatgt caagctggtc | 300 |
| gagaaaagct tgaaacaga tacgaaccta aactttcaaa acctgtcagt gattgggttc | 360 |
| cgaatcctcc tcctgaaagt ggccgggttt aatctgctca tgacgctgcg gctgtggtcc | 420 |
| agctga | 426 |

<210> SEQ ID NO 84
<211> LENGTH: 426
<212> TYPE: DNA
<213> ORGANISM: Artificial Sequence
<220> FEATURE:
<223> OTHER INFORMATION: C4alpha chain constant domain - Cys
    Modification, Codon-Optimized

<400> SEQUENCE: 84

| | |
|---|---|
| gacatccaga accccgaccc tgccgtgtac cagctgcggg acagcaagag cagcgacaag | 60 |
| agcgtgtgcc tgttcaccga cttcgacagc cagaccaacg tgcccagag caaggacagc | 120 |
| gacgtgtaca tcaccgataa gtgcgtgctg gacatgcgga gcatggactt caagagcaac | 180 |
| agcgccgtgg cctggtccaa caagagcgac ttcgcctgcg ccaacgcctt caacaacagc | 240 |
| attatccccg aggacacatt cttcccaagc cccgagagca gcgcgacgt gaagctggtg | 300 |
| gaaaagagct tcgagacaga caccaacctg aacttccaga acctcagcgt gatcggcttc | 360 |
| cggatcctgc tgctgaaggt ggccggcttc aacctgctga tgaccctgcg gctgtggtcc | 420 |
| agctga | 426 |

<210> SEQ ID NO 85
<211> LENGTH: 813
<212> TYPE: DNA
<213> ORGANISM: Artificial Sequence
<220> FEATURE:
<223> OTHER INFORMATION: C4alpha chain WT

<400> SEQUENCE: 85

| | |
|---|---|
| atgacatcca ttcgagctgt atttatattc ctgtggctgc agctggactt ggtgaatgga | 60 |
| gagaatgtgg agcagcatcc ttcaaccctg agtgtccagg agggagacag cgctgttatc | 120 |
| aagtgtactt attcagacag tgcctcaaac tacttcccct ggtataagca agaacttgga | 180 |
| aaaagacctc agcttattat agacattcgt tcaaatgtgg gcgaaaagaa agaccaacga | 240 |
| attgctgtta cattgaacaa gacagccaaa catttctccc tgcacatcac agagacccaa | 300 |
| cctgaagact cggctgtcta cttctgtgca gcgaccgaag actatcagtt aatctggggc | 360 |
| gctgggacca agctaattat aaagccagat atccagaacc ctgaccctgc cgtgtaccag | 420 |
| ctgagagact ctaaatccag tgacaagtct gtctgcctat tcaccgattt tgattctcaa | 480 |
| acaaatgtgt cacaaagtaa ggattctgat gtgtatatca cagacaaaac tgtgctagac | 540 |

| | |
|---|---|
| atgaggtcta tggacttcaa gagcaacagt gctgtggcct ggagcaacaa atctgacttt | 600 |
| gcatgtgcaa acgccttcaa caacagcatt attccagaag acaccttctt ccccagccca | 660 |
| gaaagttcct gtgatgtcaa gctggtcgag aaaagctttg aaacagatac gaacctaaac | 720 |
| tttcaaaacc tgtcagtgat tgggttccga atcctcctcc tgaaagtggc cgggtttaat | 780 |
| ctgctcatga cgctgcggct gtggtccagc tga | 813 |

<210> SEQ ID NO 86
<211> LENGTH: 813
<212> TYPE: DNA
<213> ORGANISM: Artificial Sequence
<220> FEATURE:
<223> OTHER INFORMATION: C4alpha chain - Cys Modification, Codon-
      Optimized

<400> SEQUENCE: 86

| | |
|---|---|
| atgaccagca tccgggccgt gttcatcttc ctgtggctgc agctggacct cgtcaacggc | 60 |
| gagaacgtgg aacagcaccc cagcaccctg agcgtgcagg aaggcgacag cgccgtcatc | 120 |
| aagtgcacct acagcgactc cgccagcaac tacttcccct ggtacaagca ggaactgggc | 180 |
| aagcggcccc agctgatcat cgacatccgg tccaacgtgg cgagaagaa ggaccagcgg | 240 |
| atcgccgtga ccctgaacaa gaccgccaag cacttcagcc tgcacatcac cgagacacag | 300 |
| cccgaggact ccgccgtgta cttctgtgcc gccaccgagg actaccagct gatctgggga | 360 |
| gccggcacca agctgatcat taagcccgac atccagaacc ccgaccctgc cgtgtaccag | 420 |
| ctgcgggaca gcaagagcag cgacaagagc gtgtgcctgt tcaccgactt cgacagccag | 480 |
| accaacgtgt cccagagcaa ggacagcgac gtgtacatca ccgataagtg cgtgctggac | 540 |
| atgcggagca tggacttcaa gagcaacagc gccgtggcct ggtccaacaa gagcgacttc | 600 |
| gcctgcgcca acgccttcaa caacagcatt atccccgagg acacattctt cccaagcccc | 660 |
| gagagcagct gcgacgtgaa gctggtggaa aagagcttcg agacagacac caacctgaac | 720 |
| ttccagaacc tcagcgtgat cggcttccgg atcctgctgc tgaaggtggc cggcttcaac | 780 |
| ctgctgatga ccctgcggct gtggtccagc tga | 813 |

<210> SEQ ID NO 87
<211> LENGTH: 813
<212> TYPE: DNA
<213> ORGANISM: Artificial Sequence
<220> FEATURE:
<223> OTHER INFORMATION: C4alpha-DLT chain - Cys modification, Codon
      Optimized

<400> SEQUENCE: 87

| | |
|---|---|
| atgaccagca tccgggccgt gttcatcttc ctgtggctgc agctggacct cgtcaacggc | 60 |
| gagaacgtgg aacagcaccc cagcaccctg agcgtgcagg aaggcgacag cgccgtcatc | 120 |
| aagtgcacct acagcgactc cgccagcaac tacttcccct ggtacaagca ggaactgggc | 180 |
| aagcggcccc agctgatcat cgacatccgg tccaacgtgg cgagaagaa ggaccagcgg | 240 |
| atcgccgtga ccctgaacaa gaccgccaag cacttcagcc tgcacatcac cgagacacag | 300 |
| cccgaggact ccgccgtgta cttctgtgcc gccaccgagg atctgacgct gatctgggga | 360 |
| gccggcacca agctgatcat taagcccgac atccagaacc ccgaccctgc cgtgtaccag | 420 |
| ctgcgggaca gcaagagcag cgacaagagc gtgtgcctgt tcaccgactt cgacagccag | 480 |
| accaacgtgt cccagagcaa ggacagcgac gtgtacatca ccgataagtg cgtgctggac | 540 |
| atgcggagca tggacttcaa gagcaacagc gccgtggcct ggtccaacaa gagcgacttc | 600 |

```
gcctgcgcca acgccttcaa caacagcatt atccccgagg acacattctt cccaagcccc    660
gagagcagct gcgacgtgaa gctggtggaa aagagcttcg agacagacac caacctgaac    720
ttccagaacc tcagcgtgat cggcttccgg atcctgctgc tgaaggtggc cggcttcaac    780
ctgctgatga ccctgcggct gtggtccagc tga                                  813

<210> SEQ ID NO 88
<211> LENGTH: 393
<212> TYPE: DNA
<213> ORGANISM: Artificial Sequence
<220> FEATURE:
<223> OTHER INFORMATION: C4beta chain variable domain WT

<400> SEQUENCE: 88
atgagcaacc aggtgctctg ctgtgtggtc ctttgtttcc tgggagcaaa caccgtggat     60
ggtggaatca ctcagtcccc aaagtacctg ttcagaaagg aaggacagaa tgtgaccctg    120
agttgtgaac agaatttgaa ccacgatgcc atgtactggt accgacagga cccagggcaa    180
gggctgagat tgatctacta ctcacagata gtaaatgact tcagaaaggg agatatagct    240
gaagggtaca gcgtctctcg ggagaagaag aatccttttc ctctcactgt gacatcggcc    300
caaaagaacc cgacagcttt ctatctctgt gccagtagcc ccggggccct ctacgagcag    360
tacttcgggc cgggcaccag gctcacggtc aca                                  393

<210> SEQ ID NO 89
<211> LENGTH: 393
<212> TYPE: DNA
<213> ORGANISM: Artificial Sequence
<220> FEATURE:
<223> OTHER INFORMATION: C4beta chain variable domain -Codon Optimized

<400> SEQUENCE: 89
atgagcaacc aggtgctgtg ctgcgtggtg ctgtgtttcc tgggcgccaa caccgtggac     60
ggcggcatca cccagagccc caagtacctg ttccggaaag agggccagaa cgtcaccctg    120
agctgcgagc agaacctgaa ccacgacgcc atgtactggt acagacagga ccccggacag    180
ggcctgcggc tgatctacta cagccagatc gtgaacgact ccagaagggg agatatcgcc    240
gagggctaca gcgtgtccag agagaagaaa gagtccttcc cactgaccgt gaccagcgcc    300
cagaagaacc ccaccgcctt ctacctgtgc gccagctctc ctggcgccct gtacgagcag    360
tacttcggcc ctggcacccg gctgacagtg acc                                  393

<210> SEQ ID NO 90
<211> LENGTH: 540
<212> TYPE: DNA
<213> ORGANISM: Artificial Sequence
<220> FEATURE:
<223> OTHER INFORMATION: (C4, P1, P15, P22)beta chain constant domain WT

<400> SEQUENCE: 90
gaggacctga aaacgtgttt cccacccgag gtcgctgtgt ttgagccatc agaagcagag     60
atctcccaca cccaaaaggc cacactggtg tgcctggcca caggcttcta ccccgaccac    120
gtggagctga gctggtgggt gaatgggaag gaggtgcaca gtgggtcag cacagacccg    180 cagcccctca aggagcagcc cgccctcaat gactccagat actgcctgag cagccgcctg    240
agggtctcgg ccaccttctg gcagaacccc cgcaaccact ccgctgtca agtccagttc    300 tacgggctct cggagaatga cgagtggacc caggataggg ccaaacctgt cacccagatc    360
```

| | |
|---|---|
| gtcagcgccg aggcctgggg tagagcagac tgtggcttca cctccgagtc ttaccagcaa | 420 |
| ggggtcctgt ctgccaccat cctctatgag atcttgctag gaaggccac cttgtatgcc | 480 |
| gtgctggtca gtgccctcgt gctgatggcc atggtcaaga gaaaggattc cagaggctag | 540 |

<210> SEQ ID NO 91
<211> LENGTH: 540
<212> TYPE: DNA
<213> ORGANISM: Artificial Sequence
<220> FEATURE:
<223> OTHER INFORMATION: (C4, P1, P15, P22)beta chain constant domain - Cys modification

<400> SEQUENCE: 91

| | |
|---|---|
| gaggacctga aaacgtgtt cccacccgag gtcgctgtgt ttgagccatc agaagcagag | 60 |
| atctcccaca cccaaaaggc cacactggtg tgcctggcca caggcttcta ccccgaccac | 120 |
| gtggagctga gctggtgggt gaatgggaag gaggtgcaca gtggggtcag cacagacccg | 180 |
| cagcccctca aggagcagcc cgccctcaat gactccagat actgcctgag cagccgcctg | 240 |
| agggtctcgg ccaccttctg gcagaacccc gcaaccact tccgctgtca agtccagttc | 300 |
| tacgggctct cggagaatga cgagtggacc caggataggg ccaaacctgt cacccagatc | 360 |
| gtcagcgccg aggcctgggg tagagcagac tgtggcttca cctccgagtc ttaccagcaa | 420 |
| ggggtcctgt ctgccaccat cctctatgag atcttgctag gaaggccac cttgtatgcc | 480 |
| gtgctggtca gtgccctcgt gctgatggcc atggtcaaga gaaaggattc cagaggctag | 540 |

<210> SEQ ID NO 92
<211> LENGTH: 540
<212> TYPE: DNA
<213> ORGANISM: Artificial Sequence
<220> FEATURE:
<223> OTHER INFORMATION: (C4, P1, P15, P22)beta chain constant domain - Codon Optimized

<400> SEQUENCE: 92

| | |
|---|---|
| gaggacctga agaacgtgtt ccccccagag gtggccgtgt tcgagcctag cgaggccgag | 60 |
| atcagccaca cccagaaagc caccctcgtg tgcctggcca ccggcttta ccccgaccac | 120 |
| gtggaactgt cttggtgggt caacggcaaa gaggtgcaca gcggcgtcag caccgacccc | 180 |
| cagcccctga agagcagcc cgccctgaac gacagccggt actgtctgag cagcagactg | 240 |
| agagtgtccg ccaccttctg gcagaacccc cggaaccact tcagatgcca ggtgcagttc | 300 |
| tacggcctga gcgagaacga cgagtggacc caggaccggg ccaagcccgt gacccagatc | 360 |
| gtgtctgctg aggcctgggg cagagccgat tgcggcttca ccagcgagag ctaccagcag | 420 |
| ggcgtgctga gcgccaccat cctgtacgag atcctgctgg gcaaggccac cctgtacgcc | 480 |
| gtgctggtgt ccgccctggt gctgatggcc atggtcaagc ggaaggacag ccggggctga | 540 |

<210> SEQ ID NO 93
<211> LENGTH: 540
<212> TYPE: DNA
<213> ORGANISM: Artificial Sequence
<220> FEATURE:
<223> OTHER INFORMATION: (C4, P1, P15, P22)beta chain constant domain - Cys modification, Codon Optimized

<400> SEQUENCE: 93

| | |
|---|---|
| gaggacctga agaacgtgtt ccccccagag gtggccgtgt tcgagcctag cgaggccgag | 60 |
| atcagccaca cccagaaagc caccctcgtg tgcctggcca ccggcttta ccccgaccac | 120 |

| | |
|---|---|
| gtggaactgt cttggtgggt caacggcaaa gaggtgcaca gcggcgtctg caccgacccc | 180 |
| cagcccctga aagagcagcc cgccctgaac gacagccggt actgtctgag cagcagactg | 240 |
| agagtgtccg ccaccttctg cagaaccccc cggaaccact tcagatgcca ggtgcagttc | 300 |
| tacggcctga gcgagaacga cgagtggacc caggaccggg ccaagcccgt gacccagatc | 360 |
| gtgtctgctg aggcctgggg cagagccgat tgcggcttca ccagcgagag ctaccagcag | 420 |
| ggcgtgctga cgccaccat cctgtacgag atcctgctgg caaggccac cctgtacgcc | 480 |
| gtgctggtgt ccgccctggt gctgatggcc atggtcaagc ggaaggacag ccggggctga | 540 |

<210> SEQ ID NO 94
<211> LENGTH: 933
<212> TYPE: DNA
<213> ORGANISM: Artificial Sequence
<220> FEATURE:
<223> OTHER INFORMATION: C4beta chain WT

<400> SEQUENCE: 94

| | |
|---|---|
| atgagcaacc aggtgctctg ctgtgtggtc ctttgtttcc tgggagcaaa caccgtggat | 60 |
| ggtggaatca ctcagtcccc aaagtacctg ttcagaaagg aaggacagaa tgtgaccctg | 120 |
| agttgtgaac agaatttgaa ccacgatgcc atgtactggt accgacagga cccagggcaa | 180 |
| gggctgagat tgatctacta ctcacagata gtaaatgact ttcagaaagg agatatagct | 240 |
| gaagggtaca gcgtctctcg ggagaagaag gaatcctttc ctctcactgt gacatcggcc | 300 |
| caaaagaacc cgacagcttt ctatctctgt gccagtagcc ccggggccct ctacgagcag | 360 |
| tacttcgggc cgggcaccag gctcacggtc acagaggacc tgaaaaacgt gttcccaccc | 420 |
| gaggtcgctg tgtttgagcc atcagaagca gagatctccc acacccaaaa ggccacactg | 480 |
| gtgtgcctgg ccacaggctt ctaccccgac cacgtggagc tgagctggtg ggtgaatggg | 540 |
| aaggaggtgc acagtggggt cagcacagac ccgcagcccc tcaaggagca gcccgccctc | 600 |
| aatgactcca gatactgcct gagcagccgc ctgagggtct cggccacctt ctggcagaac | 660 |
| ccccgcaacc acttccgctg tcaagtccag ttctacgggc tctcggagaa tgacgagtgg | 720 |
| acccaggata gggccaaacc tgtcacccag atcgtcagcg ccgaggcctg ggtagagca | 780 |
| gactgtggct tcacctccga gtcttaccag caaggggtcc tgtctgccac catcctctat | 840 |
| gagatcttgc tagggaaggc caccttgtat gccgtgctgg tcagtgccct cgtgctgatg | 900 |
| gccatggtca agagaaagga ttccagaggc tag | 933 |

<210> SEQ ID NO 95
<211> LENGTH: 933
<212> TYPE: DNA
<213> ORGANISM: Artificial Sequence
<220> FEATURE:
<223> OTHER INFORMATION: C4beta chain - Cys modification, Codon
    Optimized

<400> SEQUENCE: 95

| | |
|---|---|
| atgagcaacc aggtgctgtg ctgcgtggtg ctgtgtttcc tgggcgccaa caccgtggac | 60 |
| ggcggcatca cccagagccc caagtacctg ttccggaaag agggccagaa cgtcaccctg | 120 |
| agctgcgagc agaacctgaa ccacgacgcc atgtactggt acagacagga ccccggacag | 180 |
| ggcctgcggc tgatctacta cagccagatc gtgaacgact ccagaaggg agatatcgcc | 240 |
| gagggctaca gcgtgtccag agagaagaaa gagtccttcc cactgaccgt gaccagcgcc | 300 |
| cagaagaacc ccaccgcctt ctacctgtgc gccagctctc ctggcgccct gtacgagcag | 360 |

| | |
|---|---|
| tacttcggcc ctggcacccg gctgacagtg accgaggacc tgaagaacgt gttccccca | 420 |
| gaggtggccg tgttcgagcc tagcgaggcc gagatcagcc acacccagaa agccaccctc | 480 |
| gtgtgcctgg ccaccggctt ttaccccgac cacgtggaac tgtcttggtg ggtcaacggc | 540 |
| aaagaggtgc acagcggcgt ctgcaccgac ccccagcccc tgaaagagca gcccgccctg | 600 |
| aacgacagcc ggtactgtct gagcagcaga ctgagagtgt ccgccacctt ctggcagaac | 660 |
| ccccggaacc acttcagatg ccaggtgcag ttctacggcc tgagcgagaa cgacgagtgg | 720 |
| acccaggacc gggccaagcc cgtgacccag atcgtgtctg ctgaggcctg gggcagagcc | 780 |
| gattgcggct tcaccagcga gagctaccag cagggcgtgc tgagcgccac catcctgtac | 840 |
| gagatcctgc tgggcaaggc caccctgtac gccgtgctgg tgtccgccct ggtgctgatg | 900 |
| gccatggtca agcggaagga cagccggggc tga | 933 |

<210> SEQ ID NO 96
<211> LENGTH: 1809
<212> TYPE: DNA
<213> ORGANISM: Artificial Sequence
<220> FEATURE:
<223> OTHER INFORMATION: C4beta-P2A-C4alpha Construct - Cys
      modification, Codon Optimized

<400> SEQUENCE: 96

| | |
|---|---|
| atgagcaacc aggtgctgtg ctgcgtggtg ctgtgtttcc tgggcgccaa caccgtggac | 60 |
| ggcggcatca cccagagccc caagtacctg ttccggaaag agggccagaa cgtcaccctg | 120 |
| agctgcgagc agaacctgaa ccacgacgcc atgtactggt acagacagga ccccggacag | 180 |
| ggcctgcggc tgatctacta cagccagatc gtgaacgact ccagaaggg agatatcgcc | 240 |
| gagggctaca gcgtgtccag agagaagaaa gagtccttcc cactgaccgt gaccagcgcc | 300 |
| cagaagaacc caccgccctt ctacctgtgc gccagctctc tggcgccct gtacgagcag | 360 |
| tacttcggcc ctggcacccg gctgacagtg accgaggacc tgaagaacgt gttccccca | 420 |
| gaggtggccg tgttcgagcc tagcgaggcc gagatcagcc acacccagaa agccaccctc | 480 |
| gtgtgcctgg ccaccggctt ttaccccgac cacgtggaac tgtcttggtg ggtcaacggc | 540 |
| aaagaggtgc acagcggcgt ctgcaccgac ccccagcccc tgaaagagca gcccgccctg | 600 |
| aacgacagcc ggtactgtct gagcagcaga ctgagagtgt ccgccacctt ctggcagaac | 660 |
| ccccggaacc acttcagatg ccaggtgcag ttctacggcc tgagcgagaa cgacgagtgg | 720 |
| acccaggacc gggccaagcc cgtgacccag atcgtgtctg ctgaggcctg gggcagagcc | 780 |
| gattgcggct tcaccagcga gagctaccag cagggcgtgc tgagcgccac catcctgtac | 840 |
| gagatcctgc tgggcaaggc caccctgtac gccgtgctgg tgtccgccct ggtgctgatg | 900 |
| gccatggtca agcggaagga cagccggggc ggttccggag ccacgaactt ctctctgtta | 960 |
| aagcaagcag gagacgtgga agaaaacccc ggtcccatga ccagcatccg ggccgtgttc | 1020 |
| atcttcctgt ggctgcagct ggacctcgtc aacggcgaga cgtggaaca gcaccccagc | 1080 |
| accctgagcg tgcaggaagg cgacagcgcc gtcatcaagt gcacctacag cgactccgcc | 1140 |
| agcaactact ccccctggta caagcaggaa ctgggcaagc gccccagct gatcatcgac | 1200 |
| atccggtcca acgtgggcga agaaggac cagcggatcg ccgtgaccct gaacaagacc | 1260 |
| gccaagcact tcagcctgca catcaccgag acacagcccg aggactccgc cgtgtacttc | 1320 |
| tgtgccgcca ccgaggacta ccagctgatc tggggagccg gcaccaagct gatcattaag | 1380 |
| cccgacatcc agaaccccga ccctgccgtg taccagctgc gggacagcaa gagcagcgac | 1440 |

-continued

| | |
|---|---|
| aagagcgtgt gcctgttcac cgacttcgac agccagacca acgtgtccca gagcaaggac | 1500 |
| agcgacgtgt acatcaccga taagtgcgtg ctggacatgc ggagcatgga cttcaagagc | 1560 |
| aacagcgccg tggcctggtc aacaagagc gacttcgcct gcgccaacgc cttcaacaac | 1620 |
| agcattatcc ccgaggacac attcttccca agccccgaga gcagctgcga cgtgaagctg | 1680 |
| gtggaaaaga gcttcgagac agacaccaac ctgaacttcc agaacctcag cgtgatcggc | 1740 |
| ttccggatcc tgctgctgaa ggtggccggc ttcaacctgc tgatgaccct gcggctgtgg | 1800 |
| tccagctga | 1809 |

<210> SEQ ID NO 97
<211> LENGTH: 1809
<212> TYPE: DNA
<213> ORGANISM: Artificial Sequence
<220> FEATURE:
<223> OTHER INFORMATION: C4beta-P2A-C4alpha-DLT Construct - Cys
modification, Codon Optimized

<400> SEQUENCE: 97

| | |
|---|---|
| atgagcaacc aggtgctgtg ctgcgtggtg ctgtgtttcc tgggcgccaa caccgtggac | 60 |
| ggcggcatca cccagagccc caagtacctg ttccggaaag agggccagaa cgtcaccctg | 120 |
| agctgcgagc agaacctgaa ccacgacgcc atgtactggt acagacagga ccccggacag | 180 |
| ggcctgcggc tgatctacta cagccagatc gtgaacgact ccagaagggg agatatcgcc | 240 |
| gagggctaca gcgtgtccag agagaagaaa gagtccttcc cactgaccgt gaccagcgcc | 300 |
| cagaagaacc ccaccgcctt ctacctgtgc gccagctctc ctggcgccct gtacgagcag | 360 |
| tacttcggcc ctggcacccg gctgacagtg accgaggacc tgaagaacgt gttcccccca | 420 |
| gaggtggccg tgttcgagcc tagcgaggc gagatcagcc acacccagaa agccacccte | 480 |
| gtgtgcctgg ccaccggctt ttaccccgac cacgtggaac tgtcttggtg ggtcaacggc | 540 |
| aaagaggtgc acagcggcgt ctgcaccgac ccccagcccc tgaaagagca gcccgccctg | 600 |
| aacgacagcc ggtactgtct gagcagcaga ctgagagtgt ccgccacctt ctggcagaac | 660 |
| cccggaacc acttcagatg ccaggtgcag ttctacggcc tgagcgagaa cgacgagtgg | 720 |
| acccaggacc gggccaagcc cgtgacccag atcgtgtctg ctgaggcctg gggcagagcc | 780 |
| gattgcggct tcaccagcga gagctaccag cagggcgtgc tgagcgccac catcctgtac | 840 |
| gagatcctgc tgggcaaggc caccctgtac gccgtgctgg tgtccgccct ggtgctgatg | 900 |
| gccatggtca gcggaagga cagccggggc ggttccggag ccacgaactt ctctctgtta | 960 |
| aagcaagcag agacgtgga agaaaacccc ggtcccatga ccagcatccg gccgtgttc | 1020 |
| atcttcctgt ggctgcagct ggacctcgtc aacggcgaga cgtggaaca gcaccccagc | 1080 |
| accctgagcg tgcaggaagg cgacagcgcc gtcatcaagt gcacctacag cgactccgcc | 1140 |
| agcaactact ccccctggta caagcaggaa ctgggcaagc ggcccagct gatcatcgac | 1200 |
| atccggtcca acgtgggcga aagaaggac cagcggatcg ccgtgaccct gaacaagacc | 1260 |
| gccaagcact tcagcctgca catcaccgag acacagcccg aggactccgc cgtgtacttc | 1320 |
| tgtgccgcca ccgaggatct gacgctgatc tggggagccg gcaccaagct gatcattaag | 1380 |
| cccgacatcc agaaccccga ccctgccgtg taccagctgc gggacagcaa gagcagcgac | 1440 |
| aagagcgtgt gcctgttcac cgacttcgac agccagacca acgtgtccca gagcaaggac | 1500 |
| agcgacgtgt acatcaccga taagtgcgtg ctggacatgc ggagcatgga cttcaagagc | 1560 |
| aacagcgccg tggcctggtc aacaagagc gacttcgcct gcgccaacgc cttcaacaac | 1620 |

```
agcattatcc ccgaggacac attcttccca agccccgaga gcagctgcga cgtgaagctg    1680
gtggaaaaga gcttcgagac agacaccaac ctgaacttcc agaacctcag cgtgatcggc    1740
ttccggatcc tgctgctgaa ggtggccggc ttcaacctgc tgatgaccct gcggctgtgg    1800
tccagctga                                                            1809
```

```
<210> SEQ ID NO 98
<211> LENGTH: 66
<212> TYPE: DNA
<213> ORGANISM: Artificial Sequence
<220> FEATURE:
<223> OTHER INFORMATION: Porcine teschovirus-1 2A (P2A) peptide

<400> SEQUENCE: 98
ggaagcggag ctactaactt cagcctgctg aagcaggctg agacgtgga ggagaaccct     60 ggacct                                                               66
```

```
<210> SEQ ID NO 99
<211> LENGTH: 66
<212> TYPE: DNA
<213> ORGANISM: Artificial Sequence
<220> FEATURE:
<223> OTHER INFORMATION: Porcine teschovirus-1 2A (P2A) peptide - Codon
      Optimized

<400> SEQUENCE: 99
ggttccggag ccacgaactt ctctctgtta aagcaagcag gagacgtgga agaaaacccc    60
ggtccc                                                               66
```

```
<210> SEQ ID NO 100
<211> LENGTH: 63
<212> TYPE: DNA
<213> ORGANISM: Artificial Sequence
<220> FEATURE:
<223> OTHER INFORMATION: Thoseaasigna virus 2A (T2A) peptide

<400> SEQUENCE: 100
ggaagcggag agggcagagg aagtctgcta acatgcggtg acgtcgagga gaatcctgga    60
cct                                                                  63
```

```
<210> SEQ ID NO 101
<211> LENGTH: 69
<212> TYPE: DNA
<213> ORGANISM: Artificial Sequence
<220> FEATURE:
<223> OTHER INFORMATION: Equine rhinitis A virus (ERAV) 2A (E2A) peptide

<400> SEQUENCE: 101
ggaagcggac agtgtactaa ttatgctctc ttgaaattgg ctggagatgt tgagagcaac    60
cctggacct                                                            69
```

```
<210> SEQ ID NO 102
<211> LENGTH: 75
<212> TYPE: DNA
<213> ORGANISM: Artificial Sequence
<220> FEATURE:
<223> OTHER INFORMATION: Foot-and-Mouth disease virus 2A (F2A) peptide

<400> SEQUENCE: 102
ggaagcggag tgaaacagac tttgaatttt gaccttctca gttggcggg agacgtggag     60 tccaaccctg gacct                                                     75
```

<210> SEQ ID NO 103
<211> LENGTH: 411
<212> TYPE: DNA
<213> ORGANISM: Artificial Sequence
<220> FEATURE:
<223> OTHER INFORMATION: P1alpha chain variable domain

<400> SEQUENCE: 103

```
atgctgactg ccagcctgtt gagggcagtc atagcctcca tctgtgttgt atccagcatg    60
gctcagaagg taactcaagc gcagactgaa atttctgtgg tggagaagga ggatgtgacc   120
ttggactgtg tgtatgaaac ccgtgatact acttattact tattctggta caagcaacca   180
ccaagtggag aattggtttt ccttattcgt cggaactctt tgatgagca aatgaaata    240
agtggtcggt attcttggaa cttccagaaa tccaccagtt ccttcaactt caccatcaca   300
gcctcacaag tcgtggactc agcagtatac ttctgtgctc tgagtgaggc gcatagggat   360
agcaactatc agttaatctg gggcgctggg accaagctaa ttataaagcc a           411
```

<210> SEQ ID NO 104
<211> LENGTH: 426
<212> TYPE: DNA
<213> ORGANISM: Artificial Sequence
<220> FEATURE:
<223> OTHER INFORMATION: P15alpha chain variable domain

<400> SEQUENCE: 104

```
atggacaaga tcttaggagc atcattttta gttctgtggc ttcaactatg ctgggtgagt    60
ggccaacaga aggagaaaag tgaccagcag caggtgaaac aaagtcctca atctttgata   120
gtccagaaag gagggatttc aattataaac tgtgcttatg agaacactgc gtttgactac   180
tttccatggt accaacaatt ccctgggaaa ggccctgcat tattgatagc atacgtcca    240
gatgtgagtg aaaagaaaga aggaagattc acaatctcct tcaataaaag tgccaagcag   300
ttctcattgc atatcatgga tccccagcct ggagactcag ccacctactt ctgtgcagca   360
agccccccagg gggctgggag ttaccaactc actttcggga aggggaccaa actctcggtc   420
atacca                                                              426
```

<210> SEQ ID NO 105
<211> LENGTH: 408
<212> TYPE: DNA
<213> ORGANISM: Artificial Sequence
<220> FEATURE:
<223> OTHER INFORMATION: P18alpha chain variable domain

<400> SEQUENCE: 105

```
atgtcacttt ctagcctgct gaaggtggtc acagcttcac tgtggctagg acctggcatt    60
gcccagaaga taactcaaac ccaaccagga atgttcgtgc aggaaaagga ggctgtgact   120
ctggactgca catatgacac cagtgatcaa agttatggtc tattctggta caagcagccc   180
agcagtgggg aaatgatttt tcttatttat caggggtctt atgacgagca aatgcaaca    240
gaaggtcgct actcattgaa tttccagaag gcaagaaaat ccgccaacct tgtcatctcc   300
gcttcacaac tggggactc agcaatgtat ttctgtgcaa tcccgactct catggatagc    360
aactatcagt taatctgggg cgctgggacc aagctaatta taaagcca              408
```

<210> SEQ ID NO 106
<211> LENGTH: 393
<212> TYPE: DNA
<213> ORGANISM: Artificial Sequence
<220> FEATURE:
<223> OTHER INFORMATION: P20alpha chain variable domain

<400> SEQUENCE: 106

```
atgatgaaat ccttgagagt tttactagtg atcctgtggc ttcagttgag ctgggtttgg      60
agccaacaga aggaggtgga gcagaattct ggacccctca gtgttccaga gggagccatt     120
gcctctctca actgcactta cagtgaccga ggttcccagt ccttcttctg gtacagacaa     180
tattctggga aaagccctga gttgataatg tccatatact ccaatggtga caaagaagat     240
ggaaggttta cagcacagct caataaagcc agccagtatg tttctctgct catcagagac     300
tcccagccca gtgattcagc cacctacctc tgtgccgtgt agaaggcca gaagctgctc      360
tttgcaaggg ggaccatgtt aaaggtggat ctt                                  393
```

<210> SEQ ID NO 107
<211> LENGTH: 396
<212> TYPE: DNA
<213> ORGANISM: Artificial Sequence
<220> FEATURE:
<223> OTHER INFORMATION: P22alpha chain variable domain

<400> SEQUENCE: 107

```
atgatgaaat ccttgagagt tttactagtg atcctgtggc ttcagttgag ctgggtttgg      60
agccaacaga aggaggtgga gcagaattct ggacccctca gtgttccaga gggagccatt     120
gcctctctca actgcactta cagtgaccga gtttcccagt ccttcttctg gtacagacaa     180
tattctggga aaagccctga gttgataatg tccatatact ccaatggtga caaagaagat     240
ggaaggttta cagcacagct caataaagcc agccagtatg tttctctgct catcagagac     300
tcccagccca gtgattcagc cacctacctc tgtgccgcaa ataatgcagg caacatgctc     360
acctttggag ggggaacaag gttaatggtc aaaccc                                396
```

<210> SEQ ID NO 108
<211> LENGTH: 423
<212> TYPE: DNA
<213> ORGANISM: Artificial Sequence
<220> FEATURE:
<223> OTHER INFORMATION: (P1, P18)alpha chain constant domain - Cys
      Modification

<400> SEQUENCE: 108

```
gatatccaga accctgaccc tgccgtgtac cagctgagag actctaaatc cagtgacaag      60
tctgtctgcc tattcaccga ttttgattct caaacaaatg tgtcacaaag taaggattct     120
gatgtgtata tcacagacaa atgtgtgcta gacatgaggt ctatggactt caagagcaac     180
agtgctgtgg cctggagcaa caaatctgac tttgcatgtg caaacgcctt caacaacagc     240
attattccag aagacacctt cttccccagc ccagaaagtt cctgtgatgt caagctggtc     300
gagaaaagct ttgaaacaga tacgaaccta aactttcaaa acctgtcagt gattgggttc     360
cgaatcctcc tcctgaaagt ggccgggttt aatctgctca tgacgctgcg gctgtggtcc     420
agc                                                                   423
```

<210> SEQ ID NO 109
<211> LENGTH: 423
<212> TYPE: DNA
<213> ORGANISM: Artificial Sequence
<220> FEATURE:
<223> OTHER INFORMATION: (P15, P20)alpha chain constant domain - Cys
      Modification

<400> SEQUENCE: 109

```
aatatccaga accctgaccc tgccgtgtac cagctgagag actctaaatc cagtgacaag    60
tctgtctgcc tattcaccga ttttgattct caaacaaatg tgtcacaaag taaggattct   120
gatgtgtata tcacagacaa atgtgtgcta gacatgaggt ctatggactt caagagcaac   180
agtgctgtgg cctggagcaa caaatctgac tttgcatgtg caaacgcctt caacaacagc   240
attattccag aagacacctt cttccccagc ccagaaagtt cctgtgatgt caagctggtc   300
gagaaaagct ttgaaacaga tacgaaccta aactttcaaa acctgtcagt gattgggttc   360
cgaatcctcc tcctgaaagt ggccgggttt aatctgctca tgacgctgcg gctgtggtcc   420
agc                                                                  423
```

<210> SEQ ID NO 110
<211> LENGTH: 423
<212> TYPE: DNA
<213> ORGANISM: Artificial Sequence
<220> FEATURE:
<223> OTHER INFORMATION: P22alpha chain constant domain - Cys
      Modification

<400> SEQUENCE: 110

```
catatccaga accctgaccc tgccgtgtac cagctgagag actctaaatc cagtgacaag    60
tctgtctgcc tattcaccga ttttgattct caaacaaatg tgtcacaaag taaggattct   120
gatgtgtata tcacagacaa atgtgtgcta gacatgaggt ctatggactt caagagcaac   180
agtgctgtgg cctggagcaa caaatctgac tttgcatgtg caaacgcctt caacaacagc   240
attattccag aagacacctt cttccccagc ccagaaagtt cctgtgatgt caagctggtc   300
gagaaaagct ttgaaacaga tacgaaccta aactttcaaa acctgtcagt gattgggttc   360
cgaatcctcc tcctgaaagt ggccgggttt aatctgctca tgacgctgcg gctgtggtcc   420
agc                                                                  423
```

<210> SEQ ID NO 111
<211> LENGTH: 402
<212> TYPE: DNA
<213> ORGANISM: Artificial Sequence
<220> FEATURE:
<223> OTHER INFORMATION: P1beta chain variable domain

<400> SEQUENCE: 111

```
atgggctgca ggctgctctg ctgtgcggtt ctctgtctcc tgggagcggt ccccatggaa    60
acgggagtta cgcagacacc aagacacctg gtcatgggaa tgacaaataa gaagtctttg   120
aaatgtgaac aacatctggg gcataacgct atgtattggt acaagcaaag tgctaagaag   180
ccactggagc tcatgtttgt ctacaacttt aaagaacaga ctgaaaacaa cagtgtgcca   240
agtcgcttct cacctgaatg ccccaacagc tctcacttat ccttcacct acacaccctg   300
cagccagaag actcggccct gtatctctgt gccagcagcc aagatgaaca gttcctctac   360
aatgagcagt tcttcgggcc agggacacgg ctcaccgtgc ta                      402
```

<210> SEQ ID NO 112
<211> LENGTH: 399
<212> TYPE: DNA
<213> ORGANISM: Artificial Sequence
<220> FEATURE:
<223> OTHER INFORMATION: P15beta chain variable domain

<400> SEQUENCE: 112

```
atgggcacca gcctcctctg ctggatggcc ctgtgtctcc tgggggcaga tcacgcagat      60
actggagtct cccaggaccc cagacacaag atcacaaaga ggggacagaa tgtaactttc     120
aggtgtgatc caatttctga acacaaccgc ctttattggt accgacagac cctggggcag     180
ggcccagagt ttctgactta cttccagaat gaagctcaac tagaaaaatc aaggctgctc     240
agtgatcggt tctctgcaga gaggcctaag ggatctttct ccaccttgga gatccagcgc     300
acagagcagg gggactcggc catgtatctc tgtgccagca gcttagctta cgggaaagat     360
acgcagtatt ttggcccagg cacccggctg acagtgctc                            399

<210> SEQ ID NO 113
<211> LENGTH: 393
<212> TYPE: DNA
<213> ORGANISM: Artificial Sequence
<220> FEATURE:
<223> OTHER INFORMATION: P18beta chain variable domain

<400> SEQUENCE: 113
atgggctcct ggaccctctg ctgtgtgtcc ctttgcatcc tggtagcaaa gcacacagat      60
gctggagtta tccagtcacc ccggcacgag gtgacagaga tgggacaaga agtgactctg     120
agatgtaaac caatttcagg acatgactac cttttctggt acagacagac catgatgcgg     180
ggactggagt tgctcattta ctttaacaac aacgttccga tagatgattc agggatgccc     240
gaggatcgat tctcagctaa gatgcctaat gcatcattct ccactctgaa gatccagccc     300
tcagaaccca gggactcagc tgtgtacttc tgtgccagca gtgtctcggg ttcggaagct     360
ttctttggac aaggcaccag actcacagtt gta                                   393

<210> SEQ ID NO 114
<211> LENGTH: 384
<212> TYPE: DNA
<213> ORGANISM: Artificial Sequence
<220> FEATURE:
<223> OTHER INFORMATION: P20beta chain variable domain

<400> SEQUENCE: 114
atgggaatca ggctcctgtg tcgtgtggcc ttttgtttcc tggctgtagg cctcgtagat      60
gtgaaagtaa cccagagctc gagatatcta gtcaaaagga cgggagagaa agttttttctg    120 gaatgtgtcc aggatatgga ccatgaaaat atgttctggt atcgacaaga cccaggtctg    180 ggctacggc tgatctattt ctcatatgat gttaaaatga agaaaaagg agatattcct       240 gaggggtaca gtgtctctag agagaagaag gagcgcttct ccctgattct ggagtccgcc    300
agcaccaacc agacatctat gtacctctgt gccaccagtc atcagcccca gcattttggt    360
gatgggactc gactctccat ccta                                            384

<210> SEQ ID NO 115
<211> LENGTH: 387
<212> TYPE: DNA
<213> ORGANISM: Artificial Sequence
<220> FEATURE:
<223> OTHER INFORMATION: P22beta chain variable domain

<400> SEQUENCE: 115
atgggaatca ggctcctgtg tcgtgtggcc ttttgtttcc tggctgtagg cctcgtagat      60
gtgaaagtaa cccagagctc gagatatcta gtcaaaagga cgggagagaa agttttttctg    120 gaatgtgtcc aggatatgga ccatgaaaat atgttctggt atcgacaaga cccaggtctg    180 ggctacggc tgatctattt ctcatatgat gttaaaatga agaaaaagg agatattcct       240
```

```
gaggggtaca gtgtctctag agagaagaag gagcgcttct ccctgattct ggagtccgcc    300
agcaccaacc agacatctat gtacctctgt gccagcagtt ctataaatga gcagttcttc    360
gggccaggga cacggctcac cgtgcta                                        387
```

<210> SEQ ID NO 116
<211> LENGTH: 534
<212> TYPE: DNA
<213> ORGANISM: Artificial Sequence
<220> FEATURE:
<223> OTHER INFORMATION: (P18, P20)beta chain constant domain - Cys
      Modification

<400> SEQUENCE: 116

```
gaggacctga acaaggtgtt cccacccgag gtcgctgtgt ttgagccatc agaagcagag     60
atctcccaca cccaaaaggc cacactggtg tgcctggcca caggcttctt ccccgaccac    120
gtggagctga gctggtgggt gaatgggaag gaggtgcaca gtggggtctg cacggacccg    180 cagccectca aggagcagcc cgccctcaat gactccagat actgcctgag cagccgcctg    240
agggtctcgg ccaccttctg gcagaacccc cgcaaccact ccgctgtca agtccagttc    300 tacgggctct cggagaatga cgagtggacc caggataggg ccaaaccegt cacccagatc    360 gtcagcgccg aggcctgggg tagagcagac tgtggcttta cctcggtgtc ctaccagcaa    420
ggggtcctgt ctgccaccat cctctatgag atcctgctag gaaggccac cctgtatgct    480 gtgctggtca gcgccttgt gttgatggcc atggtcaaga gaaaggattt ctga           534
```

<210> SEQ ID NO 117
<211> LENGTH: 1842
<212> TYPE: DNA
<213> ORGANISM: Artificial Sequence
<220> FEATURE:
<223> OTHER INFORMATION: P1alpha-P2A-P1beta Construct - Cys Modification

<400> SEQUENCE: 117

```
atgctgactg ccagcctgtt gagggcagtc atagcctcca tctgtgttgt atccagcatg     60
gctcagaagg taactcaagc gcagactgaa atttctgtgg tggagaagga ggatgtgacc    120
ttggactgtg tgtatgaaac ccgtgatact acttattact tattctggta caagcaacca    180
ccaagtggag aattggtttt ccttattcgt cggaactctt ttgatgagca aaatgaaata    240
agtggtcggt attcttggaa cttccagaaa tccaccagtt ccttcaactt caccatcaca    300
gcctcacaag tcgtggactc agcagtatac ttctgtgctc tgagtgaggc catagggat    360 agcaactatc agttaatctg gggcgctggg accaagctaa ttataaagcc agatatccag    420
aaccctgacc ctgccgtgta ccagctgaga gactctaaat ccagtgacaa gtctgtctgc    480
ctattcaccg attttgattc tcaaacaaat gtgtcacaaa gtaaggattc tgatgtgtat    540
atcacagaca aatgtgtgct agacatgagg tctatggact caagagcaa cagtgctgtg    600 gcctggagca acaaatctga ctttgcatgt gcaaacgcct tcaacaacag cattattcca    660
gaagacacct tcttccccag cccagaaagt tcctgtgatg tcaagctggt cgagaaaagc    720
tttgaaacag atacgaacct aaactttcaa aacctgtcag tgattgggtt ccgaatcctc    780
ctcctgaaag tggccgggtt taatctgctc atgacgctgc ggctgtggtc cagcggttcc    840
ggagccacga acttctctct gttaaagcaa gcaggagacg tggaagaaaa ccccggtccc    900
atgggctgca ggctgctctg ctgtgcggtt ctctgtctcc tgggagcggt ccccatggaa    960
acgggagtta cgcagacacc aagacacctg gtcatgggaa tgacaaataa gaagtctttg   1020
```

| | |
|---|---|
| aaatgtgaac aacatctggg gcataacgct atgtattggt acaagcaaag tgctaagaag | 1080 |
| ccactggagc tcatgtttgt ctacaacttt aagaacaga ctgaaaacaa cagtgtgcca | 1140 |
| agtcgcttct cacctgaatg ccccaacagc tctcacttat tccttcacct acacaccctg | 1200 |
| cagccagaag actcggccct gtatctctgt gccagcagcc aagatgaaca gttcctctac | 1260 |
| aatgagcagt tcttcgggcc agggacacgg ctcaccgtgc tagaggacct gaaaaacgtg | 1320 |
| ttcccacccg aggtcgctgt gtttgagcca tcagaagcag agatctccca cacccaaaag | 1380 |
| gccacactgg tgtgcctggc cacaggcttc taccccgacc acgtggagct gagctggtgg | 1440 |
| gtgaatggga aggaggtgca cagtggggtc tgcacagacc cgcagcccct caaggagcag | 1500 |
| cccgccctca atgactccag atactgcctg agcagccgcc tgagggtctc ggccaccttc | 1560 |
| tggcagaacc cccgcaacca cttccgctgt caagtccagt tctacgggct ctcggagaat | 1620 |
| gacgagtgga cccaggatag ggccaaacct gtcacccaga tcgtcagcgc cgaggcctgg | 1680 |
| ggtagagcag actgtggctt cacctccgag tcttaccagc aagggtcct gtctgccacc | 1740 |
| atcctctatg agatcttgct agggaaggcc accttgtatg ccgtgctggt cagtgccctc | 1800 |
| gtgctgatgg ccatggtcaa gagaaaggat tccagaggct ag | 1842 |

<210> SEQ ID NO 118
<211> LENGTH: 1842
<212> TYPE: DNA
<213> ORGANISM: Artificial Sequence
<220> FEATURE:
<223> OTHER INFORMATION: P1alpha-P2A-P1beta construct - Cys
      modification, Codon Optimized

<400> SEQUENCE: 118

| | |
|---|---|
| atgctgacag cctctctgct gagagccgtg atcgccagca tctgcgtggt gtccagcatg | 60 |
| gcccagaaag tgacccaggc ccagaccgag atcagcgtgg tggaaaaaga agatgtgacc | 120 |
| ctggactgcg tgtacgagac acgggacacc acctactacc tgttctggta caagcagccc | 180 |
| cccagcggcg agctggtgtt cctgatccgg cggaacagct cgacgagca gaacgagatc | 240 |
| tccggccggt acagctggaa cttccagaag tccaccagca gcttcaactt caccatcacc | 300 |
| gccagccagg tggtggacag cgccgtgtac ttctgcgccc tgagcgaggc ccaccgggac | 360 |
| agcaactacc agctgatctg gggagccggc accaagctga tcatcaagcc cgacatccag | 420 |
| aaccccgacc ccgccgtgta ccagctgaga acagcaaga gcagcgacaa gagcgtgtgc | 480 |
| ctgttcaccg acttcgacag ccagaccaac gtgtcccaga gcaaggactc cgacgtgtac | 540 |
| atcaccgata agtgcgtgct ggacatgcgg agcatggact tcaagagcaa ctccgccgtg | 600 |
| gcctggtcca acaagagcga cttcgcctgc gccaacgcct tcaacaacag cattatcccc | 660 |
| gaggacacat tcttcccaag ccccgagagc agctgcgacg tgaagctggt ggaaaagagc | 720 |
| ttcgagacag acaccaacct gaatttccag aacctgagcg tgatcggctt ccggatcctg | 780 |
| ctgctgaagg tggccggctt caacctgctg atgaccctgc ggctgtggtc ctcaggttcc | 840 |
| ggagccacga acttctctct gttaaagcaa gcaggagacg tggaagaaaa cccggtcccc | 900 |
| atgggctgcc ggctgctgtg ttgcgccgtg ctgtgtctgc tgggcgccgt gcctatggaa | 960 |
| accggcgtga cccagacccc cagacacctg gtcatgggca tgaccaacaa gaaaagcctg | 1020 |
| aagtgcgagc agcacctggg ccacaacgcc atgtactggt ataagcagag cgccaagaaa | 1080 |
| cccctggaac tgatgttcgt gtacaacttc aagagcagaa ccgagaacaa cagcgtgccc | 1140 |
| agccggttca gccccgagtg ccccaatagc agccacctgt ttctgcatct gcacaccctg | 1200 |

```
cagcccgagg actccgccct gtacctgtgt gccagcagcc aggacgagca gttcctgtac    1260
aatgagcagt tcttcggccc tggcacccga ctgaccgtgc tggaagatct gaagaacgtg    1320 ttcccccag aggtggccgt gttcgagcct agcgaggccg agatctccca cacccagaaa    1380
gccaccctcg tgtgcctggc caccggcttc taccccgacc acgtggaact gtcttggtgg    1440
gtcaacggca agaggtgcag cagcggcgtc tgcaccgacc cccagcccct gaaagagcag    1500
cccgccctga cgacagccg gtactgcctg agcagccgac tcagagtgtc cgccaccttc    1560
tggcagaacc cccggaacca cttcagatgc caggtgcagt tctacggcct gagcgagaac    1620
gacgagtgga cccaggaccg ggccaagcct gtgacccaga tcgtgtcagc cgaggcctgg    1680
ggcagagccg attgcggctt caccagcgag agctaccagc agggcgtgct gagcgccacc    1740
atcctgtacg agatcctgct gggcaaggcc accctgtacg ctgtgctggt gtccgccctg    1800
gtgctgatgg ccatggtcaa gcggaaggac agccggggct ga                       1842

<210> SEQ ID NO 119
<211> LENGTH: 1854
<212> TYPE: DNA
<213> ORGANISM: Artificial Sequence
<220> FEATURE:
<223> OTHER INFORMATION: P15alpha-P2A-P15beta  Construct - Cys
      Modification

<400> SEQUENCE: 119
atggacaaga tcttaggagc atcatttta gttctgtggc ttcaactatg ctgggtgagt      60
ggccaacaga aggagaaaag tgaccagcag caggtgaaac aaagtcctca atctttgata    120
gtccagaaag gagggatttc aattataaac tgtgcttatg agaacactgc gtttgactac    180
tttccatggt accaacaatt ccctgggaaa ggccctgcat tattgatagc atacgtccca    240
gatgtgagtg aaaagaaaga aggaagattc acaatctcct tcaataaaag tgccaagcag    300
ttctcattgc atatcatgga ttcccagcct ggagactcag ccacctactt ctgtgcagca    360 agccccccagg gggctgggag ttaccaactc actttcggga aggggaccaa actctcggtc    420
ataccaaata tccagaaccc tgaccctgcc gtgtaccagc tgagagactc taaatccagt    480
gacaagtctg tctgcctatt caccgatttt gattctcaaa caaatgtgtc acaaagtaag    540
gattctgatg tgtatatcac agacaaatgt gtgctagaca tgaggtctat ggacttcaag    600
agcaacagtg ctgtggcctg agcaacaaaa tctgactttg catgtgcaaa cgccttcaac    660
aacagcatta ttccagaaga cacctttct cccagcccag aaagttcctg tgatgtcaag    720
ctggtcgaga aaagctttga aacagatacg aacctaaact ttcaaaacct gtcagtgatt    780
gggttccgaa tcctcctcct gaaagtggcc gggtttaatc tgctcatgac gctgcggctg    840
tggtccagcg gttccggagc cacgaacttc tctctgttaa gcaagcagg agacgtggaa    900 gaaaaccccg gtcccatggg caccagcctc ctctgctgga tggccctgtg tctcctgggg    960
gcagatcacg cagatactgg agtctcccag gaccccagac acaagatcac aaagagggga   1020
cagaatgtaa ctttcaggtg tgatccaatt tctgaacaca accgccttta ttggtaccga   1080
cagaccctgg ggcagggccc agagtttctg acttacttcc agaatgaagc tcaactagaa   1140
aaatcaaggc tgctcagtga tcggttctct gcagagaggc ctaagggatc tttctccacc   1200
ttggagatcc agcgcacaga gcagggggac tcggccatgt atctctgtgc cagcagctta   1260
gcttacggga agatacgca gtattttggc ccaggcaccc ggctgacagt gctcgaggac   1320
ctgaaaaacg tgttcccacc cgaggtcgct gtgtttgagc catcagaagc agagatctcc   1380
```

```
cacacccaaa aggccacact ggtgtgcctg gccacaggct tctaccccga ccacgtggag   1440
ctgagctggt gggtgaatgg gaaggaggtg cacagtgggg tctgcacaga cccgcagccc   1500
ctcaaggagc agcccgccct caatgactcc agatactgcc tgagcagccg cctgagggtc   1560
tcggccacct tctggcagaa ccccgcaac cacttccgct gtcaagtcca gttctacggg    1620
ctctcggaga tgacgagtg acccaggat agggccaaac ctgtcaccca gatcgtcagc     1680
gccgaggcct ggggtagagc agactgtggc ttcacctccg agtcttacca gcaaggggtc   1740
ctgtctgcca ccatcctcta tgagatcttg ctagggaagg ccaccttgta tgccgtgctg   1800
gtcagtgccc tcgtgctgat ggccatggtc aagagaaagg attccagagg ctag         1854
```

<210> SEQ ID NO 120
<211> LENGTH: 1854
<212> TYPE: DNA
<213> ORGANISM: Artificial Sequence
<220> FEATURE:
<223> OTHER INFORMATION: P15alpha-P2A-P15beta Construct - Cys
      modification, Codon Optimized

<400> SEQUENCE: 120

```
atggacaaga tcctgggcgc cagcttcctg gtgctgtggc tgcagctgtg ctgggtgtcc     60
ggccagcaga aagagaagtc cgaccagcag caggtcaaac agagcccca gagcctgatc    120 gtgcagaagg gcggcatcag catcatcaac tgcgcctacg agaataccgc cttcgactac    180
ttccccctgg tatcagcagtt ccccggcaag ggacctgccc tgctgatcgc catcagaccc    240
gacgtgtccg agaagaaaga gggccggttc accatcagct caacaagag cgccaagcag    300 ttcagcctgc acatcatgga cagccagccc ggcgacagcg ccacctactt tgtgccgcc    360 agccctcagg gcgctggcag ctaccacctg accttcggca agggcaccaa gctgagcgtg    420
atccccaaca tccagaaccc cgaccccgcc gtgtaccagc tgcgggacag caagagcagc    480
gacaagagcg tgtgcctgtt caccgacttc gacagccaga ccaacgtgtc ccagagcaag    540
gacagcgacg tgtacatcac cgataagtgc gtgctggaca tgcggagcat ggacttcaag    600
agcaacagcg ccgtggcctg gtccaacaag tccgacttcg cctgcgccaa cgccttcaac    660
aacagcatca tccccgagga cacattcttc ccaagccccg agagcagctg cgacgtgaag    720
ctggtggaaa agagcttcga cagacacc aacctgaact tccagaaccct gtccgtgatc    780 ggcttccgga tcctgctgct gaaggtggcc ggcttcaacc tgctgatgac cctgcggctg    840
tggtccagcg gttccggagc cacgaacttc tctctgttaa gcaagcagg agacgtggaa    900 gaaaaccccg gtcccatggg caccagcctg ctgtgctgga tggccctgtg cctgctgggc    960
gccgatcacg ctgataccgg cgtgtcccag gaccccggc acaagatcac caagcggggc   1020
cagaacgtga ccttcagatg cgaccccatc agcgagcaca accggctgta ctggtacaga   1080
cagaccctcg gccagggacc cgagttcctg acctacttcc agaatgaggc ccagctggaa   1140
aagtcccggc tgctgagcga ccggttcagc gccgaacggc caaggcag cttcagcacc   1200 ctggaaatcc agcggaccga gcaggagac tccgccatgt acctgtgtgc cagcagcctg   1260
gcctacggca aggacacaca gtacttcggc cctggcaccc ggctgaccgt gctgaagat    1320 ctgaagaacg tgttcccccc agaggtggcc gtgttcgagc cagcgaggc cgagatctct   1380 cacacccaga aagccaccct ggtctgcctg gccaccggct tctaccccga ccacgtggaa   1440
ctgtcttggt gggtcaacgg caagaggtc cacagcggcg tctgcaccga ccccagccc    1500 ctgaaagagc agcccgccct gaacgactct cggtactgcc tgagcagccg gctgagagtg   1560
```

```
tccgccacct tctggcagaa cccccggaac cacttcagat gccaggtgca gttctacggc    1620
ctgagcgaga acgacgagtg gacccaggac cgggccaagc ccgtgaccca gattgtgtct    1680
gccgaggcct ggggcagagc cgattgcggc ttcaccagcg agagctacca gcagggcgtg    1740
ctgagcgcca ccatcctgta cgagatcctg ctgggcaagg ccaccctgta cgccgtgctg    1800
gtgtccgctc tggtgctgat ggccatggtc aaacggaagg acagccgggg ctga          1854
```

<210> SEQ ID NO 121
<211> LENGTH: 1824
<212> TYPE: DNA
<213> ORGANISM: Artificial Sequence
<220> FEATURE:
<223> OTHER INFORMATION: P18alpha-P2A-P18beta Construct - Cys
      Modification

<400> SEQUENCE: 121

```
atgtcacttt ctagcctgct gaaggtggtc acagcttcac tgtggctagg acctggcatt     60
gcccagaaga taactcaaac ccaaccagga atgttcgtgc aggaaaagga ggctgtgact    120
ctggactgca catatgacac cagtgatcaa agttatggtc tattctggta caagcagccc    180
agcagtgggg aaatgatttt tcttatttat caggggtctt atgacgagca aaatgcaaca    240
gaaggtcgct actcattgaa tttccagaag gcaagaaaat ccgccaacct tgtcatctcc    300
gcttcacaac tggggactc agcaatgtat ttctgtgcaa tccgactct catggatagc    360 aactatcagt taatctgggg cgctgggacc aagctaatta taaagccaga tatccagaac    420
cctgaccctg ccgtgtacca gctgagagac tctaaatcca gtgacaagtc tgtctgccta    480
ttcaccgatt ttgattctca aacaaatgtg tcacaaagta aggattctga tgtgtatatc    540
acagacaaat gtgtgctaga catgaggtct atggacttca gagcaacag tgctgtggcc    600 tggagcaaca atctgacttt gcatgtgca aacgccttca caacagcat tattccagaa    660 gacaccttct cccccagccc agaaagttcc tgtgatgtca agctggtcga gaaaagcttt    720
gaaacagata cgaacctaaa ctttcaaaac ctgtcagtga ttgggttccg aatcctcctc    780
ctgaaagtgg ccgggttaaa tctgctcatg acgctgcggc tgtggtccag cggttccgga    840
gccacgaact tctctctgtt aaagcaagca ggagacgtgg aagaaaaccc cggtcccatg    900
ggctcctgga ccctctgctg tgtgtccctt gcatcctgg tagcaaagca cacagatgct    960
ggagttatcc agtcaccccg gcacgaggtg acagagatgg acaagaagt gactctgaga   1020 tgtaaaccaa tttcaggaca tgactacctt ttctggtaca gacagaccat gatgcgggga   1080
ctggagttgc tcatttactt taacaacaac gttccgatag atgattcagg gatgcccgag   1140
gatcgattct cagctaagat gcctaatgca tcattctcca ctctgaagat ccagccctca   1200
gaacccaggg actcagctgt gtacttctgt gccagcagtg tctcgggttc ggaagctttc   1260
tttggacaag gcaccagact cacagttgta gaggacctga acaaggtgtt cccacccgag   1320
gtcgctgtgt ttgagccatc agaagcagag atctcccaca cccaaaggc cacactggtg   1380 tgcctggcca caggcttctt ccccgaccac gtggagctga ctggtgggt gaatgggaag   1440 gaggtgcaca gtgggtctg cacggacccg cagcccctca aggagcagcc cgccctcaat   1500
gactccagat actgcctgag cagccgcctg agggtctcgg ccaccttctg gcagaacccc   1560
cgcaaccact ccgctgtca agtccagttc tacgggctct cggagaatga cgagtggacc   1620
caggataggg ccaaacccgt cacccagatc gtcagcgccg aggcctgggg tagagcagac   1680
tgtggcttta cctcggtgtc ctaccagcaa ggggtcctgt ctgccaccat cctctatgag   1740
```

```
atcctgctag ggaaggccac cctgtatgct gtgctggtca gcgcccttgt gttgatggcc    1800
atggtcaaga gaaaggattt ctga                                           1824

<210> SEQ ID NO 122
<211> LENGTH: 1824
<212> TYPE: DNA
<213> ORGANISM: Artificial Sequence
<220> FEATURE:
<223> OTHER INFORMATION: P18alpha-P2A-P18beta Construct - Cys
      modification, Codon Optimized

<400> SEQUENCE: 122
atgagcctga gcagcctgct gaaggtggtg accgcctctc tgtggctggg ccctggcatt     60
gcccagaaga tcacccagac ccagcccggc atgttcgtgc aggaaaaaga agccgtcacc    120
ctggactgca cctacgacac cagcgatcag agctacggcc tgttctggta caagcagccc    180
agcagcggcg agatgatctt cctgatctac cagggcagct acgacgagca gaacgccacc    240
gagggccggt acagcctgaa cttccagaag gcccggaagt ccgccaatct ggtgatcagc    300
gccagccagc tgggcgacag cgccatgtac ttttgcgcca tccccacccc tgatggacagc    360 aactaccagc tgatctgggg agccggcacc aagctgatca tcaagcccga catccagaac    420
cccgaccccg ccgtgtacca gctgagagac agcaagagca cgcacaagag cgtgtgcctg    480
ttcaccgact cgacagcca gaccaacgtg tcccagagca aggactccga cgtgtacatc    540
accgataagt gcgtgctgga catgcggagc atggacttca gagcaactc cgccgtggcc    600 tggtccaaca gagcgactt cgcctgcgcc aacgccttca caacagcat tatccccgag    660 gacacattct cccaagccc cgagagcagc tgcgacgtga agctggtgga aaagagcttc    720
gagacagaca ccaacctgaa tttccagaac ctgagcgtga tcggcttccg gatcctgctg    780
ctgaaggtgg ccggcttcaa cctgctgatg accctgcggc tgtggtcctc tggttccgga    840
gccacgaact tctctctgtt aaagcaagca ggagacgtgg aagaaaaccc cggtcccatg    900
ggcagctgga cccctgtgctg cgtgagcctg tgcatcctgg tggccaagca caccgacgcc    960
ggcgtcatcc agagcccag gcacgaggtg accgagatgg gccaggaagt gaccctgcgc   1020
tgcaagccca tcagcggcca cgactacctg ttctggtaca ggcagaccat gatgcgggcc   1080
ctggaactgc tgatctactt caacaacaac gtgcccatcg acgacagcgg catgcccgag   1140
gaccggttca gcgccaagat gcccaacgcc agcttcagca ccctgaagat ccagcccagc   1200
gagcccgggg actctgccgt gtatttctgt gcctcctccg tgtccggcag cgaggccttc   1260
tttgggcagg gcaccagact gacagtggtg gaggacctga caaggtgttt cccccccgag   1320
gtggccgtgt ttgagcccag cgaggccgag atcagccaca cccagaaagc caccctggtg   1380
tgcctggcca ccggcttttt ccccgaccac gtggagctgt cttggtgggt gaacggcaaa   1440
gaggtgcaca cggcgtctg caccgacccc cagcccctga agagcagcc cgccctgaac   1500 gacagccggt actgcctgag cagcagactg cgggtgtccg ccaccttctg gcagaacccc   1560
cggaaccact tccggtgcca ggtgcagttc tacggcctga gcgagaacga cgagtggacc   1620
caggatagag ccaagcctgt gacccagatc gtgtctgccg aagcctgggg cagagccgac   1680
tgcggcttca ccagcgtgtc ctaccagcag ggggtgctgt ccgccacaat cctgtacgag   1740
atcctgctgg gcaaggccac actgtacgcc gtgctggtgt ccgctctggt gctgatggcc   1800
atggtgaagc ggaaggactt ctga                                          1824
```

<210> SEQ ID NO 123
<211> LENGTH: 1800
<212> TYPE: DNA
<213> ORGANISM: Artificial Sequence
<220> FEATURE:
<223> OTHER INFORMATION: P20alpha-P2A-P20beta Construct - Cys Modification

<400> SEQUENCE: 123

```
atgatgaaat ccttgagagt tttactagtg atcctgtggc ttcagttgag ctgggtttgg      60
agccaacaga aggaggtgga gcagaattct ggacccctca gtgttccaga gggagccatt     120
gcctctctca actgcactta cagtgaccga ggttcccagt ccttcttctg gtacagacaa     180
tattctggga aaagccctga gttgataatg tccatatact ccaatggtga caaagaagat     240
ggaaggttta cagcacagct caataaagcc agccagtatg tttctctgct catcagagac     300
tcccagccca gtgattcagc cacctacctc tgtgccgtgt tagaaggcca agctgctc      360
tttgcaaggg ggaccatgtt aaaggtggat cttaatatcc agaaccctga ccctgccgtg     420
taccagctga gagactctaa atccagtgac aagtctgtct gcctattcac cgatttgat      480
tctcaaacaa atgtgtcaca agtaaggat tctgatgtgt atatcacaga caatgtgtg      540
ctagacatga ggtctatgga cttcaagagc aacagtgctg tggcctggag caacaaatct     600
gactttgcat gtgcaaacgc cttcaacaac agcattattc agaagacac cttcttcccc     660
agcccagaaa gttcctgtga tgtcaagctg gtcgagaaaa gctttgaaac agatacgaac     720
ctaaactttc aaaacctgtc agtgattggg ttccgaatcc tcctcctgaa gtggccggg      780
tttaatctgc tcatgacgct gcggctgtgg tccagcggtt ccggagccac gaacttctct     840
ctgttaaagc aagcaggaga cgtggaagaa accccggtc ccatgggaat caggctcctg     900
tgtcgtgtgg ccttttgttt cctggctgta ggcctcgtag atgtgaaagt aacccagagc     960
tcgagatatc tagtcaaaag gacgggagag aaagttttc tggaatgtgt ccaggatatg    1020
gaccatgaaa atatgttctg gtatcgacaa gacccaggtc tggggctacg gctgatctat    1080
ttctcatatg atgttaaaat gaaagaaaaa ggagatattc ctgaggggta cagtgtctct    1140
agagagaaga agagcgctt ctccctgatt ctggagtccg ccagcaccaa ccagacatct    1200
atgtacctct gtgccaccag tcatcagccc cagcattttg gtgatgggac tcgactctcc    1260
atcctagagg acctgaacaa ggtgttccca cccgaggtcg ctgtgtttga gccatcagaa    1320
gcagagatct cccacaccca aaaggccaca ctggtgtgcc tggccacagg cttcttcccc    1380
gaccacgtgg agctgagctg gtgggtgaat gggaaggagg tgcacagtgg ggtctgcacg    1440
gacccgcagc ccctcaagga gcagcccgcc tcaatgact ccagatactg cctgagcagc    1500
cgcctgaggg tctcggccac cttctggcag aaccccgca accacttccg ctgtcaagtc    1560
cagttctacg ggctctcgga gaatgacgag tggacccagg atagggccaa acccgtcacc    1620
cagatcgtca gcgccgaggc ctgggggtaga gcagactgtg ctttacctc ggtgtcctac    1680
cagcaagggg tcctgtctgc caccatcctc tatgagatct gctagggaa ggccaccctg    1740
tatgctgtgc tggtcagcgc ccttgtgttg atggccatgg tcaagagaaa ggatttctga    1800
```

<210> SEQ ID NO 124
<211> LENGTH: 1800
<212> TYPE: DNA
<213> ORGANISM: Artificial Sequence
<220> FEATURE:
<223> OTHER INFORMATION: P20alpha-P2A-P20beta Construct - Cys modification, Codon Optimized

<400> SEQUENCE: 124

```
atgatgaagt ccctgcgggt gctgctggtc atcctgtggc tgcagctgag ctgggtctgg      60
tcccagcaga aagaggtgga acagaacagc ggccctctga gcgtgcccga aggcgctatc     120
gccagcctga actgcaccta cagcgaccgg ggcagccaga gcttcttctg gtacagacag     180
tacagcggca agagccccga gctgatcatg agcatctaca gcaacggcga caaagaggac     240
ggccggttca ccgcccagct gaacaaggcc agccagtacg tgtccctgct gatccgggac     300
agccagccca gcgacagcgc cacatacctg tgcgccgtgc tggaaggcca agctgctg       360
ttcgccagag gcaccatgct gaaggtggac ctgaacatcc agaacccga ccccgccgtg      420
taccagctgc gggatagcaa gagcagcgac aagagcgtgt gcctgttcac cgacttcgac    480
agccagacca acgtgtccca gagcaaggac agcgacgtgt acatcaccga taagtgcgtg    540
ctggacatgc ggagcatgga cttcaagagc aacagcgccg tggcctggtc caacaagagc    600
gacttcgcct gcgccaacgc cttcaacaac agcattatcc ccgaggacac attcttccca    660
agccccgaga gcagctgcga cgtgaagctg gtggaaaaga gcttcgagac agacaccaac    720
ctcaacttcc agaacctgag cgtgatcggc ttccggatcc tgctgctgaa agtggccggc    780
ttcaacctgc tgatgaccct gcggctgtgg tccagcggtt ccggagccac gaacttctct    840
ctgttaaagc aagcaggaga cgtggaagaa acccggtc ccatgggcat ccggctgctg      900
tgcagagtgg ccttctgctt cctggccgtg ggcctggtgg acgtgaaagt gacccagagc    960
agcagatacc tggtcaagcg gaccggcgag aaggtgttcc tggaatgcgt gcaggatatg   1020
gaccacgaga acatgttttg gtacaggcag gaccctggac tgggcctgcg gctgatctac   1080
ttctcctacg acgtgaagat gaaggaaaag ggcgacatcc ccgagggcta cagcgtgtcc   1140
agagagaaga aagagcggtt cagcctgatc ctggaaagcg ccagcaccaa ccagaccagc   1200
atgtacctgt gtgccaccct ccaccagccc cagcactttg gcgacggcac ccggctgagc   1260
atcctggaag atctgaacaa ggtgttcccc ccagaggtgg ccgtgttcga gcctagcgag   1320
gccgagatca gccacaccca gaaagccacc ctcgtgtgcc tggccaccgg ctttttcccc   1380
gaccacgtgg aactgtcttg gtgggtcaac ggcaaagagg tgcacagcgg cgtctgcacc   1440
gaccccagc ccctgaaaga gcagcccgcc ctgaacgaca ccggtactg cctgagcagc   1500
cgactgagag tgtccgccac cttctggcag aaccccgga accacttcag atgccaggtg    1560
cagttctacg gcctgagcga aaacgacgag tggacacagg accgggccaa gcccgtgacc   1620
cagatcgtgt cagccgaggc ctggggcaga gccgattgcg gcttcaccag cgtgtcctat   1680
cagcagggcg tgctgagcgc caccatcctg tacgagatcc tgctgggcaa ggccaccctg   1740
tatgccgtgc tggtgtccgc cctggtgctg atggccatgg tcaagagaaa ggacttctga   1800
```

<210> SEQ ID NO 125
<211> LENGTH: 1812
<212> TYPE: DNA
<213> ORGANISM: Artificial Sequence
<220> FEATURE:
<223> OTHER INFORMATION: P22alpha-P2A-P22beta Construct - Cys Modification

<400> SEQUENCE: 125

```
atgatgaaat ccttgagagt tttactagtg atcctgtggc ttcagttgag ctgggtttgg      60
agccaacaga aggaggtgga gcagaattct ggaccctca gtgttccaga gggagccatt      120
gcctctctca actgcactta cagtgaccga gtttcccagt ccttcttctg gtacagacaa      180
```

```
tattctggga aaagccctga gttgataatg tccatatact ccaatggtga caagaagat      240 ggaaggttta cagcacagct caataaagcc agccagtatg tttctctgct catcagagac     300
tcccagccca gtgattcagc cacctacctc tgtgccgcaa ataatgcagg caacatgctc     360
acctttggag ggggaacaag gttaatggtc aaaccccata tccagaaccc tgaccctgcc     420
gtgtaccagc tgagagactc taaatccagt gacaagtctg tctgcctatt caccgatttt     480
gattctcaaa caaatgtgtc acaaagtaag gattctgatg tgtatatcac agacaaatgt     540
gtgctagaca tgaggtctat ggacttcaag agcaacagtg ctgtggcctg agcaacaaa      600 tctgactttg catgtgcaaa cgccttcaac aacagcatta ttccagaaga caccttcttc     660
cccagcccag aaagttcctg tgatgtcaag ctggtcgaga aaagctttga acagatacg      720 aacctaaact ttcaaaacct gtcagtgatt gggttccgaa tcctcctcct gaaagtggcc     780
gggtttaatc tgctcatgac gctgcggctg tggtccagcg gttccggagc cacgaacttc     840
tctctgttaa gcaagcagg agacgtggaa gaaaaccccg gtcccatggg aatcaggctc      900
ctgtgtcgtg tggccttttg tttcctggct gtaggcctcg tagatgtgaa agtaacccag     960
agctcgagat atctagtcaa aaggacggga gagaaagttt ttctggaatg tgtccaggat    1020
atggaccatg aaaatatgtt ctggtatcga caagacccag tctggggct acggctgatc     1080 tatttctcat atgatgttaa aatgaaagaa aaggagata ttcctgaggg gtacagtgtc     1140
tctagagaga agaaggagcg cttctccctg attctggagt ccgccagcac aaccagaca    1200 tctatgtacc tctgtgccag cagttctata aatgagcagt tcttcgggcc agggacacgg    1260
ctcaccgtgc tagaggacct gaaaaacgtg ttcccacccg aggtcgctgt gtttgagcca    1320
tcagaagcag agatctccca cacccaaaag gccacactgg tgtgcctggc cacaggcttc    1380
taccccgacc acgtggagct gagctggtgg gtgaatggga aggaggtgca cagtggggtc    1440
tgcacagacc cgcagcccct caaggagcag cccgccctca tgactccag atactgcctg    1500 agcagccgcc tgagggtctc ggccaccttc tggcagaacc ccgcaacca ttccgctgt    1560 caagtccagt tctacgggct ctcggagaat gacgagtgga cccaggatag ggccaaacct     1620
gtcacccaga tcgtcagcgc cgaggcctgg ggtagagcag actgtggctt cacctccgag    1680
tcttaccagc aaggggtcct gtctgccacc atcctctatg agatcttgct agggaaggcc     1740
accttgtatg ccgtgctggt cagtgccctc gtgctgatgg ccatggtcaa gagaaaggat    1800
tccagaggct ag                                                        1812
```

<210> SEQ ID NO 126
<211> LENGTH: 1812
<212> TYPE: DNA
<213> ORGANISM: Artificial Sequence
<220> FEATURE:
<223> OTHER INFORMATION: P22alpha-P2A-P22beta Construct - Cys
      modification, Codon Optimized

<400> SEQUENCE: 126

```
atgatgaagt ccctgcgggt gctgctggtc atcctgtggc tgcagctgag ctgggtctgg      60
tcccagcaga agaggtggaa acagaacagc ggccctctga gcgtgcccga aggcgctatc     120
gccagcctga actgcaccta cagcgaccgg gtgtcccaga gcttcttctg gtacagacag     180
tacagcggca agagccccga gctgatcatg agcatctaca gcaacggcga caaagaggac     240
ggccggttca ccgcccagct gaacaaggcc agccagtacg tgtccctgct gatccgggac     300
agccagccca gcgacagcgc cacataccct gtgcgccgcca acaacgccgg caacatgctg     360
```

```
accttcggcg gaggcacccg gctgatggtc aagccccaca tccagaaccc cgaccccgcc      420
gtgtaccagc tgcgggatag caagagcagc gacaagagcg tgtgcctgtt caccgacttc      480
gacagccaga ccaacgtgtc ccagtccaag gacagcgacg tgtacatcac cgataagtgc      540
gtgctggaca tgcggagcat ggacttcaag agcaacagcg ccgtggcctg gtccaacaag      600
agcgacttcg cctgcgccaa cgccttcaac aacagcatta tccccgagga cacattcttc      660
ccaagccccg agagcagctg cgacgtgaag ctggtggaaa agagcttcga cagacacc       720
aacctgaact tccagaacct gagcgtgatc ggcttccgga tcctgctgct gaaggtggcc      780
ggcttcaacc tgctgatgac cctgcggctg tggtccagcg gttccggagc cacgaacttc      840
tctctgttaa gcaagcagg agacgtggaa gaaaaccccg gtcccatggg catccggctg       900
ctgtgcagag tggccttctg cttcctggcc gtgggcctgg tggacgtgaa agtgacccag      960
agcagcagat acctggtcaa gcggaccggc gagaaggtgt tcctggaatg cgtgcaggat     1020
atggaccacg agaacatgtt ttggtacagg caggatcctg gactgggact gcggctgatc     1080
tacttctcct acgacgtgaa gatgaaggaa aagggcgaca tccccgaggg ctacagcgtg     1140
tccagagaga gaaagagcg gttcagcctg atcctggaaa gcgccagcac caaccagacc     1200
agcatgtacc tgtgtgccag cagcagcatc aacgagcagt tcttcggccc tggcaccaga     1260
ctgaccgtgc tggaagatct gaagaacgtg ttcccccag aggtggccgt gttcgagcct     1320
agcgaggcca gatcagcca cacccagaaa gccaccctcg tgtgcctggc caccggcttc     1380
taccccgacc acgtggaact gtcttggtgg gtcaacggca agaggtgca cagcggcgtc     1440
tgcaccgacc cccagcccct gaaagagcag cccgccctga cgacagccg gtactgcctg     1500
agcagcagac tgagagtgtc cgccaccttc tggcagaacc cccggaacca cttcagatgc     1560
caggtgcagt tttacggcct gagcgagaac gacgagtgga cccaggaccg ggccaagccc     1620
gtgacccaga tcgtgtcagc cgaggcctgg ggcagagccg attgcggctt caccagcgag     1680
agctaccagc agggcgtgct gagcgccacc atcctgtacg agatcctgct gggcaaggcc     1740
accctgtacg ccgtgctggt gtccgccctg gtgctgatgg ccatggtcaa gagaaaggac     1800
agccggggct ga                                                         1812

<210> SEQ ID NO 127
<211> LENGTH: 9
<212> TYPE: PRT
<213> ORGANISM: Artificial Sequence
<220> FEATURE:
<223> OTHER INFORMATION: EBV peptide

<400> SEQUENCE: 127

Gly Leu Cys Thr Leu Val Ala Met Leu
1               5

<210> SEQ ID NO 128
<211> LENGTH: 387
<212> TYPE: DNA
<213> ORGANISM: Artificial Sequence
<220> FEATURE:
<223> OTHER INFORMATION: C4 alpha chain variable domain - Codon
      Optimized

<400> SEQUENCE: 128
atgaccagca tccgggccgt gttcatcttc ctgtggctgc agctggacct cgtcaacggc       60
gagaacgtgg aacagcaccc cagcaccctg agcgtgcagg aaggcgacag cgccgtcatc      120
aagtgcacct acagcgactc cgccagcaac tacttcccct ggtacaagca ggaactgggc      180
```

```
aagcggcccc agctgatcat cgacatccgg tccaacgtgg gcgagaagaa ggaccagcgg    240
atcgccgtga ccctgaacaa gaccgccaag cacttcagcc tgcacatcac cgagacacag    300
cccgaggact ccgccgtgta cttctgtgcc gccaccgagg actaccagct gatctgggga    360
gccggcacca agctgatcat taagccc                                        387
```